US008709412B2

(12) United States Patent
Jones et al.

(10) Patent No.: US 8,709,412 B2
(45) Date of Patent: Apr. 29, 2014

(54) MODULATION OF TIM RECEPTOR ACTIVITY IN COMBINATION WITH CYTOREDUCTIVE THERAPY

(75) Inventors: Jennifer Jones, Palo Alto, CA (US); Rosemarie Dekruyff, Stanford, CA (US); Dale T. Umetsu, Newton, MA (US); Gordon J. Freeman, Boston, MA (US); Susan Jane Knox, Stanford, CA (US)

(73) Assignees: The Board of Trustees of the Leland Stanford Junior University, Palo Alto, CA (US); Dana-Farber Cancer Institute, Inc., Boston, MA (US); Children's Hospital Corporation, Boston, MA (US)

( * ) Notice: Subject to any disclaimer, the term of this patent is extended or adjusted under 35 U.S.C. 154(b) by 0 days.

(21) Appl. No.: 13/176,651

(22) Filed: Jul. 5, 2011

(65) Prior Publication Data

US 2012/0156224 A1 Jun. 21, 2012

Related U.S. Application Data

(63) Continuation-in-part of application No. 12/485,765, filed on Jun. 16, 2009, now abandoned, which is a continuation of application No. 10/188,012, filed on Jul. 1, 2002, now Pat. No. 7,553,939.

(60) Provisional application No. 60/302,344, filed on Jun. 29, 2001.

(51) Int. Cl.
*A61K 39/395* (2006.01)

(52) U.S. Cl.
USPC ........................................ 424/130.1

(58) Field of Classification Search
None
See application file for complete search history.

(56) References Cited

U.S. PATENT DOCUMENTS

| | | | | |
|---|---|---|---|---|
| 5,721,351 | A | 2/1998 | Levinson | |
| 5,986,059 | A | 11/1999 | Shanafelt et al. | |
| 6,084,083 | A | 7/2000 | Levinson | |
| 6,204,371 | B1 | 3/2001 | Levinson | |
| 6,232,107 | B1 | 5/2001 | Bryan et al. | |
| 6,288,218 | B1 | 9/2001 | Levinson | |
| 7,060,458 | B1 | 6/2006 | Doucette-Stamm et al. | |
| 7,470,428 | B2 * | 12/2008 | Kuchroo et al. | 424/130.1 |
| 2005/0084449 | A1 | 4/2005 | Landes et al. | |
| 2005/0276756 | A1 | 12/2005 | Hoo et al. | |
| 2009/0068178 | A1 | 3/2009 | Crowley et al. | |
| 2009/0252737 | A1 | 10/2009 | McIntire et al. | |

FOREIGN PATENT DOCUMENTS

| | | |
|---|---|---|
| WO | 97/44460 | 11/1997 |
| WO | 99/38881 | 8/1999 |
| WO | 02/081517 | 10/2002 |

OTHER PUBLICATIONS

Jeon et al., Science, 1999, 286: 1141-1146.*
Debily et al., Human Molecular Genetics, 2004, 13: 323-334.*
Gafvelin et al., Acta Chem. Scand., 1991, 45: 63-67 [abstract only].*
Huang (Pharmacology and Therapeutics, 2000, 86: 201-215.*
Van de Weyer et al. (Biochemical and Biophysical Research Communications, (2006) 351: 571-576).*
Freeman et al. (Immunol. Rev., 2010, 235: 172-189).*
Lee at al. (J. Immunol., 2010, 185: 5225-5235).*
Rennert (Immunology Letters, 2011, 141: 28-35).*
Carninci; et al. "Normalization and Substraction of Cap-Trapper-Selected cDNAs to Prepare Full-Length cDNA Libraries for Rapid Discovery of New Genes," Genome Res. (2000), 10(10):1617-30.
Feigelstock; et al., "The Human Homolog of HAVcr-1 Codes for a Hepatitis A Virus Cellular Receptor," J. Virology, (1998), 72(8):6621-28.
GenBank Accession No. AF450242, Feb. 2002, pp. 1-3.
GenBank Accession No. AI506340 Marra et al. "The WashU-NCI Mouse EST Project"1999.
GenBank Accession No. BAB55044 Isogai and Otsuki, "NEDO human cDNA sequencing project" submitted May 10, 2001.
GenBank Accession No. Q8CIC7 Strausberg et al. "Generation and initial analysis of more than 15,000 full-length human and mouse cDNA sequences" Proc. Natl. Acad. Sci. U.S.A. 99(26), 16899-16903 (2002).
GenBank Accession No. Q96H15 Gerhard et al. "The status, quality, and expansion of the NIH full-length cDNA project: the Mammalian Gene Collection (MGC)" Genome Res. 14 (10B), 2121-2127 (2004).
GenBank Accession No. XM-011327 NCBI Annotation Project, submitted Jul. 31, 2002 National Center for Biotechnology Information, NIH, Bethesda, MD 20894, USA.
Ichimura; et al. "Kidney Injury Molecule-1 (KIM-1), a Putative Epithilial Cell Adhesion Molecule Containing a Novel Immunoglobin Domain, Is Up-regulated in Renal Cells After Injury," J. Biol. Chem. (1998), 273(7):4135-4142.
McIntire; et al., "Identification of Tapr (an airway hyperreactivity regulatory locus) and the linked Tim gene family", Nature Immunol (2001), 2(12):1109-1116.
Meyers; et al., "The TIM gene family regulates autoimmune and allergic diseases", TRENDS in Mol. Med. (2005), 11:362-369.

(Continued)

*Primary Examiner* — Ilia Ouspenski
(74) *Attorney, Agent, or Firm* — Bozicevic, Field & Francis LLP; Pamela J. Sherwood

(57) ABSTRACT

A genetic locus and corresponding family of proteins associated with regulation of immune function and cell survival are provided. These genes encode cell surface molecules with conserved IgV and mucin domains. The locus comprising the TIM family is genetically associated with immune dysfunction, including asthma. Furthermore, the TIM gene family is located within a region of human chromosome 5 that is commonly deleted in malignancies and myelodysplastic syndrome. Polymorphisms in the gene sequences are associated with the development of airway hyperreactivity and allergic inflammation, and T cell production of IL-4 and IL-13. The proteins include the human hepatitis A cellular receptor, hHAVcr-1.

6 Claims, 14 Drawing Sheets

(56) References Cited

OTHER PUBLICATIONS

Monney, et al., "Th1-specific cell surface protein Tim-3 regulates macrophage activation and severity of an autoimmune disease", Nature (2002), 415(6871):536-541.
Rosenwasser; et al., "Genetics of atopy and asthma: the rationale behind promoter-based candidate gene studies", Amer. J. Respir. Crit. Care Med. (1997), 156(4):S152-S155.
Shakhov; et al., "SMUCKLER/TIM4 is a distinct member of TIM family expressed by stomal cells of secondary lymphoid tissues and associated with lymphotoxin signalling", Eur. J. Immun. (2004), 34(2):494-503.
Xa; et al. "Immune Response and Airway Reactivity in Wild and IL-4 Knockout Mice Exposed to Latex Allergens," Int. Arch. Aller. Immunol. (1999), 118(1):23-29.
Dekruyff; et al., "T Cell/Transmembrane, Ig, and Mucin-3 Allelic Variants Differentially Recognize Phosphatidylserine and Mediate Phagocytosis of Apoptotic Cells", J. Immunol. (Feb. 2010), 184(4):1918-1930.
Freeman; et al., "TIM genes: a family of cell surface phosphatidylserine receptors that regulate innate and adaptive immunity", Immunol Rev. (May 2010), 235(1):172-189.
Kobayashi; et al., "T cell Immunoglobulin Mucin Protein (TIM)-4 binds phosphatidylserine and mediates uptake of apoptotic cells", Immunity (Dec. 2007), 27(6):927-940.
Lee; et al., "Apoptotic Cells Activate NKT Cells through T Cell Ig-Like Mucin-Like-1 Resulting in Airway Hyperreactivity", J. Immunol. (Nov. 2010), 185(9):5225-5235.
Yao; et al., "Differences in Bcl-2 expression by T-cell subsets alter their balance after in vivo irradiation to favor CD41Bcl-2hi NKT cells", Eur. J. Immunol. (Mar. 2009), 39(3):763-775.
Yao; et al., "Selective Resistance of CD44hi T Cells to p53 Dependent Cell Death Results in Persistence of Immunologic Memory after Total Body Irradiation", J. Immunol. (Oct. 2011), 187(8):4100-4108.

* cited by examiner

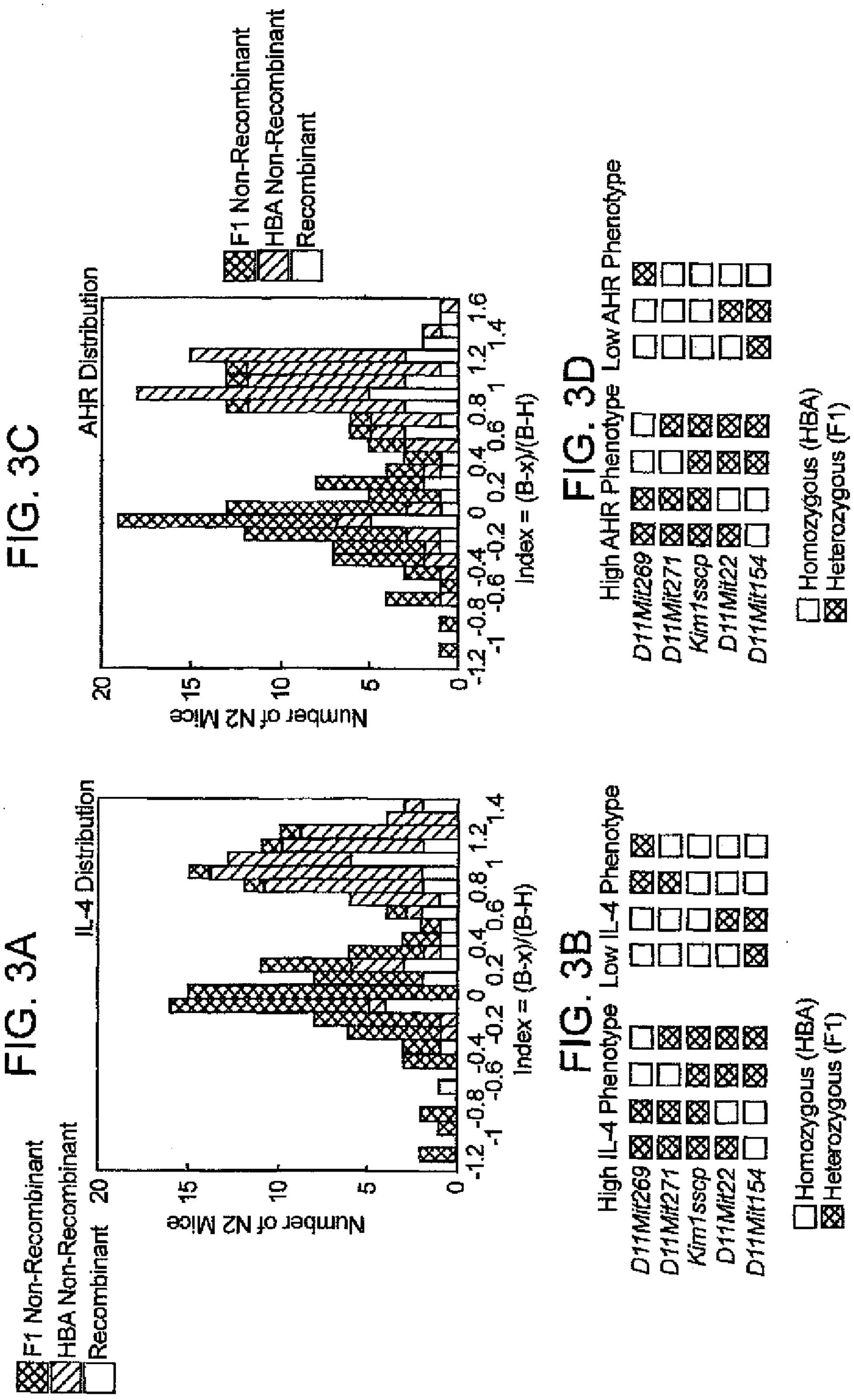

FIG. 3A
IL-4 Distribution
F1 Non-Recombinant
HBA Non-Recombinant
Recombinant
Number of N2 Mice
Index = (B-x)/(B-H)
FIG. 3B
High IL-4 Phenotype
Low IL-4 Phenotype
D11Mit269
D11Mit271
Kim1sscp
D11Mit22
D11Mit154
Homozygous (HBA)
Heterozygous (F1)
FIG. 3C
AHR Distribution
F1 Non-Recombinant
HBA Non-Recombinant
Recombinant
Number of N2 Mice
Index = (B-x)/(B-H)
FIG. 3D
High AHR Phenotype
Low AHR Phenotype
D11Mit269
D11Mit271
Kim1sscp
D11Mit22
D11Mit154
Homozygous (HBA)
Heterozygous (F1)

FIG. 5A

```
Mouse TIM-1      MNQIQVFISGLILLLPGTVDSYVEVKGVVGHPVTLPCTYSTYRGITTTCWGRGQCPSSACQNTLIWTNGHRVTYQKSSRYNLKGHISEGDVSLTIENSVE  100
Rat KIM-1        MVQIQVFISGLLLLLPGSVDSYEVVKGVVGHPVTIPCTYSTRGGITTTCWGRGQCPYSSCQNILIWTNGYQVTYRSSGRYNLKGRISEGDVSLTIENSVD  100
Human HAVcr-1    M-HPQVVILSLILHLADSVAGSVKVGGEAGPSVTLPCHYS--GAVTSMCWNRGSCSLFTCQNGIVWTNGTHVTYRKDTRYKLLGDLSRRDVSLTIENTAV   97
Monkey HAVcr-1   M-HLQVVILSLILHLADSVADSVNVDGVAGLSITLPCRYN--GAITSMCWNRGTCSVFSCPDGIVWTNGTHVTYRKETRYKLLGNLSRRDVSLTIANTAV   97

Mouse TIM-1      SDSGLYCCRVEIPGWFNDQKVTFSLQVKPE---------------------------------------------------IPTRPPTRPTTTRPTATGR  149
Rat KIM-1        SDSGLYCCRVEIPGWFNDQKMTFSLEVKPE---------------------------------------------------IPTSPPTRPTTTRPTTT-R  148
Human HAVcr-1    SDSGVYCCRVEHRGWFNDMKITVSLEIVPPKVTTT-----------------------------------------PIVTTVPTVTTVRTSTTVPTTTTV  156
Monkey HAVcr-1   SDSGIYCCRVKHSGWFNDMKITISLKIGPPRVTTPIVRTVRTSTTVPTTTTLPTTTTLPTTTTLPTTTTLPMTTTLPMTTTLPTTTTVPTTTTLPTTTTL  197

Mouse TIM-1      PTT-----------------------ISTRSTHVPTSIRVSTST----------------------------------------------PPTSTHTWTH  180
Rat KIM-1        PTT-----------------------ISTRSTHVPTSTRVSTST-----------------------------------------------PTPEQTQTH  178
Human HAVcr-1    PTT-----TVPTTMSIPTTTTVPTTMTVSTTTSVPTTTSIPTTTSVPVTTT----------------------------------VSTFVPPMPLPRQNH  218
Monkey HAVcr-1   PTTLPMTTTLPTTRTLPTTTTLPTTMTLPMTTTLPTTTTLPTTTTLPTTTLPTMTLPTTTTLPTMMTLPTTTTLPTTTTLPTTTMVSTFVPPTPLPMQNH  297

Mouse TIM-1      KPEPTTFCP------HETT------AEVTGIPSHT-PTDWNGTVTSSGDT-WSNHTEAIPPGKPQK--NPTKGFYVGICIAALLLLLLVSTVAITRYILM  275
Rat KIM-1        KPEITTFYA------HETT------AEVTETPSYT-PADWNGTVTSSEEA-WNNHTVRIPLRKPQK--NPTKGFYVGMSVAALLLLLLASTVVVTRYIII  273
Human HAVcr-1    EPVATSPSSPQPAETHPTTLQGAIRREPTSSPLYSYTTDGNDTVTESSDGLWNNNQTQLFLEHSLLTANTTKGIYAGVCISVLVLLALLGVIIAKKYFF-  317
Monkey HAVcr-1   EPVATSPSSPQPAETHPVTLLGATRTQPTSSPLYSYTTDGSDTVTESSDGLWNNNQTQLSPEHSPQMVNTTEGIYAGVCISVLVLLAVLGVVIAKKYFF-  396

Mouse TIM-1      KRKSASLSVVAFRVSKIEALQNAAVVHSRAEDNIYIVEDRP---------------
Rat KIM-1        RKKMGSLSFVAFHVSKSRALQNAAIVHPRAEDNIYIIEDRSRGAE-----------
Human HAVcr-1    KKEVQQLS-VSFSSLQIKALQNAVEKEVQAEDNIYIENSLYATD------------
Monkey HAVcr-1   KKEIQQLS-VSFSNHQFKTLQNAVKKEVHAEDNIYIENNLYAMNQDPVVLFESLRP
```

FIG. 5B

```
                              ▽
Mouse TIM-1   M-NQIQVFISGLILLLPGTVDSYVEVKGVVGHPVTLPCTYSTYR-G-ITTTCWGRGQCPSSACQNTLIWTNGHRVTYQKSSRYNLKGHISEQDVSLTIEN
Mouse TIM-2   M-NQIQVFISGLILLLPGAVESHTAVQGLAGHPVTLPCIYSTHL-GGIVPMCWGRGECRHSYCIRSLIWTNGYTVTHQRNSRYQLKGNISEGNVSLTIEN
Mouse a2-11   MFSGLTLNCVLLLLQLLLARSLEDGYKVEVGKNAYLPCSYTLPTSGTLVPMCWGKGFCPWSQCTNELLRTDERNVTYQKSSRYQLKGDLNKGDVSLIIKN

                                         ◆
Mouse TIM-1   SVESDSGLYCCRVEIPGWFNDQKVTFSLQVKPEIPTRPPTRPTTTRPTATGRPTTISTRSTHVPTSIRVSTSTPPTSTHTWTHKPEPTTFCPHETTAEVT
Mouse TIM-2   TVVGDGGPYCCVVEIPGAFHF--VDYMLEVKPEISTSPPTRPT-----ATGRPTTISTRSTHVPTSTRVSTSTSPTPAHTETYKPEATTFYPDQTTAEVT
Mouse a2-11   VTLDDHGTYCCRIQFPGLMNDKKLELKLDIK------------------------------------AAKVTPAQTAHG-----DSTTASPRTLTTERN

Mouse TIM-1   GIPSHTPTSWNGTVTSSGDTWSNHTEAIPPGKPQKNPTKGFYVGICIAA-LLLLLLVSTVAITRYILMKRKSASLSVVAFRVSKIEALQNAAVVHSRAED
Mouse TIM-2   ETLPSTPADWHNTVTSSDDPWDDNTEVIPPQKPQKNLNKGFYVGISIAA-LLILMLLSTMVITRYVVMKRKSESLSFVAFPISKIGASPKKVVERTRCED
Mouse a2-11   GSETQTLVTLHNNNGTKISTWASEIK-----DSGETIRTAIHIGVGVSAGLTLALIIGVLILKWYSCKKKKLSSLSLITLANLPPGGLANAGAVRIRSEE

Mouse TIM-1   NIYIVEDRP-------------------
Mouse TIM-2   QVYIIEDTPYPEEES-------------
Mouse a2-11   NIYTIEENVYEVENSNEYYCYVNSQQPS
```

FIG. 5C

TIM-1 Variants

1 MNQIQVFISGLILLLPGAVDSYVEVKGVVGHPVTLPCTYSTYRGITTTCWGRGQCPSSACQNTLIWTNGHRVTYQKSSRYNLKGHISEGDVSLTIENSVE HBA
1 MNQIQVFISGLILLLPGTVDSYVEVKGVVGHPVTLPCTYSTYRGITTTCWGRGQCPSSACQNTLIWTNGHRVTYQKSSRYNLKGHISEGDVSLTIENSVE BALB/c

100 SDSGLYCCRVEIPGWFNDQKVTFSLQVKPEIPTRPPRRPTTTRPTATGRPTTISTRSTHVPTSTRVSTSTPPTSTHTWTHKPEPTTFC------------ HBA
100 SDSGLYCCRVEIPGWFNDQKVTFSLQVKPEIPTRPPTRPTTTRPTATGRPTTISTRSTHVPTSIRVSTSTPPTSTHTWTHKPEPTTFCPHETTAEVTGIP BALB/c

200 ---PTDWNGTVTSSGDTWSNHTEAIPPGKPQKNPTKGFYVGICIAALLLLLLVSTVAITRYILMKRKSASLSVVAFRVSKIEALQNAAVVHSRAEDNIYI HBA
200 SHTPTDWNGTVTSSGDTWSNHTEAIPPGKPQKNPTKGFYVGICIAALLLLLLVSTVAITRYILMKRKSASLSVVAFRVSKIEALQNAAVVHSRAEDNIYI BALB/c

300 VEDRP HBA
300 VEDRP BALB/c

A2-11/TIM-3 Variants

1 MFSGLTLNCVLLLLQLLLARSLENAYVFEVGKNAYLPCSYTLSTPGALVPMCWGKGFCPWSQCTNELLRTDERNVTYQKSSRYQLKGDLNKGDVSLIIKN HBA
1 MFSGLTLNCVLLLLQLLLARSLEDGYKVEVGKNAYLPCSYTLPTSGTLVPMCWGKGFCPWSQCTNELLRTDERNVTYQKSSRYQLKGDLNKGDVSLIIKN BALB/c

100 VTLDDHGTYCCRIQFPGLMNDKKLELKLDIKAAKVTPAQTAHGDSTTASPRTLTTERNGSETQTLVTLHNNNGTKISTWADEIKDSGETIRTAIHIGVGV HBA
100 VTLDDHGTYCCRIQFPGLMNDKKLELKLDIKAAKVTPAQTAHGDSTTASPRTLTTERNGSETQTLVTLHNNNGTKISTWADEIKDSGETIRTAIHIGVGV BALB/c

200 SAGLTLALIIGVLILKWYSCKKKKLSSLSLITLANLPPGGLANAGAVRIRSEENIYTIEENVYEVENSNEYYCYVNSQQPS HBA
200 SAGLTLALIIGVLILKWYSCKKKKLSSLSLITLANLPPGGLANAGAVRIRSEENIYTIEENVYEVENSNEYYCYVNSQQPS BALB/C

Timeline: RT (two doses): Immunotherapy Surveillance

8 Gy, n=10 per group — on days 0, 3 after RT

RT @ d10,12 → RT+Experimental IT: anti-TIM1 or anti-PDL1 → monitor

RT+Control IT: systemic anti-CTLA4 (i.p.)

RT only control

IT Only Controls

Improved tumor control with specific RT+IT

```
                         SEQUENCE LISTING

<160> NUMBER OF SEQ ID NOS: 61

<210> SEQ ID NO 1
<211> LENGTH: 305
<212> TYPE: PRT
<213> ORGANISM: M. musculus
<220> FEATURE:
<221> NAME/KEY: VARIANT
<222> LOCATION: (1)...(305)
<223> OTHER INFORMATION: TIM-1 BALB/c allele

<400> SEQUENCE: 1

Met Asn Gln Ile Gln Val Phe Ile Ser Gly Leu Ile Leu Leu Leu Pro
 1               5                  10                  15

Gly Thr Val Asp Ser Tyr Val Glu Val Lys Gly Val Val Gly His Pro
            20                  25                  30

Val Thr Leu Pro Cys Thr Tyr Ser Thr Tyr Arg Gly Ile Thr Thr Thr
        35                  40                  45

Cys Trp Gly Arg Gly Gln Cys Pro Ser Ser Ala Cys Gln Asn Thr Leu
    50                  55                  60

Ile Trp Thr Asn Gly His Arg Val Thr Tyr Gln Lys Ser Ser Arg Tyr
65                  70                  75                  80

Asn Leu Lys Gly His Ile Ser Glu Gly Asp Val Ser Leu Thr Ile Glu
                85                  90                  95

Asn Ser Val Glu Ser Asp Ser Gly Leu Tyr Cys Cys Arg Val Glu Ile
            100                 105                 110

Pro Gly Trp Phe Asn Asp Gln Lys Val Thr Phe Ser Leu Gln Val Lys
        115                 120                 125

Pro Glu Ile Pro Thr Arg Pro Pro Thr Arg Pro Thr Thr Thr Arg Pro
    130                 135                 140

Thr Ala Thr Gly Arg Pro Thr Thr Ile Ser Thr Arg Ser Thr His Val
145                 150                 155                 160

Pro Thr Ser Ile Arg Val Ser Thr Ser Thr Pro Pro Thr Ser Thr His
                165                 170                 175

Thr Trp Thr His Lys Pro Glu Pro Thr Thr Phe Cys Pro His Glu Thr
            180                 185                 190

Thr Ala Glu Val Thr Gly Ile Pro Ser His Thr Pro Thr Asp Trp Asn
        195                 200                 205

Gly Thr Val Thr Ser Ser Gly Asp Thr Trp Ser Asn His Thr Glu Ala
```

```
    210                 215                 220

Ile Pro Pro Gly Lys Pro Gln Lys Asn Pro Thr Lys Gly Phe Tyr Val
225                 230                 235                 240

Gly Ile Cys Ile Ala Ala Leu Leu Leu Leu Leu Leu Val Ser Thr Val
                245                 250                 255

Ala Ile Thr Arg Tyr Ile Leu Met Lys Arg Lys Ser Ala Ser Leu Ser
            260                 265                 270

Val Val Ala Phe Arg Val Ser Lys Ile Glu Ala Leu Gln Asn Ala Ala
        275                 280                 285

Val Val His Ser Arg Ala Glu Asp Asn Ile Tyr Ile Val Glu Asp Arg
    290                 295                 300

Pro
305
```

<210> SEQ ID NO 2
<211> LENGTH: 918
<212> TYPE: DNA
<213> ORGANISM: Mus musculus

<400> SEQUENCE: 2

```
atgaatcaga ttcaagtctt catttcaggc ctcatactgc ttctcccagg cactgtggat     60

tcttatgtgg aagtaaaggg ggtagtgggt caccctgtca cacttccatg tacttactca    120

acatatcgtg gaatcacaac gacatgttgg ggccgagggc aatgcccatc ttctgcttgt    180

caaaatacac ttatttggac caatggacat cgtgtcacct atcagaagag cagtcggtac    240

aacttaaagg gcatatttc agaaggagat gtgtccttga cgatagagaa ctctgttgag    300

agtgacagtg gtctgtattg ttgtcgagtg gagattcctg gatggtttaa tgatcagaaa    360

gtgacctttt cattgcaagt taaaccagag attcccacac gtcctccaac aagacccaca    420

actacaaggc ccacagctac aggaagaccc acgactattt caacaagatc cacacatgta    480

ccaacatcaa tcagagtctc tacctccact cctccaacat ctacacacac atggactcac    540

aaaccagaac ccactacatt ttgtccccat gagacaacag ctgaggtgac aggaatccca    600

tcccatactc ctacagactg gaatggcact gtgacatcct caggagatac ctggagtaat    660

cacactgaag caatccctcc agggaagccg cagaaaaacc ctactaaggg cttctatgtt    720

ggcatctgca tcgcagccct gctgctactg ctccttgtga gcaccgtggc tatcaccagg    780

tacatactta tgaaaaggaa gtcagcatct ctaagcgtgg ttgccttccg tgtctctaag    840

attgaagctt tgcagaacgc agcggttgtg cattcccgag ctgaagacaa catctacatt    900

gttgaagata gaccttga                                                  918
```

<210> SEQ ID NO 3
<211> LENGTH: 282
<212> TYPE: PRT
<213> ORGANISM: Mus musculus
<220> FEATURE:
<221> NAME/KEY: VARIANT
<222> LOCATION: (1)...(282)
<223> OTHER INFORMATION: TIM-1, C.D2 ES-HBA and DBA/2J allele

<400> SEQUENCE: 3

```
Met Asn Gln Ile Gln Val Phe Ile Ser Gly Leu Ile Leu Leu Leu Pro
 1               5                  10                  15

Gly Ala Val Asp Ser Tyr Val Glu Val Lys Gly Val Val Gly His Pro
            20                  25                  30

Val Thr Leu Pro Cys Thr Tyr Ser Thr Tyr Arg Gly Ile Thr Thr Thr
        35                  40                  45
```

-continued

```
Cys Trp Gly Arg Gly Gln Cys Pro Ser Ser Ala Cys Gln Asn Thr Leu
    50                  55                  60

Ile Trp Thr Asn Gly His Arg Val Thr Tyr Gln Lys Ser Ser Arg Tyr
65                  70                  75                  80

Asn Leu Lys Gly His Ile Ser Glu Gly Asp Val Ser Leu Thr Ile Glu
                85                  90                  95

Asn Ser Val Glu Ser Asp Ser Gly Leu Tyr Cys Cys Arg Val Glu Ile
            100                 105                 110

Pro Gly Trp Phe Asn Asp Gln Lys Val Thr Phe Ser Leu Gln Val Lys
        115                 120                 125

Pro Glu Ile Pro Thr Arg Pro Pro Arg Arg Pro Thr Thr Thr Arg Pro
    130                 135                 140

Thr Ala Thr Gly Arg Pro Thr Thr Ile Ser Thr Arg Ser Thr His Val
145                 150                 155                 160

Pro Thr Ser Thr Arg Val Ser Thr Ser Thr Pro Pro Thr Ser Thr His
                165                 170                 175

Thr Trp Thr His Lys Pro Asp Trp Asn Gly Thr Val Thr Ser Ser Gly
            180                 185                 190

Asp Thr Trp Ser Asn His Thr Glu Ala Ile Pro Pro Gly Lys Pro Gln
        195                 200                 205

Lys Asn Pro Thr Lys Gly Phe Tyr Val Gly Ile Cys Ile Ala Ala Leu
    210                 215                 220

Leu Leu Leu Leu Leu Val Ser Thr Val Ala Ile Thr Arg Tyr Ile Leu
225                 230                 235                 240

Met Lys Arg Lys Ser Ala Ser Leu Ser Val Val Ala Phe Arg Val Ser
                245                 250                 255

Lys Ile Glu Ala Leu Gln Asn Ala Ala Val Val His Ser Arg Ala Glu
            260                 265                 270

Asp Asn Ile Tyr Ile Val Glu Asp Arg Pro
        275                 280
```

<210> SEQ ID NO 4
<211> LENGTH: 849
<212> TYPE: DNA
<213> ORGANISM: Mus musculus

<400> SEQUENCE: 4

```
atgaatcaga ttcaagtctt catttcaggc ctcatactgc ttctcccagg cgctgtggat      60

tcttatgtgg aagtaaaggg ggtggtgggt caccctgtca cacttccatg tacttactca     120

acatatcgtg gaatcacaac gacatgttgg ggccgagggc aatgcccatc ttctgcttgt     180

caaaatacac ttatttggac caatggacat cgtgtcacct atcagaagag cagtcggtac     240

aacttaaagg ggcatatttc agaaggagat gtgtccttga cgatagagaa ctctgttgag     300

agtgacagtg gtctgtattg ttgtcgagtg gagattcctg gatggtttaa tgatcagaaa     360

gtgacctttt cattgcaagt taaaccagag attcccacac gtcctccaag aagacccaca     420

actacaaggc ccacagctac aggaagaccc acgactattt caacaagatc cacacatgta     480

ccaacatcaa ccagagtctc tacctccact cctccaacat ctacacacac atggactcac     540

aaaccagact ggaatggcac tgtgacatcc tcaggagata cctggagtaa tcacactgaa     600

gcaatccctc cagggaagcc gcagaaaaac cctactaagg gcttctatgt tggcatctgc     660

atcgcagccc tgctgctact gctccttgtg agcaccgtgg ctatcaccag gtacatactt     720

atgaaaagga agtcagcatc tctaagcgtg gttgccttcc gtgtctctaa gattgaagct     780
```

ttgcagaacg cagcggttgt gcattcccga gctgaagaca acatctacat tgttgaagat 840
agaccttga 849

<210> SEQ ID NO 5
<211> LENGTH: 305
<212> TYPE: PRT
<213> ORGANISM: Mus musculus
<220> FEATURE:
<221> NAME/KEY: VARIANT
<222> LOCATION: (1)...(305)
<223> OTHER INFORMATION: TIM-2 BALB/c allele

<400> SEQUENCE: 5

Met Asn Gln Ile Gln Val Phe Ile Ser Gly Leu Ile Leu Leu Leu Pro
1 5 10 15

Gly Ala Val Glu Ser His Thr Ala Val Gln Gly Leu Ala Gly His Pro
20 25 30

Val Thr Leu Pro Cys Ile Tyr Ser Thr His Leu Gly Gly Ile Val Pro
35 40 45

Met Cys Trp Gly Leu Gly Glu Cys Arg His Ser Tyr Cys Ile Arg Ser
50 55 60

Leu Ile Trp Thr Asn Gly Tyr Thr Val Thr His Gln Arg Asn Ser Arg
65 70 75 80

Tyr Gln Leu Lys Gly Asn Ile Ser Glu Gly Asn Val Ser Leu Thr Ile
85 90 95

Glu Asn Thr Val Val Gly Asp Gly Gly Pro Tyr Cys Cys Val Val Glu
100 105 110

Ile Pro Gly Ala Phe His Phe Val Asp Tyr Met Leu Glu Val Lys Pro
115 120 125

Glu Ile Ser Thr Ser Pro Pro Thr Arg Pro Thr Ala Thr Gly Arg Pro
130 135 140

Thr Thr Ile Ser Thr Arg Ser Thr His Val Pro Thr Ser Thr Arg Val
145 150 155 160

Ser Thr Ser Thr Ser Pro Thr Pro Ala His Thr Glu Thr Tyr Lys Pro
165 170 175

Glu Ala Thr Thr Phe Tyr Pro Asp Gln Thr Thr Ala Glu Val Thr Glu
180 185 190

Thr Leu Pro Ser Thr Pro Ala Asp Trp His Asn Thr Val Thr Ser Ser
195 200 205

Asp Asp Pro Trp Asp Asp Asn Thr Glu Val Ile Pro Pro Gln Lys Pro
210 215 220

Gln Lys Asn Leu Asn Lys Gly Phe Tyr Val Gly Ile Ser Ile Ala Ala
225 230 235 240

Leu Leu Ile Leu Met Leu Leu Ser Thr Met Val Ile Thr Arg Tyr Val
245 250 255

Val Met Lys Arg Lys Ser Glu Ser Leu Ser Phe Val Ala Phe Pro Ile
260 265 270

Ser Lys Ile Gly Ala Ser Pro Lys Lys Val Val Glu Arg Thr Arg Cys
275 280 285

Glu Asp Gln Val Tyr Ile Ile Glu Asp Thr Pro Tyr Pro Glu Glu Glu
290 295 300

Ser
305

<210> SEQ ID NO 6
<211> LENGTH: 958
<212> TYPE: DNA

-continued

<213> ORGANISM: Mus musculus

<400> SEQUENCE: 6

```
aagctacggc tctctcctaa ctggtcgtac catgaatcag attcaagtct tcatttcagg      60

cctcatactg cttctcccag gtgccgtgga gtctcataca gcagtgcagg ggctggcggg     120

tcaccctgtc acacttccat gtatttattc gacacacctt ggtggaatcg ttcctatgtg     180

ttggggccta ggggaatgcc gccattctta ttgtatacgg tcacttatct ggaccaatgg     240

atatacggtc acacatcaga ggaacagtcg ataccagcta aaggggaata tttcagaagg     300

aaatgtgtcc ttgaccatag agaacactgt tgtgggtgat ggtggtccct attgctgtgt     360

agtggagata cctggagcgt tccattttgt ggactatatg ttggaagtta aaccagaaat     420

ttccacgagt ccaccaacaa ggcccacagc tacaggaaga cccacaacta tttcaacaag     480

atccacacat gtaccaacat caaccagagt ctctacctct acttctccaa caccagcaca     540

cacagagacc tacaaaccag aggccactac attttatcca gatcagacta cagctgaggt     600

gacagaaacc ttaccctcta ctcctgcaga ctggcataac actgtgacat cctcagatga     660

cccttgggat gataacactg aagtaatccc tccacagaag ccacagaaaa acctgaataa     720

gggcttctat gttggcatct ccattgcagc cctgctgata ttgatgcttc tgagcaccat     780

ggttatcacc aggtacgtgg ttatgaaaag gaagtcagaa tctctgagct ttgttgcctt     840

ccctatctct aagattggag cttcccccaa aaaagtggtc gaacggacca gatgtgaaga     900

ccaggtctac attattgaag acactcctta ccctgaagaa gagtcctagt gcctctac       958
```

<210> SEQ ID NO 7
<211> LENGTH: 305
<212> TYPE: PRT
<213> ORGANISM: Mus musculus
<220> FEATURE:
<221> NAME/KEY: VARIANT
<222> LOCATION: (1)...(305)
<223> OTHER INFORMATION: TIM-2, C.D2 ES-HBA and DBA/2J allele

<400> SEQUENCE: 7

```
Met Asn Gln Ile Gln Val Phe Ile Ser Gly Leu Ile Leu Leu Leu Pro
 1               5                  10                  15

Gly Ala Val Glu Ser His Thr Ala Val Gln Gly Leu Ala Gly His Pro
            20                  25                  30

Val Thr Leu Pro Cys Ile Tyr Ser Thr His Leu Gly Gly Ile Val Pro
        35                  40                  45

Met Cys Trp Gly Leu Gly Glu Cys Arg His Ser Tyr Cys Ile Arg Ser
    50                  55                  60

Leu Ile Trp Thr Asn Gly Tyr Thr Val Thr His Gln Arg Asn Ser Arg
65                  70                  75                  80

Tyr Gln Leu Lys Gly Asn Ile Ser Glu Gly Asn Val Ser Leu Thr Ile
                85                  90                  95

Glu Asn Thr Val Val Gly Asp Gly Gly Pro Tyr Cys Cys Val Val Glu
            100                 105                 110

Ile Pro Gly Ala Phe His Phe Val Asp Tyr Met Leu Glu Val Lys Pro
        115                 120                 125

Glu Ile Ser Thr Ser Pro Pro Thr Arg Pro Thr Ala Thr Gly Arg Pro
    130                 135                 140

Thr Thr Ile Ser Thr Arg Ser Thr His Val Pro Thr Ser Thr Arg Val
145                 150                 155                 160

Ser Thr Ser Thr Ser Pro Thr Pro Ala His Thr Glu Thr Tyr Lys Pro
                165                 170                 175
```

```
Glu Ala Thr Thr Phe Tyr Pro Asp Gln Thr Thr Ala Glu Val Thr Glu
            180                 185                 190

Thr Leu Pro Ser Thr Pro Ala Asp Trp His Asn Thr Val Thr Ser Ser
        195                 200                 205

Asp Asp Pro Trp Asp Asp Asn Thr Glu Val Ile Pro Pro Gln Lys Pro
    210                 215                 220

Gln Lys Asn Leu Asn Lys Gly Phe Tyr Val Gly Ile Ser Ile Ala Ala
225                 230                 235                 240

Leu Leu Ile Leu Met Leu Leu Ser Thr Met Val Ile Thr Arg Tyr Val
                245                 250                 255

Val Met Lys Arg Lys Ser Glu Ser Leu Ser Phe Val Ala Phe Pro Ile
            260                 265                 270

Ser Lys Ile Gly Ala Ser Pro Lys Lys Val Val Glu Arg Thr Arg Cys
        275                 280                 285

Glu Asp Gln Val Tyr Ile Ile Glu Asp Thr Pro Tyr Pro Glu Glu Glu
    290                 295                 300

Ser
305


<210> SEQ ID NO 8
<211> LENGTH: 958
<212> TYPE: DNA
<213> ORGANISM: Mus musculus

<400> SEQUENCE: 8

aagctacggc tctctcctaa ctggtcgtac catgaatcag attcaagtct tcatttcagg     60

cctcatactg cttctcccag gtgccgtgga gtctcataca gcagtgcagg ggctggcggg    120

tcaccctgtc acacttccat gtatttattc gacacacctt ggtggaatcg ttcctatgtg    180

ttggggccta ggggaatgcc gccattctta ttgtatacgg tcacttatct ggaccaatgg    240

atatacggtc acacatcaga ggaacagtcg ataccagcta aaggggaata tttcagaagg    300

aaatgtgtcc ttgaccatag agaacactgt tgtgggtgat ggtggtccct attgctgtgt    360

agtggagata cctggagcgt tccattttgt ggactatatg ttggaagtta aaccagaaat    420

ttccacgagt ccaccaacaa ggcccacagc tacaggaaga cccacaacta tttcaacaag    480

atccacacat gtaccaacat caaccagagt ctctacctct acttctccaa caccagcaca    540

cacagagacc tacaaaccag aggccactac attttatcca gatcagacta cagctgaggt    600

gacagaaacc ttaccctcta ctcctgcaga ctggcataac actgtgacat cctcagatga    660

cccttgggat gataacactg aagtaatccc tccacagaag ccacagaaaa acctgaataa    720

gggcttctat gttggcatct ccattgcagc cctgctgata ttgatgcttc tgagcaccat    780

ggttatcacc aggtacgtgg ttatgaaaag gaagtcagaa tctctgagct tcgttgcctt    840

ccctatctct aagattggag cttcccccaa aaaagtggtc gaacggacca gatgtgaaga    900

ccaggtctac attattgaag acactcctta ccccgaagaa gagtcctagt gcctctac      958


<210> SEQ ID NO 9
<211> LENGTH: 281
<212> TYPE: PRT
<213> ORGANISM: Mus musculus
<220> FEATURE:
<221> NAME/KEY: VARIANT
<222> LOCATION: (1)...(281)
<223> OTHER INFORMATION: TIM-3 BALB/c allele

<400> SEQUENCE: 9
```

```
Met Phe Ser Gly Leu Thr Leu Asn Cys Val Leu Leu Leu Leu Gln Leu
 1               5                  10                  15

Leu Leu Ala Arg Ser Leu Glu Asp Gly Tyr Lys Val Glu Val Gly Lys
            20                  25                  30

Asn Ala Tyr Leu Pro Cys Ser Tyr Thr Leu Pro Thr Ser Gly Thr Leu
        35                  40                  45

Val Pro Met Cys Trp Gly Lys Gly Phe Cys Pro Trp Ser Gln Cys Thr
    50                  55                  60

Asn Glu Leu Leu Arg Thr Asp Glu Arg Asn Val Thr Tyr Gln Lys Ser
65                  70                  75                  80

Ser Arg Tyr Gln Leu Lys Gly Asp Leu Asn Lys Gly Asp Val Ser Leu
                85                  90                  95

Ile Ile Lys Asn Val Thr Leu Asp Asp His Gly Thr Tyr Cys Cys Arg
            100                 105                 110

Ile Gln Phe Pro Gly Leu Met Asn Asp Lys Lys Leu Glu Leu Lys Leu
        115                 120                 125

Asp Ile Lys Ala Ala Lys Val Thr Pro Ala Gln Thr Ala His Gly Asp
    130                 135                 140

Ser Thr Thr Ala Ser Pro Arg Thr Leu Thr Thr Glu Arg Asn Gly Ser
145                 150                 155                 160

Glu Thr Gln Thr Leu Val Thr Leu His Asn Asn Asn Gly Thr Lys Ile
                165                 170                 175

Ser Thr Trp Ala Asp Glu Ile Lys Asp Ser Gly Glu Thr Ile Arg Thr
            180                 185                 190

Ala Ile His Ile Gly Val Gly Val Ser Ala Gly Leu Thr Leu Ala Leu
        195                 200                 205

Ile Ile Gly Val Leu Ile Leu Lys Trp Tyr Ser Cys Lys Lys Lys Lys
    210                 215                 220

Leu Ser Ser Leu Ser Leu Ile Thr Leu Ala Asn Leu Pro Pro Gly Gly
225                 230                 235                 240

Leu Ala Asn Ala Gly Ala Val Arg Ile Arg Ser Glu Glu Asn Ile Tyr
                245                 250                 255

Thr Ile Glu Glu Asn Val Tyr Glu Val Glu Asn Ser Asn Glu Tyr Tyr
            260                 265                 270

Cys Tyr Val Asn Ser Gln Gln Pro Ser
        275                 280
```

<210> SEQ ID NO 10
<211> LENGTH: 2725
<212> TYPE: DNA
<213> ORGANISM: Mus musculus

<400> SEQUENCE: 10

```
ttttaaccga ggagctaaag ctatccctac acagagctgt ccttggattt cccctgccaa     60

gtactcatgt tttcaggtct taccctcaac tgtgtcctgc tgctgctgca actactactt    120

gcaaggtcat tggaagatgg ttataaggtt gaggttggta aaaatgccta tctgccctgc    180

agttacactc tacctacatc tgggacactt gtgcctatgt gctggggcaa gggattctgt    240

ccttggtcac agtgtaccaa tgagttgctc agaactgatg aaagaaatgt gacatatcag    300

aaatccagca gataccagct aaagggcgat ctcaacaaag gagatgtgtc tctgatcata    360

aagaatgtga ctctggatga ccatgggacc tactgctgca ggatacagtt ccctggtctt    420

atgaatgata aaaaattaga actgaaatta gacatcaaag cagccaaggt cactccagct    480

cagactgccc atggggactc tactacagct tctccaagaa ccctaaccac ggagagaaat    540
```

-continued

```
ggttcagaga cacagacact ggtgaccctc cataataaca atggaacaaa aatttccaca    600
tgggctgatg aaattaagga ctctggagaa acgatcagaa ctgctatcca cattggagtg    660
ggagtctctg ctgggttgac cctggcactt atcattggtg tcttaatcct taaatggtat    720
tcctgtaaga aaaagaagtt atcgagtttg agccttatta cactggccaa cttgcctcca    780
ggagggttgg caaatgcagg agcagtcagg attcgctctg aggaaaatat ctacaccatc    840
gaggagaacg tatatgaagt ggagaattca aatgagtact actgctacgt caacagccag    900
cagccatcct gaccgcctct ggactgccac ttttaaaggc tcgccttcat ttctgacttt    960
ggtatttccc tttttgaaaa ctatgtgata tgtcacttgg caacctcatt ggaggttctg   1020
accacagcca ctgagaaaag agttccagtt ttctggggat aattaactca caaggggatt   1080
cgactgtaac tcatgctaca ttgaaatgct ccattttatc cctgagtttc agggatcgga   1140
tctcccactc cagagacttc aatcatgcgt gttgaagctc actcgtgctt tcatacatta   1200
ggaatggtta gtgtgatgtc tttgagacat agaggtttgt ggtatatccg caaagctcct   1260
gaacaggtag ggggaataaa gggctaagat aggaaggtgc ggttctttgt tgatgttgaa   1320
aatctaaaga agttggtagc ttttctagag atttctgacc ttgaaagatt aagaaaaagc   1380
caggtggcat atgcttaaca cgatataact tgggaacctt aggcaggagg gtgataagtt   1440
caaggtcagc cagggctatg ctggtaagac tgtctcaaaa tccaaagacg aaaataaaca   1500
tagagacagc aggaggctgg agatgaggct cggacagtga ggtgcatttt gtacaagcac   1560
gaggaatcta tatttgatcg tagaccccac atgaaaaagc taggcctggt agagcatgct   1620
tgtagactca agagatggag aggtaaaggc acaacagatc ccggggctt gcgtgcagtc   1680
agcttagcct aggtgctgag ttccaagtcc acaagagtcc ctgtctcaaa gtaagatgga   1740
ctgagtatct ggcgaatgtc catgggggtt gtcctctgct ctcagaagag acatgcacat   1800
gaacctgcac acacacacac acacacacac acacacacac acacacacac acacatgaaa   1860
tgaaggttct ctctgtgcct gctacctctc tataacatgt atctctacag gactctcctc   1920
tgcctctgtt aagacatgag tgggagcatg gcagagcagt ccagtaatta attccagcac   1980
tcagaaggct ggagcagaag cgtggagagt tcaggagcac tgtgcccaac actgccagac   2040
tcttcttaca caagaaaaag gttacccgca agcagcctgc tgtctgtaaa aggaaaccct   2100
gcgaaaggca aactttgact gttgtgtgct caaggggaac tgactcagac aacttctcca   2160
ttcctggagg aaactggagc tgtttctgac agaagaacaa ccggtgactg ggacatacga   2220
aggcagagct cttgcagcaa tctatatagt cagcaaaata ttctttggga ggacagtcgt   2280
caccaaattg atttccaagc cggtggacct cagtttcatc tggcttacag ctgcctgccc   2340
agtgcccttg atctgtgctg gctcccatct ataacagaat caaattaaat agaccccgag   2400
tgaaaatatt aagtgagcag aaaggtagct ttgttcaaag atttttttgc attggggagc   2460
aactgtgtac atcagaggac atctgttagt gaggacacca aaacctgtgg taccgttttt   2520
tcatgtatga attttgttgt ttaggttgct tctagctagc tgtggaggtc ctggctttct   2580
taggtgggta tggaagggag accatctaac aaaatccatt agagataaca gctctcatgc   2640
agaagggaaa actaatctca aatgttttaa agtaataaaa ctgtactggc aaagtacttt   2700
gagcatattt aaaaaaaaaa aaaaa                                         2725
```

<210> SEQ ID NO 11
<211> LENGTH: 281
<212> TYPE: PRT
<213> ORGANISM: Mus musculus
<220> FEATURE:

<221> NAME/KEY: VARIANT
<222> LOCATION: (1)...(281)
<223> OTHER INFORMATION: TIM-3, C.D2 ES-HBA and DBA/2J allele

<400> SEQUENCE: 11

```
Met Phe Ser Gly Leu Thr Leu Asn Cys Val Leu Leu Leu Leu Gln Leu
 1               5                  10                  15

Leu Leu Ala Arg Ser Leu Glu Asn Ala Tyr Val Phe Glu Val Gly Lys
            20                  25                  30

Asn Ala Tyr Leu Pro Cys Ser Tyr Thr Leu Ser Thr Pro Gly Ala Leu
        35                  40                  45

Val Pro Met Cys Trp Gly Lys Gly Phe Cys Pro Trp Ser Gln Cys Thr
    50                  55                  60

Asn Glu Leu Leu Arg Thr Asp Glu Arg Asn Val Thr Tyr Gln Lys Ser
65                  70                  75                  80

Ser Arg Tyr Gln Leu Lys Gly Asp Leu Asn Lys Gly Asp Val Ser Leu
                85                  90                  95

Ile Ile Lys Asn Val Thr Leu Asp Asp His Gly Thr Tyr Cys Cys Arg
            100                 105                 110

Ile Gln Phe Pro Gly Leu Met Asn Asp Lys Lys Leu Glu Leu Lys Leu
        115                 120                 125

Asp Ile Lys Ala Ala Lys Val Thr Pro Ala Gln Thr Ala His Gly Asp
    130                 135                 140

Ser Thr Thr Ala Ser Pro Arg Thr Leu Thr Thr Glu Arg Asn Gly Ser
145                 150                 155                 160

Glu Thr Gln Thr Leu Val Thr Leu His Asn Asn Asn Gly Thr Lys Ile
                165                 170                 175

Ser Thr Trp Ala Asp Glu Ile Lys Asp Ser Gly Glu Thr Ile Arg Thr
            180                 185                 190

Ala Ile His Ile Gly Val Gly Val Ser Ala Gly Leu Thr Leu Ala Leu
        195                 200                 205

Ile Ile Gly Val Leu Ile Leu Lys Trp Tyr Ser Cys Lys Lys Lys Lys
    210                 215                 220

Leu Ser Ser Leu Ser Leu Ile Thr Leu Ala Asn Leu Pro Pro Gly Gly
225                 230                 235                 240

Leu Ala Asn Ala Gly Ala Val Arg Ile Arg Ser Glu Glu Asn Ile Tyr
                245                 250                 255

Thr Ile Glu Glu Asn Val Tyr Glu Val Glu Asn Ser Asn Glu Tyr Tyr
            260                 265                 270

Cys Tyr Val Asn Ser Gln Gln Pro Ser
        275                 280
```

<210> SEQ ID NO 12
<211> LENGTH: 862
<212> TYPE: DNA
<213> ORGANISM: Mus musculus

<400> SEQUENCE: 12

```
cccctcccaa gtactcatgt tttcaggtct taccctcaac tgtgtcctgc tgctgctgca     60

actactactt gcaaggtcat tggaaaatgc ttatgtgttt gaggttggta agaatgccta    120

tctgccctgc agttacactc tatctacacc tggggcactt gtgcctatgt gctggggcaa    180

gggattctgt ccttggtcac agtgtaccaa cgagttgctc agaactgatg aaagaaatgt    240

gacatatcag aaatccagca gataccagct aaagggcgat ctcaacaaag gagacgtgtc    300

tctgatcata aagaatgtga ctctggatga ccatgggacc tactgctgca ggatacagtt    360
```

-continued

```
ccctggtctt atgaatgata aaaaattaga actgaaatta gacatcaaag cagccaaggt    420

cactccagct cagactgccc atggggactc tactacagct tctccaagaa ccctaaccac    480

ggagagaaat ggttcagaga cacagacact ggtgaccctc cataataaca atggaacaaa    540

aatttccaca tgggctgatg aaattaagga ctctggagaa acgatcagaa ctgctatcca    600

cattggagtg ggagtctctg ctgggttgac cctggcactt atcattggtg tcttaatcct    660

taaatggtat tcctgtaaga aaaagaagtt atcgagtttg agccttatta cactggccaa    720

cttgcctcca ggagggttgg caaatgcagg agcagtcagg attcgctctg aggaaaatat    780

ctacaccatc gaggagaacg tatatgaagt ggagaattca aatgagtact actgctacgt    840

caacagccag cagccatcct ga                                             862
```

<210> SEQ ID NO 13
<211> LENGTH: 345
<212> TYPE: PRT
<213> ORGANISM: Mus musculus
<220> FEATURE:
<221> NAME/KEY: VARIANT
<222> LOCATION: (1)...(345)
<223> OTHER INFORMATION: TIM-4, BALB/c allele

<400> SEQUENCE: 13

```
Met Ser Lys Gly Leu Leu Leu Leu Trp Leu Val Thr Glu Leu Trp Trp
 1               5                  10                  15

Leu Tyr Leu Ser Lys Ser Pro Ala Ala Ser Glu Asp Thr Ile Ile Gly
            20                  25                  30

Phe Leu Gly Gln Pro Val Thr Leu Pro Cys His Tyr Leu Ser Trp Ser
        35                  40                  45

Gln Ser Arg Asn Ser Met Cys Trp Gly Lys Gly Ser Cys Pro Asn Ser
    50                  55                  60

Lys Cys Asn Ala Glu Leu Leu Arg Thr Asp Gly Thr Arg Ile Ile Ser
65                  70                  75                  80

Arg Lys Ser Thr Lys Tyr Thr Leu Leu Gly Lys Val Gln Phe Gly Glu
                85                  90                  95

Val Ser Leu Thr Ile Ser Asn Thr Asn Arg Gly Asp Ser Gly Val Tyr
            100                 105                 110

Cys Cys Arg Ile Glu Val Pro Gly Trp Phe Asn Asp Val Lys Lys Asn
        115                 120                 125

Val Arg Leu Glu Leu Arg Arg Ala Thr Thr Thr Lys Lys Pro Thr Thr
    130                 135                 140

Thr Thr Arg Pro Thr Thr Thr Pro Tyr Val Thr Thr Thr Thr Pro Glu
145                 150                 155                 160

Leu Leu Pro Thr Thr Val Met Thr Thr Ser Val Leu Pro Thr Thr Thr
                165                 170                 175

Pro Pro Gln Thr Leu Ala Thr Thr Ala Phe Ser Thr Ala Val Thr Thr
            180                 185                 190

Cys Pro Ser Thr Thr Pro Gly Ser Phe Ser Gln Glu Thr Thr Lys Gly
        195                 200                 205

Ser Ala Ile Thr Thr Glu Ser Glu Thr Leu Pro Ala Ser Asn His Ser
    210                 215                 220

Gln Arg Ser Met Met Thr Ile Ser Thr Asp Ile Ala Val Leu Arg Pro
225                 230                 235                 240

Thr Gly Ser Asn Pro Gly Ile Leu Pro Ser Thr Ser Gln Leu Thr Thr
                245                 250                 255

Gln Lys Thr Thr Leu Thr Thr Ser Glu Ser Leu Gln Lys Thr Thr Lys
            260                 265                 270
```

```
Ser His Gln Ile Asn Ser Arg Gln Thr Ile Leu Ile Ile Ala Cys Cys
        275                 280                 285

Val Gly Phe Val Leu Met Val Leu Leu Phe Leu Ala Phe Leu Leu Arg
    290                 295                 300

Gly Lys Val Thr Gly Ala Asn Cys Leu Gln Arg His Lys Arg Pro Asp
305                 310                 315                 320

Asn Thr Glu Val Ser Asp Ser Phe Leu Asn Asp Ile Ser His Gly Arg
                325                 330                 335

Asp Asp Glu Asp Gly Ile Phe Thr Leu
            340                 345


<210> SEQ ID NO 14
<211> LENGTH: 1032
<212> TYPE: DNA
<213> ORGANISM: Mus musculus

<400> SEQUENCE: 14

atgtccaagg ggcttctcct cctctggctg gtgacggagc tctggtggct ttatctgaca      60

ccagctgcct cagaggatac aataataggg tttttgggcc agccggtgac tttgccttgt     120

cattacctct cgtggtccca gagccgcaac agtatgtgct ggggcaaagg ttcatgtccc     180

aattccaagt gcaatgcaga gcttctccgt acagatggaa caagaatcat ctccaggaag     240

tcaacaaaat atacactttt ggggaaggtc cagtttggtg aagtgtcctt gaccatctca     300

aacaccaatc gaggtgacag tggggtgtac tgctgccgta tagaggtgcc tggctggttc     360

aatgatgtca agaagaatgt gcgcttggag ctgaggagag ccacaacaac caaaaaacca     420

acaacaacca cccggccaac caccacccct tatgtaacca ccaccacccc agagctgctt     480

ccaacaacag tcatgaccac atctgttctt ccaaccacca caccacccca gacactagcc     540

accactgcct tcagtacagc agtgaccacg tgcccctcaa caacacctgg ctccttctca     600

caagaaacca caaaagggtc cgccatcact acagaatcag aaactctgcc tgcatccaat     660

cactctcaaa gaagcatgat gaccatatct acagacatag ccgtactcag gcccacaggc     720

tctaaccctg ggattctccc atccacttca cagctgacga cacagaaaac aacattaaca     780

acaagtgagt ctttgcagaa gacaactaaa tcacatcaga tcaacagcag acagaccatc     840

ttgatcattg cctgctgtgt gggatttgtg ctaatggtgt tattgtttct ggcgtttctc     900

cttcgaggga aagtcacagg agccaactgt ttgcagagac acaagaggcc agacaacact     960

gaagatagtg acagcgtcct caatgacatg tcacacggga gggatgatga agacgggatc    1020

ttcactctct ga                                                        1032


<210> SEQ ID NO 15
<211> LENGTH: 345
<212> TYPE: PRT
<213> ORGANISM: Mus musculus
<220> FEATURE:
<221> NAME/KEY: VARIANT
<222> LOCATION: (1)...(345)
<223> OTHER INFORMATION: C.D2 ES-HBA and DBA/2J allele

<400> SEQUENCE: 15

Met Ser Lys Gly Leu Leu Leu Leu Trp Leu Val Met Glu Leu Trp Trp
 1               5                  10                  15

Leu Tyr Leu Ser Lys Ser Pro Ala Ala Ser Glu Asp Thr Ile Ile Gly
            20                  25                  30

Phe Leu Gly Gln Pro Val Thr Leu Pro Cys His Tyr Leu Ser Trp Ser
        35                  40                  45
```

-continued

```
Gln Ser Arg Asn Ser Met Cys Trp Gly Lys Gly Ser Cys Pro Asn Ser
    50                  55                  60

Lys Cys Asn Ala Glu Leu Leu Arg Thr Asp Gly Thr Arg Ile Ile Ser
65                  70                  75                  80

Arg Lys Ser Thr Lys Tyr Thr Leu Leu Gly Lys Val Gln Phe Gly Glu
                85                  90                  95

Val Ser Leu Thr Ile Ser Asn Thr Asn Arg Gly Asp Ser Gly Val Tyr
            100                 105                 110

Cys Cys Arg Ile Glu Val Pro Gly Trp Phe Asn Asp Val Lys Lys Asn
        115                 120                 125

Val Arg Leu Glu Leu Arg Arg Ala Thr Thr Thr Lys Lys Pro Thr Thr
    130                 135                 140

Thr Thr Arg Pro Thr Thr Thr Pro Tyr Val Thr Thr Thr Thr Pro Glu
145                 150                 155                 160

Leu Leu Pro Thr Thr Val Met Thr Thr Ser Val Leu Pro Thr Thr Thr
                165                 170                 175

Pro Pro Gln Thr Leu Ala Thr Thr Ala Phe Ser Thr Ala Val Thr Thr
            180                 185                 190

Cys Pro Ser Thr Thr Pro Gly Ser Phe Ser Gln Glu Thr Thr Lys Gly
        195                 200                 205

Ser Ala Phe Thr Thr Glu Ser Glu Thr Leu Pro Ala Ser Asn His Ser
    210                 215                 220

Gln Arg Ser Met Met Thr Ile Ser Thr Asp Ile Ala Val Leu Arg Pro
225                 230                 235                 240

Thr Gly Ser Asn Pro Gly Ile Leu Pro Ser Thr Ser Gln Leu Thr Thr
                245                 250                 255

Gln Lys Thr Thr Leu Thr Thr Ser Glu Ser Leu Gln Lys Thr Thr Lys
            260                 265                 270

Ser His Gln Ile Asn Ser Arg Gln Thr Ile Leu Ile Ile Ala Cys Cys
        275                 280                 285

Val Gly Phe Val Leu Met Val Leu Leu Phe Leu Ala Phe Leu Leu Arg
    290                 295                 300

Gly Lys Val Thr Gly Ala Asn Cys Leu Gln Arg His Lys Arg Pro Asp
305                 310                 315                 320

Asn Thr Glu Val Ser Asp Ser Phe Leu Asn Asp Ile Ser His Gly Arg
                325                 330                 335

Asp Asp Glu Asp Gly Ile Phe Thr Leu
            340                 345


<210> SEQ ID NO 16
<211> LENGTH: 1032
<212> TYPE: DNA
<213> ORGANISM: Mus musculus

<400> SEQUENCE: 16

atgtccaagg ggcttctcct cctctggctg gtgatggagc tctggtggct ttatctgaca     60

ccagctgcct cagaggatac aataataggg tttttgggcc agccggtgac tttgccttgt    120

cattacctct cgtggtccca gagccgcaac agtatgtgct ggggcaaagg ttcatgtccc    180

aattccaagt gcaatgcaga gcttctccgt acagatggaa caagaatcat ctccaggaag    240

tcaacaaaat atacactttt ggggaaggtc cagtttggtg aagtgtcctt gaccatctca    300

aacaccaatc gaggtgacag tggggtgtac tgctgccgta tagaggtgcc tggctggttc    360

aatgatgtca agaagaatgt gcgcttggag ctgaggagag ccacaacaac caaaaaacca    420
```

```
acaacaacca cccggccaac caccacccct tatgtaacca ccaccacccc agagctgctt    480

ccaacaacag tcatgaccac atctgttctt ccaaccacca caccacccca gacactagcc    540

accactgcct tcagtacagc agtgaccacg tgcccctcaa caacacctgg ctccttctca    600

caagaaacca caaaagggtc cgccttcact acagaatcag aaactctgcc tgcatccaat    660

cactctcaaa gaagcatgat gaccatatct acagacatag ccgtactcag gcccacaggc    720

tctaaccctg ggattctccc atccacttca cagctgacga cacagaaaac aacattaaca    780

acaagtgagt ctttgcagaa gacaactaaa tcacatcaga tcaacagcag acagaccatc    840

ttgatcattg cctgctgtgt gggatttgtg ctaatggtgt tattgtttct ggcgtttctc    900

cttcgaggga aagtcacagg agccaactgt ttgcagagac acaagaggcc agacaacact    960

gaagatagtg acagcgtcct caatgacatg tcacacggga gggatgatga agacgggatc   1020

ttcactctct ga                                                       1032


<210> SEQ ID NO 17
<211> LENGTH: 359
<212> TYPE: PRT
<213> ORGANISM: H. sapiens
<220> FEATURE:
<221> NAME/KEY: VARIANT
<222> LOCATION: (1)...(360)
<223> OTHER INFORMATION: TIM-1 allele 1

<400> SEQUENCE: 17

Met His Pro Gln Val Val Ile Leu Ser Leu Ile Leu His Leu Ala Asp
 1               5                  10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
    50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
        115                 120                 125

Val Thr Thr Thr Pro Ile Val Thr Thr Val Pro Thr Val Thr Thr Val
    130                 135                 140

Arg Thr Ser Thr Thr Val Pro Thr Thr Thr Thr Val Pro Thr Thr Thr
145                 150                 155                 160

Val Pro Thr Thr Met Ser Ile Pro Thr Thr Thr Thr Val Pro Thr Thr
                165                 170                 175

Met Thr Val Ser Thr Thr Thr Ser Val Pro Thr Thr Thr Ser Ile Pro
            180                 185                 190

Thr Thr Thr Ser Val Pro Val Thr Thr Thr Val Ser Thr Phe Val Pro
        195                 200                 205

Pro Met Pro Leu Pro Arg Gln Asn His Glu Pro Val Ala Thr Ser Pro
    210                 215                 220

Ser Ser Pro Gln Pro Ala Glu Thr His Pro Thr Thr Leu Gln Gly Ala
225                 230                 235                 240

Ile Arg Arg Glu Pro Thr Ser Ser Pro Leu Tyr Ser Tyr Thr Thr Asp
```

-continued

```
                245                 250                 255

Gly Asn Asp Thr Val Thr Glu Ser Ser Asp Gly Leu Trp Asn Asn Asn
            260                 265                 270

Gln Thr Gln Leu Phe Leu Glu His Ser Leu Leu Thr Ala Asn Thr Thr
        275                 280                 285

Lys Gly Ile Tyr Ala Gly Val Cys Ile Ser Val Leu Val Leu Leu Ala
    290                 295                 300

Leu Leu Gly Val Ile Ile Ala Lys Lys Tyr Phe Phe Lys Lys Glu Val
305                 310                 315                 320

Gln Gln Leu Ser Val Ser Phe Ser Ser Leu Gln Ile Lys Ala Leu Gln
                325                 330                 335

Asn Ala Val Glu Lys Glu Val Gln Ala Glu Asp Asn Ile Tyr Ile Glu
            340                 345                 350

Asn Ser Leu Tyr Ala Thr Asp
        355


<210> SEQ ID NO 18
<211> LENGTH: 1080
<212> TYPE: DNA
<213> ORGANISM: H. sapiens

<400> SEQUENCE: 18

atgcatcctc aagtggtcat cttaagcctc atcctacatc tggcagattc tgtagctggt      60

tctgtaaagg ttggtggaga ggcaggtcca tctgtcacac taccctgcca ctacagtgga     120

gctgtcacat caatgtgctg gaatagaggc tcatgttctc tattcacatg ccaaaatggc     180

attgtctgga ccaatggaac ccacgtcacc tatcggaagg acacacgcta taagctattg     240

gggaccttt caagaaggga tgtctctttg accatagaaa atacagctgt gtctgacagt     300

ggcgtatatt gttgccgtgt tgagcaccgt gggtggttca atgacatgaa aatcaccgta     360

tcattggaga ttgtgccacc caaggtcacg actactccaa ttgtcacaac tgttccaacc     420

gtcacgactg ttcgaacgag caccactgtt ccaacgacaa cgactgttcc aacgacaact     480

gttccaacaa caatgagcat tccaacgaca acgactgttc cgacgacaat gactgtttca     540

acgacaacga gcgttccaac gacaacgagc attccaacaa caacaagtgt tccagtgaca     600

acaacggtct ctacctttgt tcctccaatg cctttgccca ggcagaacca tgaaccagta     660

gccacttcac catcttcacc tcagccagca gaaacccacc ctacgacact gcagggagca     720

ataaggagag aacccaccag ctcaccattg tactcttaca caacagatgg gaatgacacc     780

gtgacagagt cttcagatgg cctttggaat aacaatcaaa ctcaactgtt cctagaacat     840

agtctactga cggccaatac cactaaagga atctatgctg gagtctgtat ttctgtcttg     900

gtgcttcttg ctcttttggg tgtcatcatt gccaaaaagt atttcttcaa aaaggaggtt     960

caacaactaa gtgtttcatt tagcagcctt caaattaaag ctttgcaaaa tgcagttgaa    1020

aaggaagtcc aagcagaaga caatatctac attgagaata gtctttatgc cacggactaa    1080


<210> SEQ ID NO 19
<211> LENGTH: 359
<212> TYPE: PRT
<213> ORGANISM: H. sapiens
<220> FEATURE:
<221> NAME/KEY: VARIANT
<222> LOCATION: (1)...(359)
<223> OTHER INFORMATION: TIM-1, allele 2

<400> SEQUENCE: 19

Met His Pro Gln Val Val Ile Leu Ser Leu Ile Leu His Leu Ala Asp
```

-continued

```
1               5                   10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
    50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
        115                 120                 125

Val Thr Thr Thr Pro Ile Val Thr Thr Val Pro Thr Val Thr Thr Val
    130                 135                 140

Arg Thr Ser Thr Thr Val Pro Thr Thr Thr Thr Val Pro Thr Thr Thr
145                 150                 155                 160

Val Pro Thr Thr Met Ser Ile Pro Thr Thr Thr Thr Val Pro Thr Thr
                165                 170                 175

Met Thr Val Ser Thr Thr Thr Ser Val Pro Thr Thr Thr Ser Ile Pro
            180                 185                 190

Thr Thr Thr Ser Val Pro Val Thr Thr Ala Val Ser Thr Phe Val Pro
        195                 200                 205

Pro Met Pro Leu Pro Arg Gln Asn His Glu Pro Val Ala Thr Ser Pro
    210                 215                 220

Ser Ser Pro Gln Pro Ala Glu Thr His Pro Thr Thr Leu Gln Gly Ala
225                 230                 235                 240

Ile Arg Arg Glu Pro Thr Ser Ser Pro Leu Tyr Ser Tyr Thr Thr Asp
                245                 250                 255

Gly Asn Asp Thr Val Thr Glu Ser Ser Asp Gly Leu Trp Asn Asn Asn
            260                 265                 270

Gln Thr Gln Leu Phe Leu Glu His Ser Leu Leu Thr Ala Asn Thr Thr
        275                 280                 285

Lys Gly Ile Tyr Ala Gly Val Cys Ile Ser Val Leu Val Leu Leu Ala
    290                 295                 300

Leu Leu Gly Val Ile Ile Ala Lys Lys Tyr Phe Phe Lys Lys Glu Val
305                 310                 315                 320

Gln Gln Leu Ser Val Ser Phe Ser Ser Leu Gln Ile Lys Ala Leu Gln
                325                 330                 335

Asn Ala Val Glu Lys Glu Val Gln Ala Glu Asp Asn Ile Tyr Ile Glu
            340                 345                 350

Asn Ser Leu Tyr Ala Thr Asp
        355
```

<210> SEQ ID NO 20
<211> LENGTH: 1080
<212> TYPE: DNA
<213> ORGANISM: H. sapiens

<400> SEQUENCE: 20

```
atgcatcctc aagtggtcat cttaagcctc atcctacatc tggcagattc tgtagctggt      60

tctgtaaagg ttggtggaga ggcaggtcca tctgtcacac taccctgcca ctacagtgga     120
```

-continued

```
gctgtcacat caatgtgctg gaatagaggc tcatgttctc tattcacatg ccaaaatggc    180

attgtctgga ccaatggaac ccacgtcacc tatcggaagg acacacgcta taagctattg    240

ggggaccttt caagaaggga tgtctctttg accatagaaa atacagctgt gtctgacagt    300

ggcgtatatt gttgccgtgt tgagcaccgt gggtggttca atgacatgaa aatcaccgta    360

tcattggaga ttgtgccacc caaggtcacg actactccaa ttgtcacaac tgttccaacc    420

gtcacgactg ttcgaacgag caccactgtt ccaacgacaa cgactgttcc aacgacaact    480

gttccaacaa caatgagcat tccaacgaca acgactgttc cgacgacaat gactgtttca    540

acgacaacga gcgttccaac gacaacgagc attccaacaa caacaagtgt tccagtgaca    600

acagcggtct ctacctttgt tcctccaatg cctttgccca ggcagaacca tgaaccagta    660

gccacttcac catcttcacc tcagccagca gaaacccacc ctacgacact gcagggagca    720

ataaggagag aacccaccag ctcaccattg tactcttaca caacagatgg gaatgacacc    780

gtgacagagt cttcagatgg cctttggaat aacaatcaaa ctcaactgtt cctagaacat    840

agtctactga cggccaatac cactaaagga atctatgctg gagtctgtat ttctgtcttg    900

gtgcttcttg ctcttttggg tgtcatcatt gccaaaaagt atttcttcaa aaaggaggtt    960

caacaactaa gtgtttcatt tagcagcctt caaattaaag ctttgcaaaa tgcagttgaa   1020

aaggaagtcc aagcagaaga caatatctac attgagaata gtctttatgc cacggactaa   1080
```

```
<210> SEQ ID NO 21
<211> LENGTH: 365
<212> TYPE: PRT
<213> ORGANISM: H. sapiens
<220> FEATURE:
<221> NAME/KEY: VARIANT
<222> LOCATION: (1)...(365)
<223> OTHER INFORMATION: TIM-1, allele 3

<400> SEQUENCE: 21

Met His Pro Gln Val Val Ile Leu Ser Leu Ile Leu His Leu Ala Asp
 1               5                  10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
    50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
        115                 120                 125

Val Thr Thr Thr Pro Ile Val Thr Thr Val Pro Thr Val Thr Thr Val
    130                 135                 140

Arg Thr Ser Thr Thr Val Pro Thr Thr Thr Thr Val Pro Met Thr Thr
145                 150                 155                 160

Thr Val Pro Thr Thr Thr Val Pro Thr Thr Met Ser Ile Pro Thr Thr
                165                 170                 175

Thr Thr Val Pro Thr Thr Met Thr Val Ser Thr Thr Thr Ser Val Pro
            180                 185                 190
```

```
Thr Thr Thr Ser Ile Pro Thr Thr Thr Ser Val Pro Val Thr Thr Ala
        195                 200                 205

Val Ser Thr Phe Val Pro Pro Met Pro Leu Pro Arg Gln Asn His Glu
    210                 215                 220

Pro Val Ala Thr Ser Pro Ser Ser Pro Gln Pro Ala Glu Thr His Pro
225                 230                 235                 240

Thr Thr Leu Gln Gly Ala Ile Arg Arg Glu Pro Thr Ser Ser Pro Leu
                245                 250                 255

Tyr Ser Tyr Thr Thr Asp Gly Asn Asp Thr Val Thr Glu Ser Ser Asp
            260                 265                 270

Gly Leu Trp Asn Asn Asn Gln Thr Gln Leu Phe Leu Glu His Ser Leu
        275                 280                 285

Leu Thr Ala Asn Thr Thr Lys Gly Ile Tyr Ala Gly Val Cys Ile Ser
    290                 295                 300

Val Leu Val Leu Leu Ala Leu Leu Gly Val Ile Ile Ala Lys Lys Tyr
305                 310                 315                 320

Phe Phe Lys Lys Glu Val Gln Gln Leu Ser Val Ser Phe Ser Ser Leu
                325                 330                 335

Gln Ile Lys Ala Leu Gln Asn Ala Val Glu Lys Glu Val Gln Ala Glu
            340                 345                 350

Asp Asn Ile Tyr Ile Glu Asn Ser Leu Tyr Ala Thr Asp
        355                 360                 365


<210> SEQ ID NO 22
<211> LENGTH: 1098
<212> TYPE: DNA
<213> ORGANISM: H. sapiens

<400> SEQUENCE: 22

atgcatcctc aagtggtcat cttaagcctc atcctacatc tggcagattc tgtagctggt     60

tctgtaaagg ttggtggaga ggcaggtcca tctgtcacac taccctgcca ctacagtgga    120

gctgtcacat caatgtgctg gaatagaggc tcatgttctc tattcacatg ccaaaatggc    180

attgtctgga ccaatggaac ccacgtcacc tatcggaagg acacacgcta taagctattg    240

ggggaccttt caagaaggga tgtctctttg accatagaaa atacagctgt gtctgacagt    300

ggcgtatatt gttgccgtgt tgagcaccgt gggtggttca atgacatgaa aatcaccgta    360

tcattggaga ttgtgccacc caaggtcacg actactccaa ttgtcacaac tgttccaacc    420

gtcacgactg ttcgaacgag caccactgtt ccaacgacaa cgactgttcc aatgacaacg    480

actgttccaa cgacaactgt tccaacaaca atgagcattc caacgacaac gactgttccg    540

acgacaatga ctgtttcaac gacaacgagc gttccaacga caacgagcat tccaacaaca    600

acaagtgttc cagtgacaac arcggtctct acctttgttc ctccaatgcc tttgcccagg    660

cagaaccatg aaccagtagc cacttcacca tcttcacctc agccagcaga aacccaccct    720

acgacactgc agggagcaat aaggagagaa cccaccagct caccattgta ctcttacaca    780

acagatggga atgacaccgt gacagagtct tcagatggcc tttggaataa caatcaaact    840

caactgttcc tagaacatag tctactgacg gccaatacca ctaaaggaat ctatgctgga    900

gtctgtattt ctgtcttggt gcttcttgct cttttgggtg tcatcattgc caaaaagtat    960

ttcttcaaaa aggaggttca acaactaagt gtttcattta gcagccttca aattaaagct   1020

ttgcaaaatg cagttgaaaa ggaagtccaa gcagaagaca atatctacat tgagaatagt   1080

ctttatgcca cggactaa                                                  1098
```

-continued

```
<210> SEQ ID NO 23
<211> LENGTH: 359
<212> TYPE: PRT
<213> ORGANISM: H. sapiens
<220> FEATURE:
<221> NAME/KEY: VARIANT
<222> LOCATION: (1)...(359)
<223> OTHER INFORMATION: TIM-1, allele 4

<400> SEQUENCE: 23

Met His Pro Gln Val Val Ile Leu Ser Leu Ile Leu His Leu Ala Asp
 1               5                  10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
    50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
        115                 120                 125

Val Thr Thr Thr Pro Ile Val Thr Thr Val Pro Thr Val Thr Thr Val
    130                 135                 140

Arg Thr Ser Thr Thr Val Pro Thr Thr Thr Thr Val Pro Thr Thr Thr
145                 150                 155                 160

Val Pro Thr Thr Met Ser Ile Pro Thr Thr Thr Thr Val Pro Thr Thr
                165                 170                 175

Met Thr Val Ser Thr Thr Thr Ser Val Pro Thr Thr Thr Ser Ile Pro
            180                 185                 190

Thr Thr Thr Ser Val Pro Val Thr Thr Ser Val Ser Thr Phe Val Pro
        195                 200                 205

Pro Met Pro Leu Pro Arg Gln Asn His Glu Pro Val Ala Thr Ser Pro
    210                 215                 220

Ser Ser Pro Gln Pro Ala Glu Thr His Pro Thr Thr Leu Gln Gly Thr
225                 230                 235                 240

Ile Arg Arg Glu Pro Thr Ser Ser Pro Leu Tyr Ser Tyr Thr Thr Asp
                245                 250                 255

Gly Asn Asp Thr Val Thr Glu Ser Ser Asp Gly Leu Trp Ser Asn Asn
            260                 265                 270

Gln Thr Gln Leu Phe Leu Glu His Ser Leu Leu Thr Ala Asn Thr Thr
        275                 280                 285

Lys Gly Ile Tyr Ala Gly Val Cys Ile Ser Val Leu Val Leu Leu Ala
    290                 295                 300

Leu Leu Gly Val Ile Ile Ala Lys Lys Tyr Phe Phe Lys Lys Glu Val
305                 310                 315                 320

Gln Gln Leu Ser Val Ser Phe Ser Ser Leu Gln Ile Lys Ala Leu Gln
                325                 330                 335

Asn Ala Val Glu Lys Glu Val Gln Ala Glu Asp Asn Ile Tyr Ile Glu
            340                 345                 350

Asn Ser Leu Tyr Ala Thr Asp
        355
```

<210> SEQ ID NO 24
<211> LENGTH: 1079
<212> TYPE: DNA
<213> ORGANISM: H. sapiens

<400> SEQUENCE: 24
atgcatcctc aagtggtcat cttaagcctc atcctacatc tggcagattc tgtagctggt 60
tctgtaaagg ttggtggaga ggcaggtcca tctgtcacac taccctgcca ctacagtgga 120
gctgtcacat caatgtgctg gaatagaggc tcatgttctc tattcacatg ccaaaatggc 180
attgtctgga ccaatggaac ccacgtcacc tatcggaagg acacacgcta taagctattg 240
ggggaccttt caagaaggga tgtctctttg accatagaaa atacagctgt gtctgacagt 300
ggcgtatatt gttgccgtgt tgagcaccgt gggtggttca atgacatgaa aatcaccgta 360
tcattggaga ttgtgccacc caaggtcacg actactccaa ttgtcacaac tgttccaacc 420
gtcacgactg ttcgaacgag caccactgtt ccaacgacaa cgactgttcc aacgacaact 480
gttccaacaa caatgagcat tccaacgaca acggactgtt ccgacgacaa tgactgtttc 540
aacgacaacg agcgttccaa cgacaacgag cattccaaca acaacaagtg ttccagtgac 600
aacatgtctc tacctttgtt cctccaatgc ctttgcccag gcagaaccat gaaccagtag 660
ccacttcacc atcttcacct cagccagcag aaacccaccc tacgacactg cagggagcaa 720
taaggagaga acccaccagc tcaccattgt actcttacac aacagatggg aatgacaccg 780
tgacagagtc ttcagatggc ctttggarta acaatcaaac tcaactgttc ctagaacata 840
gtctactgac ggccaatacc actaaaggaa tctatgctgg agtctgtatt tctgtcttgg 900
tgcttcttgc tcttttgggt gtcatcattg ccaaaaagta tttcttcaaa aaggaggttc 960
aacaactaag tgtttcattt agcagccttc aaattaaagc tttgcaaaat gcagttgaaa 1020
aggaagtcca agcagaagac aatatctaca ttgagaatag tctttatgcc acggactaa 1079

<210> SEQ ID NO 25
<211> LENGTH: 364
<212> TYPE: PRT
<213> ORGANISM: H. sapiens
<220> FEATURE:
<221> NAME/KEY: VARIANT
<222> LOCATION: (1)...(364)
<223> OTHER INFORMATION: TIM-1 allele 5

<400> SEQUENCE: 25

Met His Pro Gln Val Val Ile Leu Ser Leu Ile Leu His Leu Ala Asp
1 5 10 15

Ser Val Ala Gly Ser Val Lys Val Gly Gly Glu Ala Gly Pro Ser Val
20 25 30

Thr Leu Pro Cys His Tyr Ser Gly Ala Val Thr Ser Met Cys Trp Asn
35 40 45

Arg Gly Ser Cys Ser Leu Phe Thr Cys Gln Asn Gly Ile Val Trp Thr
50 55 60

Asn Gly Thr His Val Thr Tyr Arg Lys Asp Thr Arg Tyr Lys Leu Leu
65 70 75 80

Gly Asp Leu Ser Arg Arg Asp Val Ser Leu Thr Ile Glu Asn Thr Ala
85 90 95

Val Ser Asp Ser Gly Val Tyr Cys Cys Arg Val Glu His Arg Gly Trp
100 105 110

Phe Asn Asp Met Lys Ile Thr Val Ser Leu Glu Ile Val Pro Pro Lys
115 120 125

```
Val Thr Thr Thr Pro Ile Val Thr Thr Val Pro Thr Val Thr Thr Val
    130                 135                 140

Arg Thr Ser Thr Thr Val Pro Thr Thr Thr Thr Val Pro Met Thr Thr
145                 150                 155                 160

Thr Val Pro Thr Thr Thr Val Pro Thr Thr Met Ser Ile Pro Thr Thr
                165                 170                 175

Thr Thr Val Pro Thr Thr Met Thr Val Ser Thr Thr Thr Ser Val Pro
            180                 185                 190

Thr Thr Thr Ser Ile Pro Thr Thr Ser Val Pro Val Thr Thr Thr Val
        195                 200                 205

Ser Thr Phe Val Pro Pro Met Pro Leu Pro Arg Gln Asn His Glu Pro
    210                 215                 220

Val Ala Thr Ser Pro Ser Ser Pro Gln Pro Ala Glu Thr His Pro Thr
225                 230                 235                 240

Thr Leu Gln Gly Ala Ile Arg Arg Glu Pro Thr Ser Ser Pro Leu Tyr
                245                 250                 255

Ser Tyr Thr Thr Asp Gly Asn Asp Thr Val Thr Glu Ser Ser Asp Gly
            260                 265                 270

Leu Trp Asn Asn Asn Gln Thr Gln Leu Phe Leu Glu His Ser Leu Leu
        275                 280                 285

Thr Ala Asn Thr Thr Lys Gly Ile Tyr Ala Gly Val Cys Ile Ser Val
    290                 295                 300

Leu Val Leu Leu Ala Leu Leu Gly Val Ile Ile Ala Lys Lys Tyr Phe
305                 310                 315                 320

Phe Lys Lys Glu Val Gln Gln Leu Ser Val Ser Phe Ser Ser Leu Gln
                325                 330                 335

Ile Lys Ala Leu Gln Asn Ala Val Glu Lys Glu Val Gln Ala Glu Asp
            340                 345                 350

Asn Ile Tyr Ile Glu Asn Ser Leu Tyr Ala Thr Asp
        355                 360
```

<210> SEQ ID NO 26
<211> LENGTH: 1095
<212> TYPE: DNA
<213> ORGANISM: H. sapiens

<400> SEQUENCE: 26

```
atgcatcctc aagtggtcat cttaagcctc atcctacatc tggcagattc tgtagctggt      60

tctgtaaagg ttggtggaga ggcaggtcca tctgtcacac taccctgcca ctacagtgga     120

gctgtcacat caatgtgctg gaatagaggc tcatgttctc tattcacatg ccaaaatggc     180

attgtctgga ccaatggaac ccacgtcacc tatcggaagg acacacgcta taagctattg     240

ggggaccttt caagaaggga tgtctctttg accatagaaa atacagctgt gtctgacagt     300

ggcgtatatt gttgccgtgt tgagcaccgt gggtggttca atgacatgaa aatcaccgta     360

tcattggaga ttgtgccacc caaggtcacg actactccaa ttgtcacaac tgttccaacc     420

gtcacgactg ttcgaacgag caccactgtt ccaacgacaa cgactgttcc aatgacaacg     480

actgttccaa cgacaactgt tccaacaaca atgagcattc caacgacaac gactgttccg     540

acgacaatga ctgtttcaac gacaacgagc gttccaacga caacgagcat tccaacaaca     600

agtgttccag tgacaacaac ggtctctacc tttgttcctc caatgccttt gcccaggcag     660

aaccatgaac cagtagccac ttcaccatct tcacctcagc cagcagaaac ccaccctacg     720

acactgcagg gagcaataag gagagaaccc accagctcac cattgtactc ttacacaaca     780

gatgggaatg acaccgtgac agagtcttca gatggccttt ggaataacaa tcaaactcaa     840
```

```
ctgttcctag aacatagtct actgacggcc aataccacta aaggaatcta tgctggagtc    900

tgtatttctg tcttggtgct tcttgctctt ttgggtgtca tcattgccaa aaagtatttc    960

ttcaaaaagg aggttcaaca actaagtgtt tcatttagca gccttcaaat taaagctttg   1020

caaaatgcag ttgaaaagga agtccaagca gaagacaata tctacattga gaatagtctt   1080

tatgccacgg actaa                                                    1095
```

```
<210> SEQ ID NO 27
<211> LENGTH: 364
<212> TYPE: PRT
<213> ORGANISM: H. sapiens
<220> FEATURE:
<221> NAME/KEY: VARIANT
<222> LOCATION: (1)...(364)
<223> OTHER INFORMATION: TIM-1, allele 6

<400> SEQUENCE: 27

Met His Pro Gln Val Val Ile Leu Ser Leu Ile Leu His Leu Ala Asp
 1               5                  10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
    50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Gly Ile Val Pro Pro Lys
        115                 120                 125

Val Thr Thr Thr Pro Ile Val Thr Thr Val Pro Thr Val Thr Thr Val
    130                 135                 140

Arg Thr Ser Thr Thr Val Pro Thr Thr Thr Thr Val Pro Met Thr Thr
145                 150                 155                 160

Thr Val Pro Thr Thr Thr Val Pro Thr Thr Met Ser Ile Pro Thr Thr
                165                 170                 175

Thr Thr Val Pro Thr Thr Met Thr Val Ser Thr Thr Thr Ser Val Pro
            180                 185                 190

Thr Thr Thr Ser Ile Pro Thr Thr Ser Val Pro Val Thr Thr Thr Val
        195                 200                 205

Ser Thr Phe Val Pro Pro Met Pro Leu Pro Arg Gln Asn His Glu Pro
    210                 215                 220

Val Ala Thr Ser Pro Ser Ser Pro Gln Pro Ala Glu Thr His Pro Thr
225                 230                 235                 240

Thr Leu Gln Gly Ala Ile Arg Arg Glu Pro Thr Ser Ser Pro Leu Tyr
                245                 250                 255

Ser Tyr Thr Thr Asp Gly Asp Asp Thr Val Thr Glu Ser Ser Asp Gly
            260                 265                 270

Leu Trp Asn Asn Asn Gln Thr Gln Leu Phe Leu Glu His Ser Leu Leu
        275                 280                 285

Thr Ala Asn Thr Thr Lys Gly Ile Tyr Ala Gly Val Cys Ile Ser Val
    290                 295                 300
```

-continued

```
Leu Val Leu Leu Ala Leu Leu Gly Val Ile Ile Ala Lys Lys Tyr Phe
305                 310                 315                 320

Phe Lys Lys Glu Val Gln Gln Leu Ser Val Ser Phe Ser Ser Leu Gln
                325                 330                 335

Ile Lys Ala Leu Gln Asn Ala Val Glu Lys Glu Val Gln Ala Glu Asp
            340                 345                 350

Asn Ile Tyr Ile Glu Asn Ser Leu Tyr Ala Thr Asp
        355                 360
```

<210> SEQ ID NO 28
<211> LENGTH: 1099
<212> TYPE: DNA
<213> ORGANISM: H. sapiens

<400> SEQUENCE: 28

```
atgcatcctc aagtggtcat cttaagcctc atcctacatc tggcagattc tgtagctggt     60

tctgtaaagg ttggtggaga ggcaggtcca tctgtcacac taccctgcca ctacagtgga    120

gctgtcacat caatgtgctg gaatagaggc tcatgttctc tattcacatg ccaaaatggc    180

attgtctgga ccaatggaac ccacgtcacc tatcggaagg acacacgcta taagctattg    240

ggggaccttt caagaaggga tgtctctttg accatagaaa atacagctgt gtctgacagt    300

ggcgtatatt gttgccgtgt tgagcaccgt gggtggttca atgacatgaa aatcaccgta    360

tcattggaga ttgtgccacc caaggtcacg actactccaa ttgtcacaac tgttccaacc    420

gtcacgactg ttcgaacgag caccactgtt ccaacgacaa cgactgttcc aatgacaacc    480

gactgttcca acgacaactg ttccaacaac aatgagcatt ccaacgacaa cgactgttcc    540

gacgacaatg actgtttcaa cgacaacgag cgttccaacg acaacgagca ttccaacaac    600

aacaagtgtt ccagtgacaa caacggtctc tacctttgtt cctccaatgc ctttgcccag    660

gcagaaccat gaaccagtag ccacttcacc atcttcacct cagccagcag aaacccaccc    720

tacgacactg cagggagcaa taaggagaga acccaccagc tcaccattgt actcttacac    780

aacagatggg gatgacaccg tgacagagtc ttcagatggc ctttggaata acaatcaaac    840

tcaactgttc ctagaacata gtctactgac ggccaatacc actaaaggaa tctatgctgg    900

agtctgtatt tctgtcttgg tgcttcttgc tcttttgggt gtcatcattg ccaaaaagta    960

tttcttcaaa aaggaggttc aacaactaag tgtttcattt agcagccttc aaattaaagc   1020

tttgcaaaat gcagttgaaa aggaagtcca agcagaagac aatatctaca ttgagaatag   1080

tctttatgcc acggactaa                                                1099
```

<210> SEQ ID NO 29
<211> LENGTH: 301
<212> TYPE: PRT
<213> ORGANISM: H. sapiens
<220> FEATURE:
<221> NAME/KEY: VARIANT
<222> LOCATION: (1)...(301)
<223> OTHER INFORMATION: TIM-3, allele 1

<400> SEQUENCE: 29

```
Met Phe Ser His Leu Pro Phe Asp Cys Val Leu Leu Leu Leu Leu Leu
 1               5                  10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
```

```
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
    290                 295                 300


<210> SEQ ID NO 30
<211> LENGTH: 1116
<212> TYPE: DNA
<213> ORGANISM: H. sapiens

<400> SEQUENCE: 30

ggagagttaa aactgtgcct aacagaggtg tcctctgact tttcttctgc aagctccatg     60

ttttcacatc ttccctttga ctgtgtcctg ctgctgctgc tgctactact tacaaggtcc    120

tcagaagtgg aatacagagc ggaggtcggt cagaatgcct atctgccctg cttctacacc    180

ccagccgccc cagggaacct cgtgcccgtc tgctggggca aaggagcctg tcctgtgttt    240

gaatgtggca acgtggtgct caggactgat gaaagggatg tgaattattg gacatccaga    300

tactggctaa atggggattt ccgcaaagga gatgtgtccc tgaccataga gaatgtgact    360

ctagcagaca gtgggatcta ctgctgccgg atccaaatcc caggcataat gaatgatgaa    420

aaatttaacc tgaagttggt catcaaacca gccaaggtca cccctgcacc gactctgcag    480

agagacttca ctgcagcctt tccaaggatg cttaccacca ggggacatgg cccagcagag    540

acacagacac tggggagcct ccctgatata aatctaacac aaatatccac attggccaat    600

gagttacggg actctagatt ggccaatgac ttacgggact ctggagcaac catcagaata    660

ggcatctaca tcggagcagg gatctgtgct gggctggctc tggctcttat cttcggcgct    720

ttaattttca aatggtattc tcatagcaaa gagaagatac agaatttaag cctcatctct    780
```

```
ttggccaacc tccctccctc aggattggca aatgcagtag cagagggaat tcgctcagaa    840

gaaaacatct ataccattga agagaacgta tatgaagtgg aggagcccaa tgagtattat    900

tgctatgtca gcagcaggca gcaaccctca caacctttgg gttgtcgctt tgcaatgcca    960

tagatccaac caccttattt ttgagcttgg tgttttgtct tttcagaaa ctatgagctg   1020

tgtcacctga ctggttttgg aggttctgtc cactgctatg gagcagagtt ttcccatttt   1080

cagaagataa tgactcacat gggaattgaa ctggga                             1116
```

```
<210> SEQ ID NO 31
<211> LENGTH: 301
<212> TYPE: PRT
<213> ORGANISM: H. sapiens
<220> FEATURE:
<221> NAME/KEY: VARIANT
<222> LOCATION: (1)...(301)
<223> OTHER INFORMATION: TIM-3, allele 2

<400> SEQUENCE: 31

Met Phe Ser His Leu Pro Phe Asp Cys Val Leu Leu Leu Leu Leu Leu
 1               5                  10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Leu Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
```

-continued 290 295 300

<210> SEQ ID NO 32
<211> LENGTH: 1116
<212> TYPE: DNA
<213> ORGANISM: H. sapiens

<400> SEQUENCE: 32

```
ggagagttaa aactgtgcct aacagaggtg tcctctgact tttcttctgc aagctccatg     60
ttttcacatc ttccctttga ctgtgtcctg ctgctgctgc tgctactact tacaaggtcc    120
tcagaagtgg aatacagagc ggaggtcggt cagaatgcct atctgccctg cttctacacc    180
ccagccgccc cagggaacct cgtgcccgtc tgctggggca aaggagcctg tcctgtgttt    240
gaatgtggca acgtggtgct caggactgat gaaagggatg tgaattattg gacatccaga    300
tactggctaa atggggattt ccgcaaagga gatgtgtccc tgaccataga gaatgtgact    360
ctagcagaca gtgggatcta ctgctgccgg atccaaatcc caggcataat gaatgatgaa    420
aaatttaacc tgaagttggt catcaaacca gccaaggtca cccctgcacc gactcggcag    480
agagacttca ctgcagcctt tccaaggatg cttaccacca ggggacatgg cccagcagag    540
acacagacac tggggagcct ccctgatata aatctaacac aaatatccac attggccaat    600
gagttacggg actctagatt ggccaatgac ttacgggact ctggagcaac catcagaata    660
ggcatctaca tcggagcagg gatctgtgct gggctggctc tggctcttat cttcggcgct    720
ttaattttca aatggtattc tcatagcaaa gagaagatac agaatttaag cctcatctct    780
ttggccaacc tccctccctc aggattggca aatgcagtag cagagggaat tcgctcagaa    840
gaaaacatct ataccattga agagaacgta tatgaagtgg aggagcccaa tgagtattat    900
tgctatgtca gcagcaggca gcaaccctca caacctttgg gttgtcgctt tgcaatgcca    960
tagatccaac caccttattt ttgagcttgg tgttttgtct tttcagaaa ctatgagctg   1020
tgtcacctga ctggttttgg aggttctgtc cactgctatg gagcagagtt ttcccatttt   1080
cagaagataa tgactcacat gggaattgaa ctggga                             1116
```

<210> SEQ ID NO 33
<211> LENGTH: 378
<212> TYPE: PRT
<213> ORGANISM: H. sapiens
<220> FEATURE:
<221> NAME/KEY: VARIANT
<222> LOCATION: (1)...(378)
<223> OTHER INFORMATION: TIM-4, allele 1

<400> SEQUENCE: 33

```
Met Ser Lys Glu Pro Leu Ile Leu Trp Leu Met Ile Glu Phe Trp Trp
1               5                   10                  15

Leu Tyr Leu Thr Pro Val Thr Ser Glu Thr Val Val Thr Glu Val Leu
            20                  25                  30

Gly His Arg Val Thr Leu Pro Cys Leu Tyr Ser Ser Trp Ser His Asn
        35                  40                  45

Ser Asn Ser Met Cys Trp Gly Lys Asp Gln Cys Pro Tyr Ser Gly Cys
    50                  55                  60

Lys Glu Ala Leu Ile Arg Thr Asp Gly Met Arg Val Thr Ser Arg Lys
65                  70                  75                  80

Ser Ala Lys Tyr Arg Leu Gln Gly Thr Ile Pro Arg Gly Asp Val Ser
                85                  90                  95

Leu Thr Ile Leu Asn Pro Ser Glu Ser Asp Ser Gly Val Tyr Cys Cys
            100                 105                 110
```

-continued

```
Arg Ile Glu Val Pro Gly Trp Phe Asn Asp Val Lys Ile Asn Val Arg
        115                 120                 125

Leu Asn Leu Gln Arg Ala Ser Thr Thr Thr His Arg Thr Ala Thr Thr
    130                 135                 140

Thr Thr Arg Arg Thr Thr Thr Thr Ser Pro Thr Thr Thr Arg Gln Met
145                 150                 155                 160

Thr Thr Thr Pro Ala Ala Leu Pro Thr Thr Val Val Thr Thr Pro Asp
                165                 170                 175

Leu Thr Thr Gly Thr Pro Leu Gln Met Thr Thr Ile Ala Val Phe Thr
            180                 185                 190

Thr Ala Asn Thr Cys Leu Ser Leu Thr Pro Ser Thr Leu Pro Glu Glu
        195                 200                 205

Ala Thr Gly Leu Leu Thr Pro Glu Pro Ser Lys Glu Gly Pro Ile Leu
    210                 215                 220

Thr Ala Glu Ser Glu Thr Val Leu Pro Ser Asp Ser Trp Ser Ser Ala
225                 230                 235                 240

Glu Ser Thr Ser Ala Asp Thr Val Leu Leu Thr Ser Lys Glu Ser Lys
                245                 250                 255

Val Trp Asp Leu Pro Ser Thr Ser His Val Ser Met Trp Lys Thr Ser
            260                 265                 270

Asp Ser Val Ser Ser Pro Gln Pro Gly Ala Ser Asp Thr Ala Val Pro
        275                 280                 285

Glu Gln Asn Lys Thr Thr Lys Thr Gly Gln Met Asp Gly Ile Pro Met
    290                 295                 300

Ser Met Lys Asn Glu Met Pro Ile Ser Gln Leu Leu Met Ile Ile Ala
305                 310                 315                 320

Pro Ser Leu Gly Phe Val Leu Phe Ala Leu Phe Val Ala Phe Leu Leu
                325                 330                 335

Arg Gly Lys Leu Met Glu Thr Tyr Cys Ser Gln Lys His Thr Arg Leu
            340                 345                 350

Asp Tyr Ile Gly Asp Ser Lys Asn Val Leu Asn Asp Val Gln His Gly
        355                 360                 365

Arg Glu Asp Glu Asp Gly Leu Phe Thr Leu
    370                 375
```

<210> SEQ ID NO 34
<211> LENGTH: 1156
<212> TYPE: DNA
<213> ORGANISM: H. sapiens

<400> SEQUENCE: 34

```
atgtccaaag aacctctcat tctctggctg atgattgagt tttggtggct ttacctgaca      60

ccagtcactt cagagactgt tgtgacggag gttttgggtc accgggtgac tttgccctgt     120

ctgtactcat cctggtctca caacagcaac agcatgtgct gggggaaaga ccagtgcccc     180

tactccggtt gcaaggaggc gctcatccgc actgatggaa tgagggtgac ctcaagaaag     240

tcagcaaaat atagacttca ggggactatc ccgagaggtg atgtctcctt gaccatctta     300

aaccccagtg aaagtgacag cggtgtgtac tgctgccgca tagaagtgcc tggctggttc     360

aacgatgtaa agataaacgt gcgcctgaat ctacagagag cctcaacaac cacgcacaga     420

acagcaacca ccaccacacg cagaacaaca acaacaagcc ccaccaccac ccgacaaatg     480

acaacaaccc cagctgcact tccaacaaca gtcgtgacca cacccgatct cacaaccgga     540

acaccactcc agatgacaac cattgccgtc ttcacaacag caaacacgtg cctttcacta     600
```

-continued

```
accccaagca cccttccgga ggaagccaca ggtcttctga ctcccgagcc ttctaaggaa    660

gggcccatcc tcactgcaga atcagaaact gtcctcccca gtgattcctg gagtagtgct    720

gagtctactt ctgctgacac tgtcctgctg acatccaaag agtccaaagt ttgggatctc    780

ccatcaacat cccacgtgtc aatgtggaaa acgagtgatt ctgtgtcttc tcctcagcct    840

ggagcatctg atacagcagt tcctgagcag aacaaaacaa caaaaacagg acagatggat    900

ggaataccca tgtcaatgaa gaatgaaatg cccatctccc aactactgat gatcatcgcc    960

ccctccttgg gatttgtgct cttcgcattg tttgtggcgt ttctcctgag agggaaactc   1020

atggaaacct attgttcgca gaaacacaca aggctagact acattggaga tagtaaaaat   1080

gtcctcaatg acgtgcagca tggaagggaa gacgaagacg gcctttttac cctctaacaa   1140

cgcagtagca tgttag                                                   1156
```

```
<210> SEQ ID NO 35
<211> LENGTH: 378
<212> TYPE: PRT
<213> ORGANISM: H. sapiens
<220> FEATURE:
<221> NAME/KEY: VARIANT
<222> LOCATION: (1)...(378)
<223> OTHER INFORMATION: TIM-4, allele 2

<400> SEQUENCE: 35

Met Ser Lys Glu Pro Leu Ile Leu Trp Leu Met Ile Glu Phe Trp Trp
 1               5                  10                  15

Leu Tyr Leu Thr Pro Val Thr Ser Glu Thr Val Val Thr Glu Val Leu
            20                  25                  30

Gly His Arg Val Thr Leu Pro Cys Leu Tyr Ser Ser Trp Ser His Asn
        35                  40                  45

Ser Asn Ser Met Cys Trp Gly Lys Asp Gln Cys Pro Tyr Ser Gly Cys
    50                  55                  60

Lys Glu Ala Leu Ile Arg Thr Asp Gly Met Arg Val Thr Ser Arg Lys
65                  70                  75                  80

Ser Ala Lys Tyr Arg Leu Gln Gly Thr Ile Pro Arg Gly Asp Val Ser
                85                  90                  95

Leu Thr Ile Leu Asn Pro Ser Glu Ser Asp Ser Gly Val Tyr Cys Cys
            100                 105                 110

Arg Ile Glu Val Pro Gly Trp Phe Asn Asp Val Lys Ile Asn Val Arg
        115                 120                 125

Leu Asn Leu Gln Arg Ala Ser Thr Thr Thr His Arg Thr Ala Thr Thr
    130                 135                 140

Thr Thr Arg Arg Thr Thr Thr Thr Ser Pro Thr Thr Thr Arg Gln Met
145                 150                 155                 160

Thr Thr Thr Pro Ala Ala Leu Pro Thr Thr Val Val Thr Thr Pro Asp
                165                 170                 175

Leu Thr Thr Gly Thr Pro Leu Gln Met Thr Thr Ile Ala Val Phe Thr
            180                 185                 190

Thr Ala Asn Thr Cys Leu Ser Leu Thr Pro Ser Thr Leu Pro Glu Glu
        195                 200                 205

Ala Thr Gly Leu Leu Thr Pro Glu Pro Ser Lys Glu Gly Pro Ile Leu
    210                 215                 220

Thr Ala Glu Ser Glu Thr Val Leu Pro Ser Asp Ser Trp Ser Ser Val
225                 230                 235                 240

Glu Ser Thr Ser Ala Asp Thr Val Leu Leu Thr Ser Lys Glu Ser Lys
                245                 250                 255
```

-continued

```
Val Trp Asp Leu Pro Ser Thr Ser His Val Ser Met Trp Lys Thr Ser
            260                 265                 270

Asp Ser Val Ser Ser Pro Gln Pro Gly Ala Ser Asp Thr Ala Val Pro
        275                 280                 285

Glu Gln Asn Lys Thr Thr Lys Thr Gly Gln Met Asp Gly Ile Pro Met
    290                 295                 300

Ser Met Lys Asn Glu Met Pro Ile Ser Gln Leu Leu Met Ile Ile Ala
305                 310                 315                 320

Pro Ser Leu Gly Phe Val Leu Phe Ala Leu Phe Val Ala Phe Leu Leu
                325                 330                 335

Arg Gly Lys Leu Met Glu Thr Tyr Cys Ser Gln Lys His Thr Arg Leu
            340                 345                 350

Asp Tyr Ile Gly Asp Ser Lys Asn Val Leu Asn Asp Val Gln His Gly
        355                 360                 365

Arg Glu Asp Glu Asp Gly Leu Phe Thr Leu
    370                 375
```

<210> SEQ ID NO 36
<211> LENGTH: 1156
<212> TYPE: DNA
<213> ORGANISM: H. sapiens

<400> SEQUENCE: 36

```
atgtccaaag aacctctcat tctctggctg atgattgagt tttggtggct ttacctgaca     60

ccagtcactt cagagactgt tgtgacggag gttttgggtc accgggtgac tttgccctgt    120

ctgtactcat cctggtctca caacagcaac agcatgtgct gggggaaaga ccagtgcccc    180

tactccggtt gcaaggaggc gctcatccgc actgatggaa tgagggtgac ctcaagaaag    240

tcagcaaaat atagacttca ggggactatc ccgagaggtg atgtctcctt gaccatctta    300

aaccccagtg aaagtgacag cggtgtgtac tgctgccgca tagaagtgcc tggctggttc    360

aacgatgtaa agataaacgt gcgcctgaat ctacagagag cctcaacaac cacgcacaga    420

acagcaacca ccaccacacg cagaacaaca acaacaagcc ccaccaccac ccgacaaatg    480

acaacaaccc cagctgcact tccaacaaca gtcgtgacca cacccgatct cacaaccgga    540

acaccactcc agatgacaac cattgccgtc ttcacaacag caaacacgtg cctttcacta    600

accccaagca cccttccgga ggaagccaca ggtcttctga ctcccgagcc ttctaaggaa    660

gggcccatcc tcactgcaga atcagaaact gtcctcccca gtgattcctg gagtagtgtt    720

gagtctactt ctgctgacac tgtcctgctg acatccaaag agtccaaagt ttgggatctc    780

ccatcaacat cccacgtgtc aatgtggaaa acgagtgatt ctgtgtcttc tcctcagcct    840

ggagcatctg atacagcagt tcctgagcag aacaaaaacaa caaaaacagg acagatggat    900

ggaataccca tgtcaatgaa gaatgaaatg cccatctccc aactactgat gatcatcgcc    960

ccctccttgg gatttgtgct cttcgcattg tttgtggcgt ttctcctgag agggaaactc   1020

atggaaacct attgttcgca gaaacacaca aggctagact acattggaga tagtaaaaat   1080

gtcctcaatg acgtgcagca tggaagggaa gacgaagacg gcctttttac cctctaacaa   1140

cgcagtagca tgttag                                                   1156
```

<210> SEQ ID NO 37
<211> LENGTH: 481
<212> TYPE: DNA
<213> ORGANISM: H. sapiens
<220> FEATURE:
<221> NAME/KEY: exon
<222> LOCATION: (152)...(430)

<223> OTHER INFORMATION: Exon 3, reference sequence

<400> SEQUENCE: 37
ttctagctgg gcaatgacca agattgacag ttcaggaagt taactccacc tagggacagt 60
ctgtcattgg tgtgctaggg tacagttcca gcctgaggct cttgtttctt gtttgactta 120
tgctcactct catgttgatt tctgactcca gccaaggtca cgactactcc aattgtcaca 180
actgttccaa ccgtcacgac tgttcgaacg agcaccactg ttccaacgac aacgactgtt 240
ccaacgacaa ctgttccaac aacaatgagc attccaacga caacgactgt tctgacgaca 300
atgactgttt caacgacaac gagcgttcca acgacaacga gcattccaac aacaacaagt 360
gttccagtga caacaactgt ctctaccttt gttcctccaa tgcctttgcc caggcagaac 420
catgaaccag gtaaaacaga tgtgtttgga agcccaaagg ccttctaatg aggagctgcg 480
g 481

<210> SEQ ID NO 38
<211> LENGTH: 499
<212> TYPE: DNA
<213> ORGANISM: H. sapiens
<220> FEATURE:
<221> NAME/KEY: exon
<222> LOCATION: (152)...(448)
<223> OTHER INFORMATION: Exon 3, INS157 polymorphism

<400> SEQUENCE: 38
ttctagctgg gcaatgacca agattgacag ttcaggaagt taactccacc tagggacagt 60
ctgtcattgg tgtgctaggg tacagttcca gcctgaggct cttgtttctt gtttgactta 120
tgctcactct catgttgatt tctgactcca gccaaggtca cgactactcc aattgtcaca 180
actgttccaa ccgtcacgac tgttcgaacg agcaccactg ttccaacgac aacgactgtt 240
ccaatgacaa cgactgttcc aacgacaact gttccaacaa caatgagcat tccaacgaca 300
acgactgttc tgacgacaat gactgtttca acgacaacga gcgttccaac gacaacgagc 360
attccaacaa caacaagtgt tccagtgaca acaactgtct ctacctttgt tcctccaatg 420
cctttgccca ggcagaacca tgaaccaggt aaaacagatg tgtttggaag cccaaaggcc 480
ttctaatgag gagctgcgg 499

<210> SEQ ID NO 39
<211> LENGTH: 496
<212> TYPE: DNA
<213> ORGANISM: H. sapiens
<220> FEATURE:
<221> NAME/KEY: exon
<222> LOCATION: (152)...(445)
<223> OTHER INFORMATION: Exon 3, 195delT polymorphism

<400> SEQUENCE: 39
ttctagctgg gcaatgacca agattgacag ttcaggaagt taactccacc tagggacagt 60
ctgtcattgg tgtgctaggg tacagttcca gcctgaggct cttgtttctt gtttgactta 120
tgctcactct catgttgatt tctgactcca gccaaggtca cgactactcc aattgtcaca 180
actgttccaa ccgtcacgac tgttcgaacg agcaccactg ttccaacgac aacgactgtt 240
ccaatgacaa cgactgttcc aacgacaact gttccaacaa caatgagcat tccaacgaca 300
acgactgttc tgacgacaat gactgtttca acgacaacga gcgttccaac gacaacgagc 360
attccaacaa caagtgttcc agtgacaaca actgtctcta cctttgttcc tccaatgcct 420
ttgcccaggc agaaccatga accaggtaaa acagatgtgt ttggaagccc aaaggccttc 480
taatgaggag ctgcgg 496

<210> SEQ ID NO 40
<211> LENGTH: 496
<212> TYPE: DNA
<213> ORGANISM: H. sapiens
<220> FEATURE:
<221> NAME/KEY: exon
<222> LOCATION: (152)...(445)
<223> OTHER INFORMATION: Exon 3, 157insMTTVP polymorphism

<400> SEQUENCE: 40
ttctagctgg gcaatgacca agattgacag ttcaggaagt taactccacc tagggacagt 60
ctgtcattgg tgtgctaggg tacagttcca gcctgaggct cttgtttctt gtttgactta 120
tgctcactct catgttgatt tctgactcca gccaaggtca cgactactcc aattgtcaca 180
actgttccaa ccgtcacgac tgttcgaacg agcaccactg ttccaacgac aacgactgtt 240
ccaatgacga ctgttccaac gacaactgtt ccaacaacaa tgagcattcc aacgacaacg 300
actgttctga cgacaatgac tgtttcaacg acaacgagcg ttccaacgac aacgagcatt 360
ccaacaacaa caagtgttcc agtgacaaca actgtctcta cctttgttcc tccaatgcct 420
ttgcccaggc agaaccatga accaggtaaa acagatgtgt ttggaagccc aaaggccttc 480
taatgaggag ctgcgg 496

<210> SEQ ID NO 41
<211> LENGTH: 18
<212> TYPE: DNA
<213> ORGANISM: H. sapiens

<400> SEQUENCE: 41
gtgtctgaca gtggcgta 18

<210> SEQ ID NO 42
<211> LENGTH: 18
<212> TYPE: DNA
<213> ORGANISM: H. sapiens

<400> SEQUENCE: 42
tttgcccagg cagaacca 18

<210> SEQ ID NO 43
<211> LENGTH: 18
<212> TYPE: DNA
<213> ORGANISM: H. sapiens

<400> SEQUENCE: 43
ccacccaagg tcacgact 18

<210> SEQ ID NO 44
<211> LENGTH: 18
<212> TYPE: DNA
<213> ORGANISM: H. sapiens

<400> SEQUENCE: 44
atgccacgga ctaagacc 18

<210> SEQ ID NO 45
<211> LENGTH: 41
<212> TYPE: DNA
<213> ORGANISM: H. sapiens

<400> SEQUENCE: 45

-continued ggaattcgtc gaccaccatg catcctcaag tggtcatctt a 41

<210> SEQ ID NO 46
<211> LENGTH: 42
<212> TYPE: DNA
<213> ORGANISM: H. sapiens

<400> SEQUENCE: 46
ggaattcgcg gccgctcatt agtccgtggc ataaacagta tt 42

<210> SEQ ID NO 47
<211> LENGTH: 20
<212> TYPE: DNA
<213> ORGANISM: H. sapiens

<400> SEQUENCE: 47
tcaagtggtc atcttaagcc 20

<210> SEQ ID NO 48
<211> LENGTH: 22
<212> TYPE: DNA
<213> ORGANISM: H. sapiens

<400> SEQUENCE: 48
taaactctca aagagcacca ct 22

<210> SEQ ID NO 49
<211> LENGTH: 22
<212> TYPE: DNA
<213> ORGANISM: H. sapiens

<400> SEQUENCE: 49
acagactcca gcatagattc ct 22

<210> SEQ ID NO 50
<211> LENGTH: 22
<212> TYPE: DNA
<213> ORGANISM: H. sapiens

<400> SEQUENCE: 50
gcaccaagac agaaatacag ac 22

<210> SEQ ID NO 51
<211> LENGTH: 31
<212> TYPE: DNA
<213> ORGANISM: H. sapiens

<400> SEQUENCE: 51
agaagcaccc aagacagaaa tacagactcc a 31

<210> SEQ ID NO 52
<211> LENGTH: 19
<212> TYPE: DNA
<213> ORGANISM: H. sapiens

<400> SEQUENCE: 52
ttctagctgg gcaatgacc 19

<210> SEQ ID NO 53
<211> LENGTH: 20
<212> TYPE: DNA
<213> ORGANISM: H. sapiens

<400> SEQUENCE: 53
ccgcagctcc tcattagaag 20

<210> SEQ ID NO 54
<211> LENGTH: 307
<212> TYPE: PRT
<213> ORGANISM: rattus norvegicus

<400> SEQUENCE: 54

Met Val Gln Leu Gln Val Phe Ile Ser Gly Leu Leu Leu Leu Leu Pro
1 5 10 15

Gly Ser Val Asp Ser Tyr Glu Val Val Lys Gly Val Val Gly His Pro
20 25 30

Val Thr Ile Pro Cys Thr Tyr Ser Thr Arg Gly Gly Ile Thr Thr Thr
35 40 45

Cys Trp Gly Arg Gly Gln Cys Pro Tyr Ser Ser Cys Gln Asn Ile Leu
50 55 60

Ile Trp Thr Asn Gly Tyr Gln Val Thr Tyr Arg Ser Ser Gly Arg Tyr
65 70 75 80

Asn Ile Lys Gly Arg Ile Ser Glu Gly Asp Val Ser Leu Thr Ile Glu
85 90 95

Asn Ser Val Asp Ser Asp Ser Gly Leu Tyr Cys Cys Arg Val Glu Ile
100 105 110

Pro Gly Trp Phe Asn Asp Gln Lys Met Thr Phe Ser Leu Glu Val Lys
115 120 125

Pro Glu Ile Pro Thr Ser Pro Pro Thr Arg Pro Thr Thr Thr Arg Pro
130 135 140

Thr Thr Thr Arg Pro Thr Thr Ile Ser Thr Arg Ser Thr His Val Pro
145 150 155 160

Thr Ser Thr Arg Val Ser Thr Ser Thr Pro Thr Pro Glu Gln Thr Gln
165 170 175

Thr His Lys Pro Glu Ile Thr Thr Phe Tyr Ala His Glu Thr Thr Ala
180 185 190

Glu Val Thr Glu Thr Pro Ser Tyr Thr Pro Ala Asp Trp Asn Gly Thr
195 200 205

Val Thr Ser Ser Glu Glu Ala Trp Asn Asn His Thr Val Arg Ile Pro
210 215 220

Leu Arg Lys Pro Gln Arg Asn Pro Thr Lys Gly Phe Tyr Val Gly Met
225 230 235 240

Ser Val Ala Ala Leu Leu Leu Leu Leu Leu Ala Ser Thr Val Val Val
245 250 255

Thr Arg Tyr Ile Ile Ile Arg Lys Lys Met Gly Ser Leu Ser Phe Val
260 265 270

Ala Phe His Val Ser Lys Ser Arg Ala Leu Gln Asn Ala Ala Ile Val
275 280 285

His Pro Arg Ala Glu Asp Asn Ile Tyr Ile Ile Glu Asp Arg Ser Arg
290 295 300

Gly Ala Glu
305

<210> SEQ ID NO 55
<211> LENGTH: 451
<212> TYPE: PRT
<213> ORGANISM: Chlorocebus aethiops

<400> SEQUENCE: 55

Met His Leu Gln Val Val Ile Leu Ser Leu Ile Leu His Leu Ala Asp
1 5 10 15

-continued

```
Ser Val Ala Asp Ser Val Asn Val Asp Gly Val Ala Gly Leu Ser Ile
            20                  25                  30

Thr Leu Pro Cys Arg Tyr Asn Gly Ala Ile Thr Ser Met Cys Trp Asn
        35                  40                  45

Arg Gly Thr Cys Ser Val Phe Ser Cys Pro Asp Gly Ile Val Trp Thr
    50                  55                  60

Asn Gly Thr His Val Thr Tyr Arg Lys Glu Thr Arg Tyr Lys Leu Leu
65                  70                  75                  80

Gly Asn Leu Ser Arg Arg Asp Val Ser Leu Thr Ile Ala Asn Thr Ala
                85                  90                  95

Val Ser Asp Ser Gly Ile Tyr Cys Cys Arg Val Lys His Ser Gly Trp
            100                 105                 110

Phe Asn Asp Met Lys Ile Thr Ile Ser Leu Lys Ile Gly Pro Pro Arg
        115                 120                 125

Val Thr Thr Pro Ile Val Arg Thr Val Arg Thr Ser Thr Thr Val Pro
    130                 135                 140

Thr Thr Thr Thr Leu Pro Thr Thr Thr Thr Leu Pro Thr Thr Thr Thr
145                 150                 155                 160

Leu Pro Thr Thr Thr Thr Leu Pro Met Thr Thr Thr Leu Pro Met Thr
                165                 170                 175

Thr Thr Leu Pro Thr Thr Thr Thr Val Pro Thr Thr Thr Thr Leu Pro
            180                 185                 190

Thr Thr Thr Thr Leu Pro Thr Thr Leu Pro Met Thr Thr Thr Leu Pro
        195                 200                 205

Thr Thr Arg Thr Leu Pro Thr Thr Thr Thr Leu Pro Thr Thr Met Thr
    210                 215                 220

Leu Pro Met Thr Thr Thr Leu Pro Thr Thr Thr Thr Leu Pro Thr Thr
225                 230                 235                 240

Thr Thr Leu Pro Thr Thr Thr Leu Pro Thr Met Thr Leu Pro Thr Thr
                245                 250                 255

Thr Thr Leu Pro Thr Met Met Thr Leu Pro Thr Thr Thr Thr Leu Pro
            260                 265                 270

Thr Thr Thr Thr Leu Pro Thr Thr Thr Met Val Ser Thr Phe Val Pro
        275                 280                 285

Pro Thr Pro Leu Pro Met Gln Asn His Glu Pro Val Ala Thr Ser Pro
    290                 295                 300

Ser Ser Pro Gln Pro Ala Glu Thr His Pro Val Thr Leu Leu Gly Ala
305                 310                 315                 320

Thr Arg Thr Gln Pro Thr Ser Ser Pro Leu Tyr Ser Tyr Thr Thr Asp
                325                 330                 335

Gly Ser Asp Thr Val Thr Glu Ser Ser Asp Gly Leu Trp Asn Asn Asn
            340                 345                 350

Gln Thr Gln Leu Ser Pro Glu His Ser Pro Gln Met Val Asn Thr Thr
        355                 360                 365

Glu Gly Ile Tyr Ala Gly Val Cys Ile Ser Val Leu Val Leu Leu Ala
    370                 375                 380

Val Leu Gly Val Val Ile Ala Lys Lys Tyr Phe Phe Lys Lys Glu Ile
385                 390                 395                 400

Gln Gln Leu Ser Val Ser Phe Ser Asn His Gln Phe Lys Thr Leu Gln
                405                 410                 415

Asn Ala Val Lys Lys Glu Val His Ala Glu Asp Asn Ile Tyr Ile Glu
            420                 425                 430

Asn Asn Leu Tyr Ala Met Asn Gln Asp Pro Val Val Leu Phe Glu Ser
```

```
        435                 440                 445

Leu Arg Pro
    450


<210> SEQ ID NO 56
<211> LENGTH: 359
<212> TYPE: PRT
<213> ORGANISM: H. sapiens

<400> SEQUENCE: 56

Met His Pro Gln Val Val Ile Leu Ser Leu Ile Leu His Leu Ala Asp
 1               5                  10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
    50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
        115                 120                 125

Val Thr Thr Thr Pro Ile Val Thr Thr Val Pro Thr Val Thr Thr Val
    130                 135                 140

Arg Thr Ser Thr Thr Val Pro Thr Thr Thr Thr Val Pro Thr Thr Thr
145                 150                 155                 160

Val Pro Thr Thr Met Ser Ile Pro Thr Thr Thr Thr Val Pro Thr Thr
                165                 170                 175

Met Thr Val Ser Thr Thr Thr Ser Val Pro Thr Thr Thr Ser Ile Pro
            180                 185                 190

Thr Thr Thr Ser Val Pro Val Thr Thr Thr Val Ser Thr Phe Val Pro
        195                 200                 205

Pro Met Pro Leu Pro Arg Gln Asn His Glu Pro Val Ala Thr Ser Pro
    210                 215                 220

Ser Ser Pro Gln Pro Ala Glu Thr His Pro Thr Thr Leu Gln Gly Ala
225                 230                 235                 240

Ile Arg Arg Glu Pro Thr Ser Ser Pro Leu Tyr Ser Tyr Thr Thr Asp
                245                 250                 255

Gly Asn Asp Thr Val Thr Glu Ser Ser Asp Gly Leu Trp Asn Asn Asn
            260                 265                 270

Gln Thr Gln Leu Phe Leu Glu His Ser Leu Leu Thr Ala Asn Thr Thr
        275                 280                 285

Lys Gly Ile Tyr Ala Gly Val Cys Ile Ser Val Leu Val Leu Leu Ala
    290                 295                 300

Leu Leu Gly Val Ile Ile Ala Lys Lys Tyr Phe Phe Lys Lys Glu Val
305                 310                 315                 320

Gln Gln Leu Ser Val Ser Phe Ser Ser Leu Gln Ile Lys Ala Leu Gln
                325                 330                 335

Asn Ala Val Glu Lys Glu Val Gln Ala Glu Asp Asn Ile Tyr Ile Glu
            340                 345                 350

Asn Ser Leu Tyr Ala Thr Asp
```

-continued

```
355


<210> SEQ ID NO 57
<211> LENGTH: 6
<212> TYPE: PRT
<213> ORGANISM: H. sapiens

<400> SEQUENCE: 57

Met Thr Thr Thr Val Pro
 1               5


<210> SEQ ID NO 58
<211> LENGTH: 7
<212> TYPE: PRT
<213> ORGANISM: H. sapiens

<400> SEQUENCE: 58

Ser Val Val Tyr Gly Leu Arg
 1               5


<210> SEQ ID NO 59
<211> LENGTH: 7
<212> TYPE: PRT
<213> ORGANISM: mouse

<400> SEQUENCE: 59

Arg Ala Glu Asp Asn Ile Tyr
 1               5


<210> SEQ ID NO 60
<211> LENGTH: 14
<212> TYPE: PRT
<213> ORGANISM: mouse

<400> SEQUENCE: 60

Ser Arg Ala Glu Asp Asn Ile Tyr Ile Val Glu Asp Arg Pro
 1               5                   10


<210> SEQ ID NO 61
<211> LENGTH: 9
<212> TYPE: PRT
<213> ORGANISM: mouse

<400> SEQUENCE: 61

Arg Thr Arg Cys Glu Asp Gln Val Tyr
 1               5
```

MODULATION OF TIM RECEPTOR ACTIVITY IN COMBINATION WITH CYTOREDUCTIVE THERAPY

BACKGROUND OF THE INVENTION

The T cell/transmembrane, immunoglobulin, and mucin (TIM) gene family was positionally cloned in 2001 using a congenic mouse model of asthma. Since that time, a great deal of evidence has accumulated indicating that this gene family plays a critical role in regulating immune responses, including transplant tolerance, autoimmunity, the regulation of allergy and asthma, and the response to viral infections.

The TIM gene family consists of eight members (TIM-1-8) on mouse chromosome 11B1.1, and three members (TIM-1, TIM-3, and TIM-4) on human chromosome 5q33.2, located in a chromosomal region that has been repeatedly linked with asthma, allergy, and autoimmunity. Expression, function, and structural studies confirm that mouse TIM-1, TIM-3, and TIM-4 are the orthologues of human TIM-1, TIM-3, and TIM-4, respectively. TIM genes encode type I cell-surface glycoproteins with common structural features including an N-terminal immunoglobulin (Ig)-like domain, a mucin domain with O-linked glycosylations and with N-linked glycosylations close to the membrane, a single transmembrane domain, and a cytoplasmic region with tyrosine phosphorylation motif(s), except in TIM-4.

TIM-1, TIM-3, and TIM-4 are pattern recognition receptors specialized for recognition of phosphatidylserine (PtdSer). PtdSer is normally localized to the inner leaflet of the plasma membrane but is redistributed and exposed on the outer membrane when a cell undergoes apoptosis. PtdSer on apoptotic cells provides a key signal that triggers cell engulfment. Recognition of apoptotic cells is an essential component of tissue homeostasis and immune regulation.

TIM-1, TIM-3, and TIM-4 differ in molecular structure and expression patterns, suggesting that they have distinct functions in regulating T-cell responses. TIM-1, an important susceptibility gene for asthma and allergy, is preferentially expressed on Th2 cells and functions as a potent costimulatory molecule for T-cell activation. TIM-3 is preferentially expressed on T-helper 1 (Th1) and Tc1 cells and generates an inhibitory signal resulting in apoptosis of Th1 and Tc1 cells. Polymorphisms in TIM-1 and TIM-3 may reciprocally regulate the direction of T-cell responses. TIM-3 is also expressed on some dendritic cells (DCs) and can mediate phagocytosis of apoptotic cells and cross-presentation of antigen. In contrast, TIM-4 is exclusively expressed on antigen-presenting cells (APCs), where it mediates phagocytosis of apoptotic cells and plays an important role in maintaining tolerance. TIM molecules thus provide a functional repertoire for recognition of apoptotic cells, which determines whether apoptotic cell recognition leads to immune activation or tolerance, depending on the TIM molecule engaged and the cell type on which it is expressed.

The development of therapies relating to this gene family is of great clinical interest. The present invention addresses this issue.

RELATED PUBLICATIONS

The genetic sequence of the human hepatitis virus A cellular receptor may be found in Genbank, accession number XM_011327. A related sequence is provided in Genbank, accession number BAB55044. Monney et al. (2002) Nature 415:436 describe cell surface molecules expressed on Th1 cells. U.S. Pat. Nos. 5,721,351, U.S. Pat. No. 6,204,371, U.S. Pat. No. 6,288,218 relate to sequences corresponding to a mouse TIM-3 allele.

SUMMARY OF THE INVENTION

Compositions and methods are provided for the treatment of cancer. In the methods of the invention, administration of a cytoreductive agent or therapy, which include without limitation radiation therapy, e.g. local tumor radiation therapy; chemotherapy; and the like; in combination with administration of an effective dose of an agent that is an modulator of one or more TIM receptors, e.g. TIM-1, TIM-3 and TIM-4. In some embodiments the TIM modulator is a TIM-1 agonist, including without limitation, activating antibodies. In some embodiments the TIM modulator is a TIM-3 antagonist, including without limitation inhibitory antibodies. In some embodiments the TIM modulator is a TIM-4 agonist, including without limitation, activating antibodies.

The dose of TIM modulator may be sufficient to enhance the anti-proliferative effects of the cytoreductive therapy on the targeted tumor, for example where the reduction in viable tumor cells following treatment is greater than the reduction in the absence of the TIM modulator. The combination of TIM modulator and cytoreductive therapy may be synergistic, where the effectiveness of the combination is greater than the additive activity of the TIM modulator or the cytoreductive therapy administered as a single modality.

The dose of TIM modulator may be sufficient to reduce the side effects of the cytoreductive therapy on the patient, for example where there is a reduction in radiation-induced pneumonitis, hepatitis, and other radiation-specific effects following treatment, relative to the side-effects in the absence of the TIM modulator.

In some embodiment of the invention, the administration of a TIM modulator is guided by imaging with a phosphatidylserine (PS)-binding agent, e.g. annexin V peptides, TIM fusion proteins or fragments, etc., where the PS binding agent may be labeled for imaging, e.g. PET, SPECT, fluorescence, etc. The binding agent is brought into contact with the target tumor cells, where the presence of bound agent is indicative of PS being present, and thus is indicative of the potential to activate TIM receptors on immune cells.

Genetic sequences of a gene family encoding polypeptides associated with immune function and cell survival are provided. These genes encode cell surface molecules with conserved IgV and mucin domains, herein referred to as T cell Immunoglobulin domain and Mucin domain (TIM) proteins. The locus comprising the TIM family is genetically associated with immune dysfunction, including asthma. Furthermore, the TIM gene family is located within a region of human chromosome 5 that is commonly deleted in malignancies and myelodysplastic syndrome. Polymorphisms are identified in TIM-1, TIM-3 and TIM-4, which can be associated with Th1/Th2 differentiation and airway hyperresponsiveness (AHR).

The nucleic acid compositions are used to produce the encoded proteins, which may be employed for functional studies, as a therapeutic, and in studying associated physiological pathways. TIM specific binding agents, including nucleic acids, antibodies, and the like, are useful as diagnostics for determining genetic susceptibility to atopy and asthma and as diagnostics for assessing tumor resistance to cancer therapy. TIM blocking agents find use as therapeutics in the treatment of immune dysfunction and disorders of cell survival, including malignancies.

BRIEF DESCRIPTION OF THE DRAWINGS

FIG. 3*a*. IL-4 production by N2 mice is bimodal, with peaks corresponding to F1 and HBA phenotypes. As a means of evaluating the relative phenotypes of recombinant N2 mice in multiple experiments, we utilized an indexing function that allowed us to consolidate data from multiple experiments. A histogram shows a bimodal distribution of IL-4 index values for N2 mice with (BALB×HBA) F1, HBA homozygous, and recombinant haplotypes indicated. Distributions associated with the F1 and HBA haplotypes are distinct (P<0.0001, paired Student's t-test). b. IL-4 regulation segregates with Kim1sscp. Recombinant N2 haplotypes were sorted by IL-4 index values into groups associated with high IL-4 phenotypes (index <0.35) and low IL-4 phenotypes (index >0.65). Each column of boxes represents a recombinant haplotype. Alleles for these haplotypes at loci between D11Mit269 to D11Mit154 are shaded according to genotype (dark=F1; pale=HBA). High IL-4 production segregates with four haplotypes (left), and low IL-4 production segregates with four haplotypes (right). The IL-4 phenotype is linked to Kim1sscp. c. AHR of N2 mice is bimodal, with peaks corresponding to F1 and HBA phenotypes. Index values calculated from Penh values are shown. The histogram shows a bimodal distribution of AHR index values for N2 mice. (BALB×HBA) F1, HBA homozygous, and recombinant haplotypes are indicated. Distributions associated with the F1 and HBA haplotypes are distinct (P<0.0001, paired student's t-test). d. AHR Regulatory Locus cosegregates with the IL-4 Regulatory Locus between D11Mit22 and D11Mit271. Recombinant N2 haplotypes were sorted by AHR index values into groups associated with high AHR phenotypes (index <0.35) and low AHR phenotypes (index >0.65). Each column of boxes represents a recombinant haplotype. Alleles for these haplotypes at loci between D11 Mit269 to D11Mit154 are shaded according to genotype (dark=F1; pale=HBA). High AHR segregates with four haplotypes (left), and low IL-4 production segregates with three haplotypes (right). The AHR regulatory locus is linked to Kim1sscp, between D11Mit271 and D11Mit22.

FIG. 5*a,b,c*. Identification novel TIM gene family and major polymorphisms in TIM-1 and TIM-3. FIG. 5*a* depicts the amino acid sequences of mouse TIM-1 (SEQ ID NO:1); rat KIM-1 (SEQ ID NO:54); human HAVcr-1 (SEQ ID NO:56) and monkey HAVcr-1 (SEQ ID NO: 55. FIG. 5B depicts an alignment of the amino acid sequences of mouse TIM-1 (SEQ ID NO:1), mouse TIM-2 (SEQ ID NO:5), and mouse a2-11 (SEQ ID NO:9). FIG. 5C depicts an alignment of TIM-1 variants, HBA (SEQ ID NO:3) and BALB/c (SEQ ID NO:1); and A2-11/TIM-3 variants, HBA (SEQ ID NO:11) and BALB/c (SEQ ID NO:9). Cloning of mouse TIM-1 and mouse TIM-2. Members of a gene family. Sequences of the mouse TIM gene family members are shown. Shaded boxes illustrate identity between two of the mouse TIM genes. Total RNA from conA-stimulated splenocytes was reverse transcribed using Gibco Superscript II. PCR products of full length Tim-3 cDNA were amplified, purified with Qiagen QIAquick PCR Purification reagents, and sequenced directly by Biotech Core (Mountain View, Calif.). PCR products for Tim-1 and Tim-2 cDNA were cloned into electrocompetent TOP10 cells with TOPO-XL cloning reagents (Invitrogen). Plasmids were purified with a standard alkaline lysis protocol. BALB/c and HBA plasmids were sequenced, as described. Homology of mouse TIM-1, rat KIM-1, and HAVcr-1. Identity with mouse TIM-1 is denoted by the shaded boxes. The approximate signal site is denoted by an open, inverted triangle and the Ig domain/mucin domain boundary is shown with a filled diamond. The predicted transmembrane domains are underlined. TIM-1 and TIM-3 sequences with major polymorphisms between BALB/c and HBA TIM-1 and TIM-3 shown.

DETAILED DESCRIPTION OF THE EMBODIMENTS

Figures 1A, 1B, 1C:
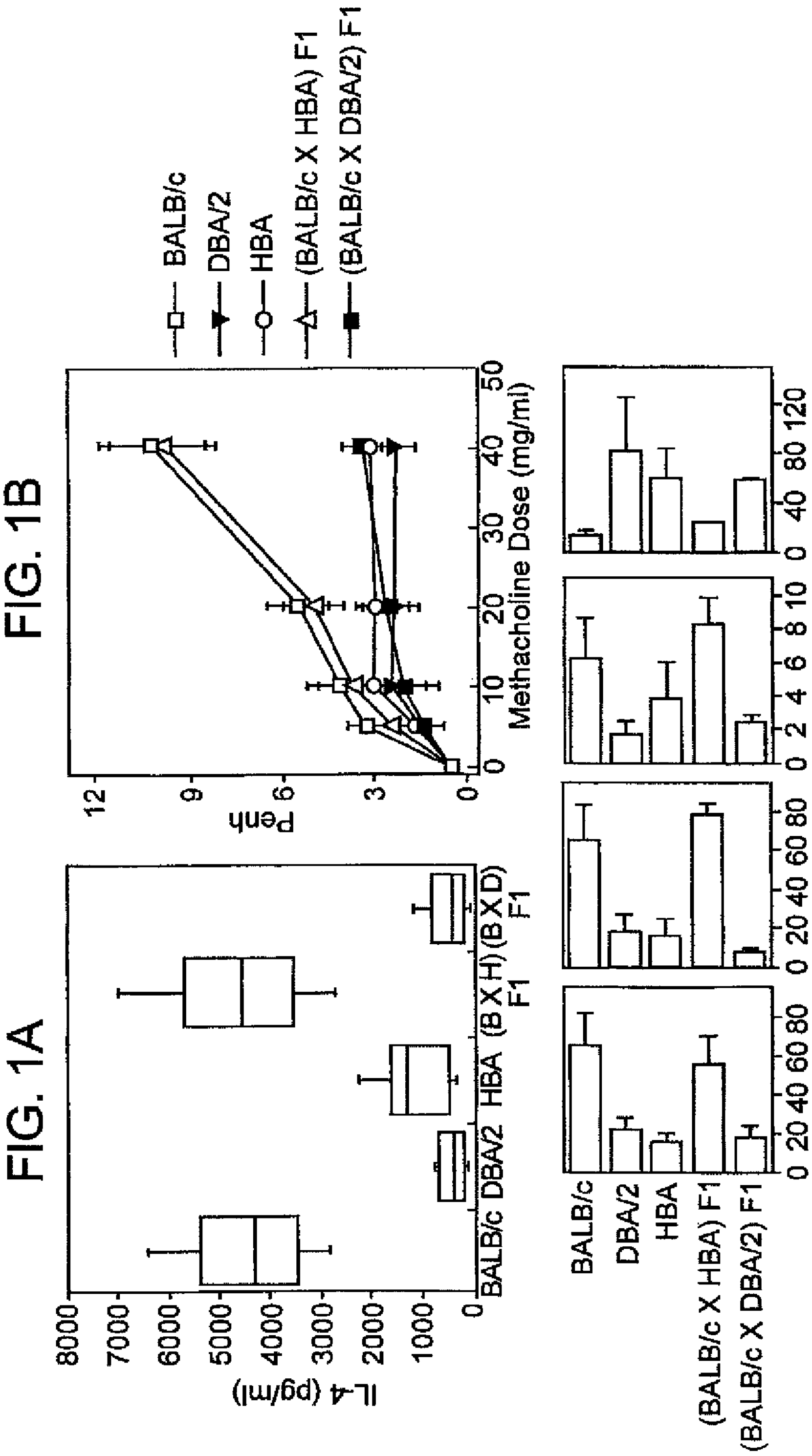
FIG. 1*a*, HBA mice produce significantly less IL-4 than do BALB/c mice. Lymph node cells of mice immunized with 150 μg of KLH were harvested, B-cell depleted, and cultured in cDME with 10 μg/ml KLH. Supernatants were harvested after 96 hours and assessed for IL-4 levels by ELISA. Shown is a box plot of IL-4 levels (n=10 in each group), representing the full range of data, with the boxes encompassing the upper and lower quartiles, with the median of the data set shown inside each box. IL-4 levels produced by BALB/c cells and by (BALB/c×HBA) F1 cells are significantly higher than HBA IL-4 levels P<0.0001 (student's t-test). b, HBA mice produce significantly less IL-13 and IL-10 than do BALB/c mice. Data shown are the average values of cytokines produced by lymph node cell cultures from ten individual mice in each experimental group, ±S.D. HBA IL-13 and IL-10 levels were lower than either the BALB/c or (BALB/c×HBA) F1 values, P<0.0001. HBA IL-5 versus BALB/c, P<0.05. HBA IFN-γ versus BALB/c, P<0.001. c, Allergen-induced airway hyperreactivity is significantly greater in BALB/c than do HBA mice. Pulmonary airflow obstruction was measured, and data shown represent peak enhanced pause (Penh) values averaged among sensitized mice in each group at various methacholine concentrations, ±S.E.M. (BALB×HBA) F1 demonstrate BALB/c phenotypes, while (BALB×DBA) F1 mice demonstrate DBA/2-like phenotypes.

New, more effective, and less toxic therapies are needed to treat cancer, including carcinomas such as breast cancer, prostate cancer and the like. The methods of the invention provide for a combination of cytoreductive therapy, including radiation therapy such as local tumor radiation therapy, which serves to kill irradiated cancer cells and releases antigens in close proximity to immune cells in tumors, with immunotherapy (IT), which promotes a local immune response against the irradiated tumor and leads the immune system to respond to sites of metastatic disease outside of the irradiation field.

Radiation therapy is known to enhance antigen presentation and T cell responses to antigen presenting cells. Factors controlling T cell activation by APCs presenting tumor antigen include TCR:MHC interaction, costimulation, and cytokines. Costimulation is determined by a collection of costimulatory and coinhibitory receptor/ligand pairs residing at the cell surfaces of T cells and antigen presenting cells. In order for an effective adaptive immune response to occur and to generate immune memory, costimulation is required. CD28, ICOS, HVEM, CD27, CD30, CD40L, OX40, 4-1 BB, TIM-1, and SLAM are major costimulatory receptors.

The methods of the invention utilize TIM receptor modulation as an immune therapy (IT) that, when combined with radiation (RT) or other cytoreductive therapy to the primary tumor site, enhances local cancer tumor control and reduces the size and number of distant cancer metastases. Since this approach uses RT to one site to kill disease at multiple sites, and uses the immune system to kill cancer cells throughout the body, it can reduce the need for RT to multiple sites of disease and additional chemotherapy.

Unlike locally administered adjuvants such as CpG oligonucleotides (CpG ODN), cytokines, or dendritic cells which typically require direct (invasive) tumoral manipulation, costimulation-enhancing monoclonal antibodies can be administered as a single dose intravenously and ‘boost’ the local response after RT without an invasive procedure. In this manner, an IT would be used concurrently with local RT directed at an internal tumor target or a single symptomatic metastasis, promote a RT-associated immune response, and generate a systemic (abscopal) immune response.

Because TIM receptors can be activated by binding to phosphatidylserine, a phospholipid that is exposed in irradiated tumor tissues, IT with TIM receptors may demonstrate greater specificity (and fewer ‘off target’ autoimmune side effects) than other IT agents currently under development, and the functional interaction between TIM-1 and PS in the tumor immune microenvironment provides a unique method for focusing immune activation to the irradiated tumor.

The TIM-1 gene and protein have several known polymorphisms that influence the function of the TIM-1 in immune responses. These genetic variations are most common in the mucin domain that is involved with TIM-1 adhesion to extracellular molecules and plays an important role in T helper cell function. Mice with functional deletions in exon 4 of TIM-1 develop less robust helper T cell responses. In human populations a polymorphism involving exon 4 encodes a longer form of the mucin chain, and this polymorphism impacts immune function. This polymorphism in TIM-1 has been linked to susceptibility to asthma and autoimmunity. Polymorphisms determining the length of the mucin domain may be analyzed prior to treatment involving stimulation of a TIM receptor.

Tumors of interest for treatment with the methods of the invention include solid tumors, e.g. carcinomas, gliomas, melanomas, sarcomas, and the like. Breast cancer is of particular interest. Carcinomas include the a variety of adenocarcinomas, for example in prostate, lung, etc.; adernocartical carcinoma; hepatocellular carcinoma; renal cell carcinoma, ovarian carcinoma, carcinoma in situ, ductal carcinoma, carcinoma of the breast, basal cell carcinoma; squamous cell carcinoma; transitional cell carcinoma; colon carcinoma; nasopharyngeal carcinoma; multilocular cystic renal cell carcinoma; oat cell carcinoma, large cell lung carcinoma; small cell lung carcinoma; etc. Carcinomas may be found in prostrate, pancreas, colon, brain (usually as secondary metastases), lung, breast, skin, etc. Including in the designation of soft tissue tumors are neoplasias derived from fibroblasts, myofibroblasts, histiocytes, vascular cells/endothelial cells and nerve sheath cells. Tumors of connective tissue include sarcomas; histiocytomas; fibromas; skeletal chondrosarcoma; extraskeletal myxoid chondrosarcoma; clear cell sarcoma; fibrosarcomas, etc.

Anti-proliferative, or cytoreductive therapy is used therapeutically to eliminate tumor cells and other undesirable cells in a host, and includes the use of therapies such as delivery of ionizing radiation, and administration of chemotherapeutic agents. Chemotherapeutic agents are well-known in the art and are used at conventional doses and regimens, or at reduced dosages or regimens, including for example, topoisomerase inhibitors such as anthracyclines, including the compounds daunorubicin, adriamycin (doxorubicin), epirubicin, idarubicin, anamycin, MEN 10755, and the like. Other topoisomerase inhibitors include the podophyllotoxin analogues etoposide and teniposide, and the anthracenediones, mitoxantrone and amsacrine. Other anti-proliferative agent interferes with microtubule assembly, e.g. the family of vinca alkaloids. Examples of vinca alkaloids include vinblastine, vincristine; vinorelbine (NAVELBINE); vindesine; vindoline; vincamine; etc. DNA-damaging agent include nucleotide analogs, alkylating agents, etc. Alkylating agents include nitrogen mustards, e.g. mechlorethamine, cyclophosphamide, melphalan (L-sarcolysin), etc.; and nitrosoureas, e.g. carmustine (BCNU), lomustine (CCNU), semustine (methyl-CCNU), streptozocin, chlorozotocin, etc. Nucleotide analogs include pyrimidines, e.g. cytarabine (CYTOSAR-U), cytosine arabinoside, fluorouracil (5-FU), floxuridine (FUdR), etc.; purines, e.g. thioguanine (6-thioguanine), mercaptopurine (6-MP), pentostatin, fluorouracil (5-FU) etc.; and folic acid analogs, e.g. methotrexate, 10-propargyl-5,8-dideazafolate (PDDF, CB3717), 5,8-dideazatetrahydrofolic acid (DDATHF), leucovorin, etc. Other chemotherapeutic agents of interest include metal complexes, e.g. cisplatin (cis-DDP), carboplatin, oxaliplatin, etc.; ureas, e.g. hydroxyurea; and hydrazines, e.g. N-methylhydrazine.

For example, ionizing radiation (IR) is used to treat about 60% of cancer patients, by depositing energy that injures or destroys cells in the area being treated, and for the purposes of the present invention may be delivered at conventional doses and regimens, or at reduced doses. Radiation injury to cells is nonspecific, with complex effects on DNA. The efficacy of therapy depends on cellular injury to cancer cells being greater than to normal cells. Radiotherapy may be used to treat every type of cancer. Some types of radiation therapy involve photons, such as X-rays or gamma rays. Another technique for delivering radiation to cancer cells is internal radiotherapy, which places radioactive implants directly in a tumor or body cavity so that the radiation dose is concentrated in a small area. A suitable dose of ionizing radiation may range from at least about 2 Gy to not more than about 10 Gy, usually about 5 Gy. A suitable dose of ultraviolet radiation may range from at least about 5 $J/m^2$ to not more than about 50 $J/m^2$, usually about 10 $J/m^2$. The sample may be collected from at least about 4 and not more than about 72 hours following ultraviolet radiation, usually around about 4 hours.

The TIM family genes are immediately adjacent to each other on human chromosome 5, in the order TIM-4, TIM-1, TIM-3, with no intervening genes. This segment of human chromosome 5 is commonly deleted in malignancies and dysplastic cell populations, as in myeolodysplastic syndrome (see Boultwood, et al, (1997) *Genomics* 45:88-96). There are TIM pseudogenes on chromosomes 5, 12, and 19. Each TIM protein, except TIM-4, contains a distinct predicted tyrosine signaling motif. The cytoplasmic region of TIM-1 contains two tyrosine residues and includes a highly conserved tyrosine kinase phosphorylation motif, (SEQ ID NO:59) RAEDNIY. The expanded region, (SEQ ID NO:60) SRAED-NIYIVEDRP, contains a predicted site for Itk phosphorylation and for EGF-receptor phosphorylation. The activity of TIM polypeptides may be modulated in order to direct immune function. TIM-1 is preferentially expressed in Th2 cells, and agents that modulate TIM-1 activity find use in the treatment of Th2 related disorders, including allergies, asthma, and the like. TIM-3 is preferentially expressed in Th1 cells, and agents that modulate TIM-3 activity find use in the treatment of pro-inflammatory immune diseases, including autoimmune diseases, graft rejection and the like.

Agents that modulate activity of TIM genes or proteins provide a point of therapeutic or prophylactic intervention, particularly agents that inhibit or upregulate activity of the polypeptide, or expression of the gene, particularly in combination with cytoreductive therapy. Numerous agents are useful in modulating this activity, including agents that directly modulate expression, e.g. expression vectors, antisense specific for the targeted polypeptide; and agents that act on the protein, e.g. specific antibodies and analogs thereof, small organic molecules that block catalytic activity, etc. The use of antibodies or specific binding fragments derived therefrom is of particular interest, e.g. antibodies specific for TIM-1, TIM-3 or TIM-4.

The compounds having the desired pharmacological activity may be administered in a physiologically acceptable carrier to a host to modulate TIM function, e.g. to enhance TIM function. The therapeutic agents may be administered in a variety of ways, orally, topically, parenterally e.g. intravenous, subcutaneously, intraperitoneally, by viral infection, intravascularly, etc. Intravenous delivery is of particular interest. Depending upon the manner of introduction, the compounds may be formulated in a variety of ways. The concentration of therapeutically active compound in the formulation may vary from about 0.1-100 wt. %.

In some embodiment of the invention, the administration of a TIM modulator is guided by imaging with a phosphatidylserine (PS)-binding agent, e.g. annexin V peptides, TIM fusion proteins or fragments, etc., where the PS binding agent may be labeled for imaging, e.g. PET, SPECT, fluorescence, etc. The binding agent is brought into contact with the target tumor cells, where the presence of bound agent is indicative of PS being present, and thus is indicative of the potential to activate TIM receptors on immune cells.

For example, Annexin V is a ubiquitous intracellular protein in humans that has a nanomolar affinity for the membrane-bound constitutive anionic phospholipid phosphatidylserine (PS), which is selectively expressed on the surface of apoptotic or physiologically stressed cells. As such, radiolabeled forms of annexin V have been used in both animal models and human Phase I and Phase II trials for utilizing the tracer as an early surrogate marker of therapeutic efficacy. For example see Blankenberg et al. (2009) Proc. Am. J. Thoracic. Soc. 6:469-476, herein specifically incorporated by reference. As the TIM proteins also bind to phosphatidylserine, the annexin V labeling is a useful surrogate, or other molecules that specifically bind to PS, e.g. TIM selective markers.

For example, the in vivo monitoring PS exposure (ie TIM target expression) after radiation therapy may be performed with anti-annexin V linked to a label radiotracer (for PET or SPECT), or with a TIM fusion protein linked to a label or radiotracer. Labels could include q-dots for near IR imaging, or other more conventional labels. pK/Kd studies may be performed with radiolabelled antibodies, using methods as described by Blankenberg for annexin V imaging.

The TIM modulatory agent may be administered prior to, concurrently with, or following the cytoreductive therapy, usually within at least about 1 week, at least about 5 days, at least about 3 days, at least about 1 day. The TIM modulatory agent may be delivered in a single dose, or may be fractionated into multiple doses, e.g. delivered over a period of time, including daily, bidaily, semi-weekly, weekly, etc. The effective dose will vary with the route of administration, the specific agent, the dose of cytoreductive agent, and the like, and may be determined empirically by one of skill in the art. A useful range for i.v. administered antibodies may be empirically determined, for example at least about 0.1 mg/kg body weight; at least about 0.5 mg/kg body weight; at least about 1 mg/kg body weight; at least about 2.5 mg/kg body weight; at least about 5 mg/kg body weight; at least about 10 mg/kg body weight; at least about 20 mg/kg body weight; or more.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

TIM Gene Family

The provided TIM family genes and fragments thereof, encoded proteins, genomic regulatory regions, and specific antibodies are useful in the identification of individuals predisposed to development or resistance to asthma, and for the modulation of gene activity in vivo for prophylactic and therapeutic purposes. The encoded proteins are useful as an immunogen to raise specific antibodies, in drug screening for compositions that mimic or modulate activity or expression, including altered forms of the proteins, and as a therapeutic.

The mouse Tim1 gene encodes a 305 amino acid membrane protein. The cytoplasmic region of TIM-1 contains two tyrosine residues and includes a highly conserved tyrosine kinase phosphorylation motif, RAEDNIY. The mucin domain of TIM-1 has multiple sites for O-linked glycosylation, and there two sites for N-linked glycosylation found in the immunoglobulin domain.

Mouse TIM-2, a similar 305 amino acid membrane protein, has 64% identity to mouse TIM-1, 60% identity to rat KIM-1, and 32% identity to hHAVcr-1. Like TIM-1, TIM-2 has two extracellular N-linked glycosylation sites and a serine, threonine-rich mucin domain with many O-linked glycosylation sites. TIM-2 also has an intracellular tyrosine kinase phosphorylation motif, (SEQ ID N0:61) RTRCEDQVY.

Tim3 encodes a 281 amino acid membrane protein in mice, and a 301 amino acid protein in humans, that has a similar, integral membrane glycoprotein structure with multiple extracellular glycosylation sites and an intracellular tyrosine phosphorylation motif. Although the mucin domain is not as prominent in TIM-3 as it is in TIM-1 and TIM-2, TIM-3 expressed on T cells interacts with a ligand on APCs and alters APC activation. TIM-3 has four sites for N-linked and five sites for O-linked glycosylation, suggesting that TIM-3, like TIM-1 and TIM-2, is heavily glycosylated and might interact with a ligand present on other cells, such as antigen presenting cells.

Tim4 encodes a 344 amino acid protein in mice, and a 378 amino acid protein in humans. The predicted TIM-4 also shares the general membrane glycoprotein structural motifs of the other TIM proteins, a with an IgV-like domain with highly conserved cysteine residues, a threonine-rich mucin-like domain, and a short intracellular tail.

Polymorphisms in the murine sequences are provided in the sequence listing for the BALB/c and HBA/DBA strains. In TIM-1, these polymorphisms encode three amino acid differences and a fifteen amino acid deletion in HBA/DBA. Seven predicted amino acid differences were identified in TIM-3. The polymorphisms in TIM-1 and TIM-4 are located in the signal and mucin-like domains, while the polymorphisms identified in TIM-3 are clustered in the Ig domain.

Figure 8:
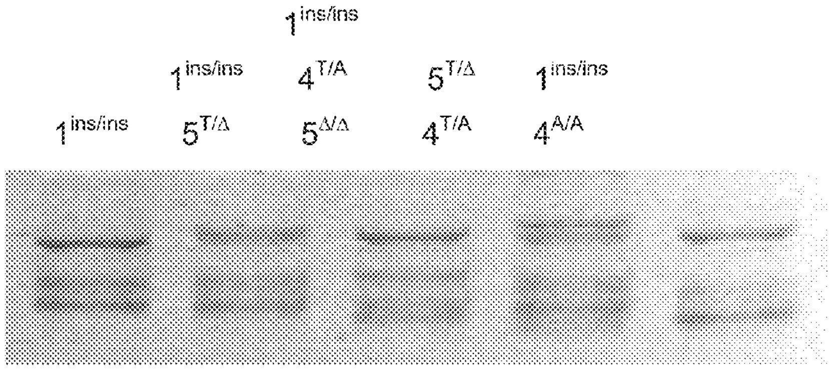
FIG. 8. SSCP polymorphism analysis of human TIM-1.

Variants in coding regions of human Tim1 are provided in the seqlist and FIG. 8. Variations include an insertion (labeled polymorphism 1), 157insMTTTVP, observed in 65% of the chromosomes, and a deletion (polymorphism 5), 187ΔThr, observed in 65% of the chromosomes. Other polymorphisms are T140A (polymorphism 7); V161A; (polymorphism 2); V167I (polymorphism 3); T172A (polymorphism 4); N258D (polypmorphism 6). Polymorphism 4 was observed in 40% of the chromosomes, and the other polymorphisms were each observed in ≤5% of the chromosomes. Most of these variations (2-6) are located within exon 3, the first mucin-encoding exon, and all of the variants occur at the genomic level and are not splice variants. The association between Tim1 and asthma susceptibility is further supported by reports of significant linkage of mite-sensitive childhood asthma to D5S820 (mean LOD score=4.8), a marker which is approximately 0.5 megabases from Tim1.

In human tissues, a 4.4 kb TIM-1 mRNA is present in almost all tissues, though it is faint in most. A 5.5-kb band was observed in colon and liver. A 7.5-kb band was observed in spleen, thymus, and peripheral blood leukocytes, and smaller than 4.4-kb bands were observed in some organs. TIM-1 mRNA is expressed with alternate 5' untranslated regions, in different cell populations. Hypoxia and ischemia induces TIM-1 expression in epithelial cells, and radiation induces expression of TIM gene family mRNA. The TIM genes are expressed in tumor specimens. Human TIM-4 mRNA is expressed in glioblastoma tissue, and is also detected in mitogen stimulated or irradiated peripheral blood monocytes.

In one aspect, the invention provides for an isolated nucleic acid molecule other than a naturally occurring chromosome comprising a sequence encoding a TIM-1, TIM-2, TIM-3 or TIM-4 protein, or a homolog or variant thereof, which variant may be associated with susceptibility to airway hyperreactivity and allergic T cell responses. The nucleic acid may be operably linked to a vector and/or control sequences for expression in a homologous or heterologous host cell. Such a host cell can find use in the production of the encoded protein. In another aspect of the invention, a purified polypeptide is provided of TIM-1, TIM-2, TIM-3 or TIM-4 protein, or a homolog or variant thereof, which variant may be associated with susceptibility to airway hyperreactivity and allergic T cell responses. In another aspect, an antibody or other specific binding member that binds to the TIM-1, TIM-2, TIM-3 or TIM-4 polypeptide is provided.

The DNA sequence encoding Tim polypeptides may be cDNA or genomic DNA or a fragment thereof. Fragments of interest for probes, producing polypeptides, etc. may comprise one or more polymorphic residues. The term Tim gene shall be intended to mean the open reading frame encoding any one of the specific Tim polypeptides, introns, as well as adjacent 5= and 3= non-coding nucleotide sequences involved in the regulation of expression, up to about 1 kb beyond the coding region, but possibly further in either direction. The gene may be introduced into an appropriate vector for extrachromosomal maintenance or for integration into the host.

In some embodiments, the Tim gene sequence is other than human TIM-1 allele 1, as set forth in the sequence listing; and/or other than mouse TIM-3 DBA allele.

The term "cDNA" as used herein is intended to include all nucleic acids that share the arrangement of sequence elements found in native mature mRNA species, where sequence elements are exons and 3= and 5= non-coding regions. Normally mRNA species have contiguous exons, with the intervening introns removed by nuclear RNA splicing, to create a continuous open reading frame encoding a Tim protein.

A genomic sequence of interest comprises the nucleic acid present between the initiation codon and the stop codon, as defined in the listed sequences, including all of the introns that are normally present in a native chromosome. It may further include the 3= and 5= untranslated regions found in the mature mRNA. It may further include specific transcriptional and translational regulatory sequences, such as promoters, enhancers, etc., including about 1 kb, but possibly more, of flanking genomic DNA at either the 5= or 3= end of the transcribed region. The genomic DNA may be isolated as a fragment of 100 kbp or smaller; and substantially free of flanking chromosomal sequence.

The sequence of the 5' region, and further 5' upstream sequences and 3' downstream sequences, may be utilized for promoter elements, including enhancer binding sites, that provide for expression in tissues where Tim genes are expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease. Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) *Mol Med* 1: 194-205; Mortlock et al. (1996) *Genome Res.* 6: 327-33; and Joulin and Richard-Foy (1995) *Eur J Biochem* 232: 620-626.

The regulatory sequences may be used to identify cis acting sequences required for transcriptional or translational regulation of TIM expression, especially in different tissues or stages of development, and to identify cis acting sequences and trans acting factors that regulate or mediate TIM expression. Such transcription or translational control regions may be operably linked to a TIM gene in order to promote expression of wild type or altered TIM or other proteins of interest in cultured cells, or in embryonic, fetal or adult tissues, and for gene therapy.

The nucleic acid compositions of the subject invention may encode all or a part of the subject polypeptides. Fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The TIM genes are isolated and obtained in substantial purity, generally as other than an intact mammalian chromosome. Usually, the DNA will be obtained substantially free of other nucleic acid sequences that do not include an TIM sequence or fragment thereof, generally being at least about 50%, usually at least about 90% pure and are typically Arecombinant@, i.e. flanked by one or more nucleotides with which it is not normally associated on a naturally occurring chromosome.

The DNA sequences are used in a variety of ways. They may be used as probes for identifying TIM related genes. Mammalian homologs have substantial sequence similarity to the subject sequences, i.e. at least 75%, usually at least 90%, more usually at least 95% sequence identity with the nucleotide sequence of the subject DNA sequence. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990) *J Mol Biol* 215:403-10.

Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity may be determined by hybridization under stringent conditions, for example, at 50° C. or higher and 0.1×SSC (9 mM saline/0.9 mM sodium citrate). By using probes, particularly labeled probes of DNA sequences, one can isolate homologous or related genes. The source of homologous genes may be any species, e.g. primate species, particularly human; rodents, such as rats and mice, canines, felines, bovines, ovines, equines, yeast, *Drosophila, Caenhorabditis, etc.*

The DNA may also be used to identify expression of the gene in a biological specimen. The manner in which one probes cells for the presence of particular nucleotide sequences, as genomic DNA or RNA, is well established in the literature and does not require elaboration here. mRNA is isolated from a cell sample. mRNA may be amplified by RT-PCR, using reverse transcriptase to form a complementary DNA strand, followed by polymerase chain reaction amplification using primers specific for the subject DNA sequences. Alternatively, mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of TIM gene expression in the sample.

The subject nucleic acid sequences may be modified for a number of purposes, particularly where they will be used intracellularly, for example, by being joined to a nucleic acid cleaving agent, e.g. a chelated metal ion, such as iron or chromium for cleavage of the gene; or the like.

The sequence of the TIM locus, including flanking promoter regions and coding regions, may be mutated in various ways known in the art to generate targeted changes in promoter strength, sequence of the encoded protein, etc. The DNA sequence or product of such a mutation will be substantially similar to the sequences provided herein, i.e. will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used. Such mutated genes may be used to study structure-function relationships of TIM polypeptides, or to alter properties of the protein that affect its function or regulation. For example, constitutively active transcription factors, or a dominant negatively active protein that binds to the TIM DNA target site without activating transcription, may be created in this manner.

Techniques for in vitro mutagenesis of cloned genes are known. Examples of protocols for scanning mutations may be found in Gustin et al., *Biotechniques* 14:22 (1993); Barany, *Gene* 37:111-23 (1985); Colicelli et al., *Mol Gen Genet.* 199:537-9 (1985); and Prentki et al., *Gene* 29:303-13 (1984). Methods for site specific mutagenesis can be found in Sambrook et al., *Molecular Cloning: A Laboratory Manual*, CSH Press 1989, pp. 15.3-15.108; Weiner et al., *Gene* 126:35-41 (1993); Sayers et al., *Biotechniques* 13:592-6 (1992); Jones and Winistorfer, *Biotechniques* 12:528-30 (1992); Barton et al., *Nucleic Acids Res* 18:7349-55 (1990); Marotti and Tomich, *Gene Anal Tech* 6:67-70 (1989); and *Zhu Anal Biochem* 177:120-4 (1989).

Arrays provide a high throughput technique that can assay a large number of polynucleotides in a sample. In one aspect of the invention, an array is constructed comprising one or more of the TIM genes, proteins or antibodies, preferably comprising all of these sequences, which array may further comprise other sequences known to be up- or down-regulated in T cells, monocytes, and the like. This technology can be used as a tool to test for differential expression, or for genotyping. Arrays can be created by spotting polynucleotide probes onto a substrate (e.g., glass, nitrocellulose, etc.) in a two-dimensional matrix or array having bound probes. The probes can be bound to the substrate by either covalent bonds or by non-specific interactions, such as hydrophobic interactions. Techniques for constructing arrays and methods of using these arrays are described in, for example, Schena et al. (1996) *Proc Natl Acad Sci USA.* 93(20):10614-9; Schena et al. (1995) *Science* 270(5235):467-70; Shalon et al. (1996) *Genome Res.* 6(7):639-45, U.S. Pat. No. 5,807,522, EP 799 897; WO 97/29212; WO 97/27317; EP 785 280; WO 97/02357; U.S. Pat. No. 5,593,839; U.S. Pat. No. 5,578,832; EP 728 520; U.S. Pat. No. 5,599,695; EP 721 016; U.S. Pat. No. 5,556,752; WO 95/22058; and U.S. Pat. No. 5,631,734.

The probes utilized in the arrays can be of varying types and can include, for example, synthesized probes of relatively short length (e.g., a 20-mer or a 25-mer), cDNA (full length or fragments of gene), amplified DNA, fragments of DNA (generated by restriction enzymes, for example) and reverse transcribed DNA. Both custom and generic arrays can be utilized in detecting differential expression levels. Custom arrays can be prepared using probes that hybridize to particular preselected subsequences of mRNA gene sequences or amplification products prepared from them.

Arrays can be used to, for example, examine differential expression of genes and can be used to determine gene function. For example, arrays can be used to detect differential expression, or expression of polymorphic sequences, in TIM genes. Exemplary uses of arrays are further described in, for example, Pappalarado et al. (1998) *Sem. Radiation Oncol.* 8:217; and Ramsay. (1998) *Nature Biotechnol.* 16:40. Furthermore, many variations on methods of detection using arrays are well within the skill in the art and within the scope of the present invention. For example, rather than immobilizing the probe to a solid support, the test sample can be immobilized on a solid support which is then contacted with the probe. Additional discussion regarding the use of microarrays in expression analysis can be found, for example, in Duggan, et al., Nature Genetics Supplement 21:10-14 (1999); Bowtell, Nature Genetics Supplement 21:25-32 (1999); Brown and Botstein, Nature Genetics Supplement 21:33-37 (1999); Cole et al., Nature Genetics Supplement 21:38-41 (1999); Debouck and Goodfellow, Nature Genetics Supplement 21:48-50 (1999); Bassett, Jr., et al., Nature Genetics Supplement 21:51-55 (1999); and Chakravarti, Nature Genetics Supplement 21:56-60 (1999).

Pharmacogenetics is the linkage between an individual's genotype and that individual's ability to metabolize or react to a therapeutic agent. Differences in metabolism or target sensitivity can lead to severe toxicity or therapeutic failure by altering the relation between bioactive dose and blood concentration of the drug. In the past few years, numerous studies have established good relationships between polymorphisms in metabolic enzymes or drug targets, and both response and toxicity. These relationships can be used to individualize therapeutic dose administration.

Genotyping of polymorphic alleles is used to evaluate whether an individual will respond well to a particular therapeutic regimen. The polymorphic sequences are also used in drug screening assays, to determine the dose and specificity of a candidate therapeutic agent. A candidate TIM polymorphism is screened with a target therapy to determine whether there is an influence on the effectiveness in treating asthma. Drug screening assays are performed as described above. Typically two or more different sequence polymorphisms are tested for response to a therapy.

The subject gene may be employed for synthesis of a complete TIM protein, or polypeptide fragments thereof, particularly fragments corresponding to functional domains; binding sites; etc.; and including fusions of the subject polypeptides to other proteins or parts thereof. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host.

Polypeptides of particular interest that are fragments of the TIM polypeptides include specific domains of the TIM polypeptides, where a domain may comprise, for example, the extracellular domain, or the domains within the extracellular domain: the mucin domain and/or the Ig domain. Domains may also comprise the cytoplasmic domain, e.g. a fragment encompassing the tyrosine kinase phosphorylation motif, (SEQ ID NO:59) RAEDNIY, or the expanded region, SEQ ID NO:60) SRAEDNIYIVEDRP. Polypeptides encoded by the soluble splice variants are also of interest. The sequence of the Ig domains are as follows: human TIM-1 Ig domain, SEQ ID NO: 17, 19, 21, 23, 25, 27, residues 21-126; human TIM-3 Ig domain, SEQ ID NO: 29 and 31, residues 22-131; human TIM-4 Ig domain, SEQ ID NO: 33 and 35, residues 25-133; mouse TIM-1 Ig domain, SEQ ID NO: 1 and 3, residues 21-129; mouse TIM-2 Ig domain, SEQ ID NO: 7, residues 22-128; mouse TIM-3 Ig domain, BALB/c allele, SEQ ID NO: 9, residues 22-132; mouse TIM-3 Ig domain, DBA/2 allele, SEQ ID No: 11, residues 22-132; mouse TIM-4 Ig domain, SEQ ID NO: 13 and 15, residues 25-135.

Functionally equivalent polypeptides may find use, where the equivalent polypeptide may contain deletions, additions or substitutions of amino acid residues that result in a silent change, thus producing a functionally equivalent differentially expressed on pathway gene product. Amino acid substitutions may be made on the basis of similarity in polarity, charge, solubility, hydrophobicity, hydrophilicity, and/or the amphipathic nature of the residues involved. "Functionally equivalent", as used herein, refers to a protein capable of exhibiting a substantially similar in vivo activity as the polypeptide encoded by a TIM gene.

The polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, or cells of a higher organism such as vertebrates, particularly mammals, e.g. COS 7 cells, may be used as the expression host cells. In many situations, it may be desirable to express the TIM gene in mammalian cells, where the TIM gene will benefit from native folding and post-translational modifications. Small peptides can also be synthesized in the laboratory, including specific peptide epitopes, domains, and the like, where peptides will usually be at least about 8 amino acids in length, more usually at least about 20 amino acids in length, up to complete domains, and the full length protein. Peptides may comprise polymorphic regions of the protein. Also included are fusion proteins, where all or a fragment of the TIM protein is fused to a heterologous polypeptide, e.g. green fluorescent protein, antibody Fc regions, poly-histidine, and the like.

In mammalian host cells, a number of viral-based expression systems may be used, including retrovirus, lentivirus, adenovirus, adeno-associated virus, and the like. In cases where an adenovirus is used as an expression vector, the coding sequence of interest can be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing differentially expressed or pathway gene protein in infected hosts.

Specific initiation signals may also be required for efficient translation of the genes. These signals include the ATG initiation codon and adjacent sequences. In cases where a complete gene, including its own initiation codon and adjacent sequences, is inserted into the appropriate expression vector, no additional translational control signals may be needed. However, in cases where only a portion of the gene coding sequence is inserted, exogenous translational control signals must be provided. These exogenous translational control signals and initiation codons can be of a variety of origins, both natural and synthetic. The efficiency of expression may be enhanced by the inclusion of appropriate transcription enhancer elements, transcription terminators, etc.

With the availability of the polypeptides in large amounts, by employing an expression host, the polypeptides may be isolated and purified in accordance with conventional ways. A lysate may be prepared of the expression host and the lysate purified using HPLC, exclusion chromatography, gel electrophoresis, affinity chromatography, or other purification technique. The purified polypeptide will generally be at least about 80% pure, preferably at least about 90% pure, and may be up to and including 100% pure. Pure is intended to mean free of other proteins, as well as cellular debris.

The polypeptide may be labeled, either directly or indirectly. Any of a variety of suitable labeling systems may be used, including but not limited to, radioisotopes such as $^{125}I$; enzyme labeling systems that generate a detectable colorimetric signal or light when exposed to substrate; and fluorescent labels. Indirect labeling involves the use of a protein, such as a labeled antibody, that specifically binds to the polypeptide of interest. Such antibodies include but are not limited to polyclonal, monoclonal, chimeric, single chain, Fab fragments and fragments produced by a Fab expression library.

Specific Binding Members

The term "specific binding member" or "binding member" as used herein refers to a member of a specific binding pair, i.e. two molecules, usually two different molecules, where one of the molecules (i.e., first specific binding member) through chemical or physical means specifically binds to the other molecule (i.e., second specific binding member). The complementary members of a specific binding pair are sometimes referred to as a ligand and receptor; or receptor and counter-receptor. For the purposes of the present invention, the two binding members may be known to associate with each other, for example where an assay is directed at detecting compounds that interfere with the association of a known binding pair. Alternatively, candidate compounds suspected of being a binding partner to a compound of interest may be used.

Specific binding pairs of interest include carbohydrates and lectins; complementary nucleotide sequences; peptide ligands and receptor; effector and receptor molecules; hormones and hormone binding protein; enzyme cofactors and enzymes; enzyme inhibitors and enzymes; lipid and lipid-binding protein; etc. The specific binding pairs may include analogs, derivatives and fragments of the original specific binding member. For example, a receptor and ligand pair may include peptide fragments, chemically synthesized peptidomimetics, labeled protein, derivatized protein, etc.

In a preferred embodiment, the specific binding member is an antibody, which may activate the TIM receptor, as an agonist antibody, or may inhibit the Tim receptor, as an inhibitor antibody. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. Antibodies that bind specifically to one of the TIM proteins are referred to as anti-TIM. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammal, chicken, other avians, etc., are considered to be "antibodies." Antibodies utilized in the present invention may be polyclonal antibodies, although monoclonal antibodies are preferred because they may be reproduced by cell culture or recombinantly, and can be modified to reduce their antigenicity.

Polyclonal antibodies can be raised by a standard protocol by injecting a production animal with an antigenic composition, which may be a polypeptide or a cDNA expressed in vivo. See, e.g., Harlow and Lane, Antibodies: A Laboratory Manual, Cold Spring Harbor Laboratory, 1988. When utilizing an entire protein, or a larger section of the protein, antibodies may be raised by immunizing the production animal with the protein and a suitable adjuvant (e.g., Fruend's, Fruend's complete, oil-in-water emulsions, etc.) When a smaller peptide is utilized, it is advantageous to conjugate the peptide with a larger molecule to make an immunostimulatory conjugate. Commonly utilized conjugate proteins that are commercially available for such use include bovine serum albumin (BSA) and keyhole limpet hemocyanin (KLH). In order to raise antibodies to particular epitopes, such as polymorphic residues, peptides derived from the full sequence may be utilized. The immunogen is injected into the animal host, preferably according to a predetermined schedule incorporating one or more booster immunizations, and the animals are bled periodically. Polyclonal antibodies may then be purified from such antisera by, for example, affinity chromatography using the polypeptide coupled to a suitable solid support.

Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. The immortal cell line utilized is preferably selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT).

In addition, the antibodies or antigen binding fragments may be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host (e.g. bacteria, insect cells, mammalian cells, or other suitable protein production host cell). When antibody gene synthesis is induced in the transfected host, the heavy and light chain proteins self-assemble to produce active antibodies that can be detected by screening with the antigen or immunogen.

Chimeric antibodies may be made by recombinant means by combining the murine variable light and heavy chain regions (VK and VH), obtained from a murine (or other animal-derived) hybridoma clone, with the human constant light and heavy chain regions, in order to produce an antibody with predominantly human domains. The production of such chimeric antibodies is well known in the art, and may be achieved by standard means (as described, e.g., in U.S. Pat. No. 5,624,659, incorporated fully herein by reference). Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

Alternatively, polyclonal or monoclonal antibodies may be produced from animals that have been genetically altered to produce human immunoglobulins. Techniques for generating such animals, and deriving antibodies therefrom, are described in U.S. Pat. Nos. 6,162,963 and 6,150,584, incorporated fully herein by reference.

Alternatively, single chain antibodies (Fv, as described below) can be produced from phage libraries containing human variable regions. See U.S. Pat. No. 6,174,708. Intrathecal administration of single-chain immunotoxin, LMB-7 [B3(Fv)-PE38], has been shown to cure of carcinomatous meningitis in a rat model. *Proc Natl. Acad. Sci. USA* 92, 2765-9, all of which are incorporated by reference fully herein.

In addition to entire immunoglobulins (or their recombinant counterparts), immunoglobulin fragments comprising the epitope binding site (e.g., Fab', $F(ab')_2$, or other fragments) are useful as antibody moieties in the present invention. Such antibody fragments may be generated from whole immunoglobulins by pepsin, papain, or other protease cleavage. "Fragment," or minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., poly-glycine or another sequence which does not form an alpha helix or beta sheet motif).

Fv fragments are heterodimers of the variable heavy chain domain ($V_H$) and the variable light chain domain ($V_L$). The heterodimers of heavy and light chain domains that occur in whole IgG, for example, are connected by a disulfide bond. Recombinant Fvs in which $V_H$ and $V_L$ are connected by a peptide linker are typically stable. These are single chain Fvs which have been found to retain specificity and affinity and have been shown to be useful for imaging tumors and to make recombinant immunotoxins for tumor therapy. However, researchers have bound that some of the single chain Fvs have a reduced affinity for antigen and the peptide linker can interfere with binding. Improved Fv's have been also been made which comprise stabilizing disulfide bonds between the $V_H$ and $V_L$ regions, as described in U.S. Pat. No. 6,147,203, incorporated fully herein by reference. Any of these minimal antibodies may be utilized in the present invention, and those which are humanized to avoid HAMA reactions are preferred for use in embodiments of the invention.

In addition, derivatized immunoglobulins with added chemical linkers, detectable moieties, such as fluorescent dyes, enzymes, substrates, chemiluminescent moieties and the like, or specific binding moieties, such as streptavidin, avidin, or biotin, and the like may be utilized in the methods and compositions of the present invention. For convenience, the term "antibody" or "antibody moiety" will be used throughout to generally refer to molecules which specifically bind to an epitope of the brain tumor protein targets, although the term will encompass all immunoglobulins, derivatives, fragments, recombinant or engineered immunoglobulins, and modified immunoglobulins, as described above.

Candidate antibodies can be tested for activity by any suitable standard means. As a first screen, the antibodies may be tested for binding against the immunogen. As a second screen, antibodies may be screened for cross-reactivity between alleles and between TIM family members, and tested for activity in inhibition of TIM function. For these screens, the candidate antibody may be labeled for detection. Antibodies that alter the biological activity of a TIM protein may be assayed in functional formats.

Diagnosis

Diagnosis of conditions associated with Tim polymorphisms is performed by protein, DNA or RNA sequence and/or hybridization analysis of any convenient sample from a patient, e.g. biopsy material, blood sample, scrapings from cheek, etc. A nucleic acid sample from a patient having a condition that may be associated with TIM, is analyzed for the presence of a polymorphism in TIM. A typical patient genotype would have at least one mutation on at least one chromosome. Individuals are screened by analyzing their DNA or mRNA for the presence of a predisposing polymorphism, as compared to an asthma neutral sequence. Specific sequences of interest include any polymorphism that leads to clinical bronchial hyperreactivity or is otherwise associated with asthma, including, but not limited to, insertions, substitutions and deletions in the coding region sequence, intron sequences that affect splicing, or promoter or enhancer sequences that affect the activity and expression of the protein. Examples of specific TIM polymorphisms are provided in the Examples.

Screening may also be based on the functional or antigenic characteristics of the protein. Immunoassays designed to detect predisposing polymorphisms in TIM proteins may be used in screening. Where many diverse mutations lead to a particular disease phenotype, functional protein assays have proven to be effective screening tools.

Biochemical studies may be performed to determine whether a candidate sequence polymorphism in the TIM coding region or control regions is associated with disease. For example, a change in the promoter or enhancer sequence that affects expression of TIM may result in predisposition to asthma. Expression levels of a candidate variant allele are compared to expression levels of the normal allele by various methods known in the art. Methods for determining promoter or enhancer strength include quantitation of the expressed natural protein; insertion of the variant control element into a vector with a reporter gene such as βBgalactosidase, luciferase, chloramphenicol acetyltransferase, etc. that provides for convenient quantitation; and the like. The activity of the encoded TIM protein may be determined by comparison with the wild-type protein.

A number of methods are available for analyzing nucleic acids for the presence of a specific sequence. Where large amounts of DNA are available, genomic DNA is used directly. Alternatively, the region of interest is cloned into a suitable vector and grown in sufficient quantity for analysis. Cells that express TIM genes, such as trachea cells, may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985) *Science* 239:487, and a review of current techniques may be found in Sambrook, et al. *Molecular Cloning: A Laboratory Manual*, CSH Press 1989, pp. 14.2B14.33. Amplification may also be used to determine whether a polymorphism is present, by using a primer that is specific for the polymorphism. Alternatively, various methods are known in the art that utilize oligonucleotide ligation as a means of detecting polymorphisms, for examples see Riley et al. (1990) *N.A.R.* 18:2887-2890; and Delahunty et al. (1996) *Am. J. Hum. Genet.* 58:1239-1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2=,7=-dimethoxy-4=,5=-dichloro-6-carboxyfluorescein (JOE), 6-carboxy-X-rhodamine (ROX), 6-carboxy-2=,4=,7=,4,7-hexachlorofluorescein (HEX), 5-carboxyfluorescein (5-FAM) or N,N,N==,N=-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a neutral TIM sequence. Hybridization with the variant sequence may also be used to determine its presence, by Southern blots, dot blots, etc. The hybridization pattern of a control and variant sequence to an array of oligonucleotide probes immobilised on a solid support, as described in U.S. Pat. No. 5,445,934, or in WO95/35505, may also be used as a means of detecting the presence of variant sequences. Single strand conformational polymorphism (SSCP) analysis, denaturing gradient gel electrophoresis (DGGE), mismatch cleavage detection, and heteroduplex analysis in gel matrices are used to detect conformational changes created by DNA sequence variation as alterations in electrophoretic mobility. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels.

The hybridization pattern of a control and variant sequence to an array of oligonucleotide probes immobilised on a solid support, as described in U.S. Pat. No. 5,445,934, or in WO95/35505, may be used as a means of detecting the presence of variant sequences. In one embodiment of the invention, an array of oligonucleotides are provided, where discrete positions on the array are complementary to at least a portion of mRNA or genomic DNA of the TIM locus. Such an array may comprise a series of oligonucleotides, each of which can specifically hybridize to a nucleic acid, e.g. mRNA, cDNA, genomic DNA, etc. from the TIM locus.

Antibodies specific for TIM polymorphisms may be used in screening immunoassays. A reduction or increase in neutral TIM and/or presence of asthma associated polymorphisms is indicative that asthma is TIM-associated. A sample is taken from a patient suspected of having TIM-associated asthma. Samples, as used herein, include biological fluids such as tracheal lavage, blood, cerebrospinal fluid, tears, saliva, lymph, dialysis fluid and the like; organ or tissue culture derived fluids; and fluids extracted from physiological tissues. Also included in the term are derivatives and fractions of such fluids. Biopsy samples are of particular interest, e.g. trachea scrapings, etc. The number of cells in a sample will generally be at least about $10^3$, usually at least $10^4$ more usually at least about $10^5$. The cells may be dissociated, in the case of solid tissues, or tissue sections may be analyzed. Alternatively a lysate of the cells may be prepared.

Diagnosis may be performed by a number of methods. The different methods all determine the absence or presence or altered amounts of normal or abnormal TIM in patient cells suspected of having a predisposing polymorphism in TIM. For example, detection may utilize staining of cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method for diagnosis depends on the in vitro detection of binding between antibodies and TIM in a lysate. Measuring the concentration of TIM binding in a sample or fraction thereof may be accomplished by a variety of specific assays. A conventional sandwich type assay may be used. For example, a sandwich assay may first attach TIM-specific antibodies to an insoluble surface or support. The particular manner of binding is not crucial so long as it is compatible with the reagents and overall methods of the invention. They may be bound to the plates covalently or non-covalently, preferably non-covalently.

Other immunoassays are known in the art and may find use as diagnostics. Ouchterlony plates provide a simple determination of antibody binding. Western blots may be performed on protein gels or protein spots on filters, using a detection system specific for TIM as desired, conveniently using a labeling method as described for the sandwich assay.

The TIM genes are useful for analysis of TIM expression, e.g. in determining developmental and tissue specific patterns of expression, and for modulating expression in vitro and in vivo. Vectors useful for introduction of the gene include plasmids and viral vectors. Of particular interest are retroviral-based vectors, e.g. Moloney murine leukemia virus and modified human immunodeficiency virus; adenovirus vectors, etc. that are maintained transiently or stably in mammalian cells. A wide variety of vectors can be employed for transfection and/or integration of the gene into the genome of the cells. Alternatively, micro-injection may be employed, fusion, or the like for introduction of genes into a suitable host cell. See, for example, Dhawan et al. (1991) *Science* 254:1509-1512 and Smith et al. (1990) *Molecular and Cellular Biology* 3268-3271.

The expression vector will have a transcriptional initiation region oriented to produce functional mRNA. The native transcriptional initiation region or an exogenous transcriptional initiation region may be employed. The promoter may be introduced by recombinant methods in vitro, or as the result of homologous integration of the sequence into a chromosome. Many strong promoters are known in the art, including the β-actin promoter, SV40 early and late promoters, human cytomegalovirus promoter, retroviral LTRs, methallothionein responsive element (MRE), tetracycline-inducible promoter constructs, etc.

Expression vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

Antisense molecules are used to down-regulate expression of TIM in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnology* 14:840-844).

Compound Screening

One can identify ligands or substrates that bind to, modulate or mimic the action of TIM. Areas of investigation are the development of treatments for immune disorders, asthma, cancer, ischemia-reperfusion injury, and other diseases that are associated with cellular responses to stress. Drug screening identifies agents that provide an inhibition, replacement, or enhancement for TIM function in affected cells. For example, agents that reverse or inhibit TIM function may reduce bronchial reactivity in asthma by reducing levels of Th2 cytokines, and TIM inhibitors may enhance tumor sensitivity to cancer therapy, by potentiating the effects of radiation and chemotherapeutic treatments that induce apoptosis. Of particular interest are screening assays for agents that have a low toxicity for human cells. A wide variety of assays may be used for this purpose, including labeled in vitro protein-protein binding assays, protein-DNA binding assays, electrophoretic mobility shift assays, immunoassays for protein binding, and the like. The purified protein may also be used for determination of three-dimensional crystal structure, which can be used for modeling intermolecular interactions, transcriptional regulation, etc.

The term "agent" as used herein describes any molecule, e.g. protein or pharmaceutical, with the capability of altering or mimicking the physiological function of TIM, such as a signal tyrosine kinase inhibitor, or a peptide inhibitor of an integrin binding site. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Other assays of interest detect agents that mimic TIM function. For example, candidate agents are added to a cell that lacks functional TIM, and screened for the ability to reproduce TIM in a functional assay.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms “a”, “and”, and “the” include plural referents unless the context clearly dictates otherwise. Thus, for example, reference to “a cell” includes a plurality of such cells and reference to “the array” includes reference to one or more arrays and equivalents thereof known to those skilled in the art, and so forth. All technical and scientific terms used herein have the same meaning as commonly understood to one of ordinary skill in the art to which this invention belongs unless clearly indicated otherwise.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

To analyze the human 5q23-35 region for asthma susceptibility genes, we utilized a mouse model, which offers several potential advantages. Environmental variation can be controlled, multiple phenotypes can be tested simultaneously, and inbred strains can be sensitized with allergen to develop airway hyperreactivity (AHR), a cardinal feature of human asthma. We utilized congenic inbred mouse strains that differed only by a small chromosomal region homologous to human chromosome 5q, thereby allowing this region to be studied in the absence of genetic variation outside the region. Positional cloning revealed a novel gene family encoding T cell membrane proteins (Tim), TIM-1, TIM-2, TIM-3, TIM-4, TIM-5, TIM-6, and TIM-7, in which major sequence variants of TIM-1, TIM-3, and TIM-4, cosegregate completely with Tapr.

IL-4 production and airway hyperreactivity are reduced in HBA mice. We examined congenic mice produced on a BALB/c genomic background with discrete genomic intervals inherited from individual DBA/2 chromosomes. BALB/c mice develop Th2 biased, atopy-resembling immune responses with enhanced AHR, while DBA/2 mice develop reduced IL-4 responses that protect against the development of AHR. By screening several of these congenic strains for reduced Th2 responsiveness, we identified one congenic line, C.D2 Es-Hba (HBA), which contained a segment of chromosome 11 inherited from DBA/2 mice, homologous to human 5q23-35. FIG. 1*a* shows that lymph node cells from immunized control BALB/c mice, as expected, produced high levels of IL-4, confirming the proclivity of BALB/c mice to develop Th2-biased immune responses. In contrast, lymph node cells from HBA mice produced significantly lower levels of IL-4, similar to that observed in DBA/2 mice. In addition, HBA mice produced significantly less IL-13 and IL-10, and somewhat lower levels of IL-5 compared to BALB/c mice, whereas production of IFN-γ was increased, as shown in FIG. 1*b*. These results indicated that the DBA/2-derived region of HBA chromosome 11, which has large regions of conserved synteny with human 5q23-35, contains a gene that reduces antigen-specific IL-4, IL-13, and IL-10 production, enhances IFN-γ production, and converts the BALB/c cytokine phenotype into a DBA/2 cytokine phenotype.

The HBA mice were examined for the capacity to develop antigen-induced airway hyperreactivity (AHR), which is associated with Th2-biased immune responses. Upon sensitization and challenge with allergen, control BALB/c mice developed high AHR, whereas similarly immunized HBA congenic mice, like DBA/2 mice, expressed normal airway reactivity in response to methacholine (FIG. 1*c*). Collectively, these results strongly suggested that genetic variation in a single locus on chromosome 11 regulated both Th2 cytokine production and AHR; therefore, we tentatively refer to the relevant genetic determinant(s) in HBA mice as a single locus, T cell and Airway Phenotype Regulator (Tapr).

We also examined (BALB/c×HBA) F1 mice, which like the BALB/c mice, produced high levels of IL-4, IL-13, and IL-10 (FIGS. 1*a* and 1*b*) and developed elevated antigen-induced AHR (FIG. 1*c*). These results indicate that a DBA/2 allele on chromosome 11, in isolation of other genes that regulate IL-4 synthesis, reduced IL-4 production and AHR in a recessive manner. In contrast, (BALB/c×DBA/2) F1 mice produced low levels of IL-4 and had normal airway responsiveness on immunization (FIG. 1), indicating that loci from other regions of the DBA genome also modulated IL-4 production and antigen-induced AHR, and that the DBA/2 alleles, in aggregate, functioned in a dominant manner to limit IL-4 production and AHR. These results underscore the multigenic, complex nature of atopic traits and demonstrate the potential advantages of using a congenic strain to isolate and characterize a single locus without interference from multiple epistatic genes that also influence the asthmatic phenotype.

Figure 2:
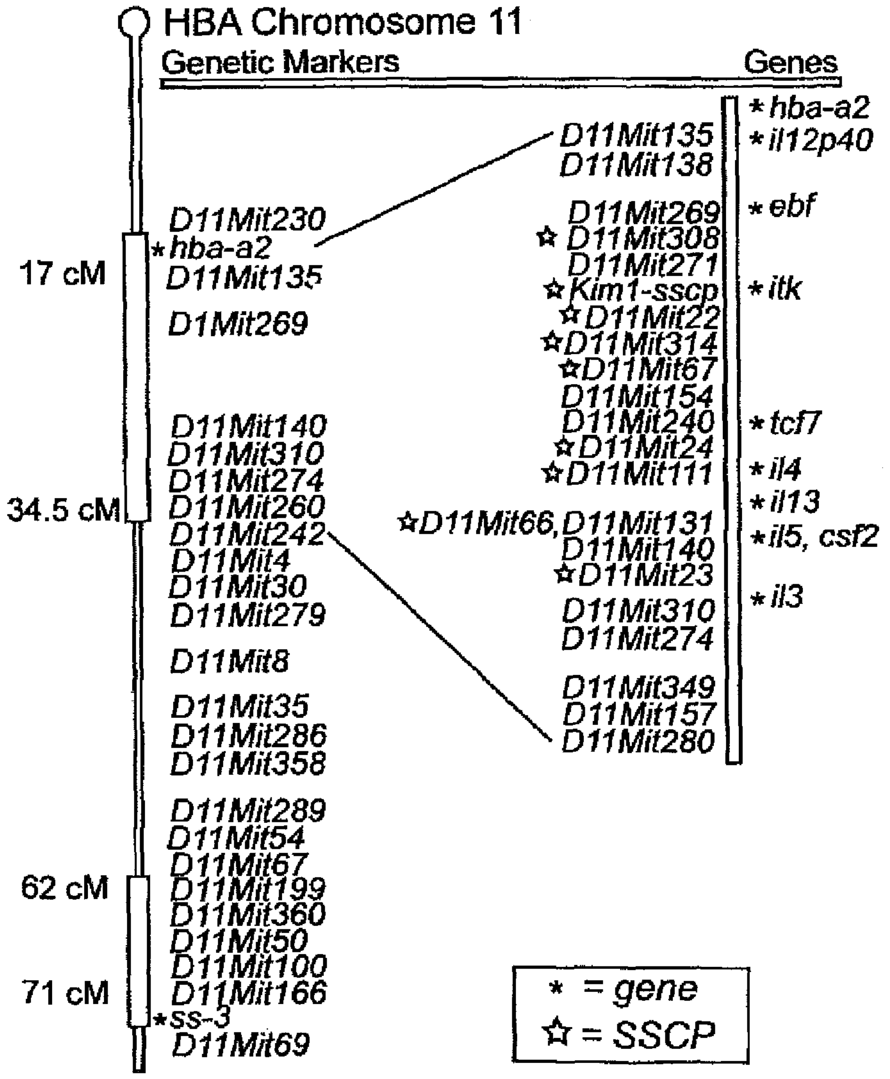
FIG. 2. Regions of HBA chromosome 11 were inherited from DBA/2. HBA chromosome 11 contains two regions derived from DBA between hba-α2 and es-3, as delineated by SSLP markers. The regions of HBA chromosome 11 with DBA/2 genotypes are highlighted (in blue) in the diagram to the left. The markers (left) provide 2-5 cM resolution distal to D11Mit230. Where the mouse chromosome 11 has regions of highly conserved synteny with 5q23-35, additional markers were identified with informative polymorphisms between BALB/c and DBA/2, to provide 0.01-2 cM resolution in this region (right column markers). Single-stranded confirmation polymorphisms (SSCP) markers are shown in green to distinguish them from the SSLP markers, and the positions of particular genes of interest, denoted in red, are also shown. Where the arrangement of our marker map differs from the Chromosome Committee Reports and the MIT linkage map, our map concurs with previous linkage and physical maps.

Genetic Mapping of Tapr, the locus which controls AHR and IL-4 responsiveness. Previously, the congenic region in the HBA mice was delineated with 36 genome-wide markers, including two chromosome 11 markers, hemoglobin-$\alpha$2 (hba-$\alpha$2) and esterase-3 (es-3) loci. The HBA genome, outside of chromosome 11, was inherited from BALB/c. A more precise analysis with 25 simple sequence length polymorphism (SSLP) markers known to be polymorphic between DBA/2 and BALB/c mice showed that HBA mice inherited two segments of chromosome 11 from DBA/2 (FIG. 2, left column). The proximal region contained a 20 cM segment with homology to chromosome 5q23-35, which afforded the possibility that a genetic locus implicated in human asthma linkage studies could be identified in a mouse model of asthma.

To map at higher resolution the $T_H$2-AHR controlling locus, Tapr, (BALB/c×HBA) FI mice were backcrossed to HBA mice to produce N2 animals. With this backcross approach, the set of alleles contributed by the HBA parent is pre-determined, and the set of alleles contributed by the F1 parent can be assessed by genotyping. Thus, recombination events that produce informative haplotypes within the congenic region can be detected in the N2 mice and used to assess the linkage of Tapr to loci in the congenic interval. Because of the recessive nature of Tapr, we tested N2 mice from these backcrosses to identify the minimum homozygous region of HBA-derived genes sufficient to confer the HBA Tapr phenotype. More than 2,000 N2 animals were generated and genotyped. Using SSLP markers, we selected those N2 mice with informative recombination events, and the N2 mice were phenotyped for the capacity to produce IL-4 in response to immunization with keyhole limpet hemocyanin (KLH). In this primary analysis, we determined that the relevant locus resided within the proximal congenic region, between D11Mit135 and D11Mit260. In order to map Tapr at higher resolution, 22 additional markers were identified and utilized to provide 0.1-1 cM resolution in the area of interest.

To accurately compare the results of IL-4 cytokine analyses performed over several months time, an IL-4 index for each experiment was generated for each N2 mouse, $$\left(\frac{B-x}{B-H}\right),$$

where B=IL-4 production by cells from BALB/c mice, H=IL-4 production by cells from HBA mice, and x=IL-4 production by cells from the N2 mouse being assessed. High concentrations of IL-4 (BALB/c-like) are represented by index values near 0, and low concentrations of IL-4 (HBA-like) are represented by index values near 1.0. The "B and "H" values were established with 3-5 control mice for each group of 3-6 N2 mice carrying informative recombinations that we tested. The index values fall within a bimodal distribution (FIG. 3*a*), in which the phenotype index associated with N2 mice that had nonrecombinant HBA genotypes was significantly higher (P<0.0001, in a paired Student's t-test) than the phenotype index associated with N2 mice that had nonrecombinant (BALB/c×HBA)F1 genotypes.

For the mice with unique genotypes, we used several methods to ensure the adequacy of single measurements of cytokine production and AHR, since this is critical in linkage analysis. First, at the same time that we tested each of the N2 mice carrying recombinations of interest, we also tested "non-recombinant" siblings of each "recombinant N2" that were strictly HBA or F1 (BALB×HBA) in genotype. Furthermore, we bred additional N3 mice by crossing some of the N2 mice carrying recombinations of interest back to HBA mice, in order to have more individual mice with that particular N2 genotype. All values were the average of the values for the individual mice tested with a given genotype. In this way, we are confident of the measures of cytokine production and AHR, and that we have overcome assay variations due to variables inherent in biological systems.

Because the IL-4 values associated with the N2 mice that inherited recombinant haplotypes segregated in a bimodal distribution (FIG. 3*a*), were able to demonstrate that the genetic locus that controls high IL-4 responses is located between markers D11Mit271 and D11Mit22 (FIG. 3*b*). Moreover, high levels of IL-4 production were observed in all mice with a BALB/c allele present at Kim1sscp, and low levels of IL-4 production were observed in all mice with homozygous HBA genotypes at Kim1sscp. Thus, Tapr was nonrecombinant with Kim1sscp, an intronic marker within a mouse homologue of *Rattus norvegicus* Kidney Injury Molecule (Kim-1). In contrast, Tapr segregated from all other markers with at least one recombination. The fact that Tapr and Kim1sscp segregated together, indicated that the Tapr locus is located very close to or is indistinguishable from Kim1sscp. Based on the frequency recombinant haplotypes between D11Mit271 and D11Mit22, we calculate a recombination frequency, 0.0039, which indicates that that the Tapr locus maps to a small, 0.3-0.5 cM, region. We also calculated a recombination frequency of 0.08 between Tapr and IL-4. Therefore, Tapr is located 5-10 cM away from the IL-4 cytokine cluster but is within the a region of the mouse genome that has highly conserved synteny with the 5q23-35 region that has been linked to human atopy and asthma.

Using an analogous approach, we examined the segregation of allergen-induced AHR phenotypes in mice with informative recombinant haplotypes. With indexed AHR values, N2 mice clearly exhibit parental phenotypes, which produced a bimodal distribution in a histogram of AHR index values in a group of sensitized N2 mice (FIG. 3*c*). By analyzing the segregation of AHR phenotypes associated with more than 1,000 N2 mice, we demonstrated that the genetic locus which controls AHR responses is also located between markers D11Mit271 and D11Mit22 (FIG. 3*d*) and that the AHR phenotype was nonrecombinant with Kim1sscp. Thus, we demonstrate that both IL-4 responsiveness and AHR cosegregate with the Tapr locus, which suggests that the same locus regulates both IL-4 expression and AHR (FIG. 3).

These findings further demonstrate that the Tapr locus is more than 5 cM centromeric to the IL-4 cytokine cluster and the cytokine genes in the cluster previously thought to be 'candidate' atopy or asthma susceptibility genes. Our mapping results also establish that Tapr is genetically separable from both the IL-12p40 gene and the region of mouse chromosome 11 that includes the $T_H$1-IL12 regulatory locus, Tpm.

Figure 4:
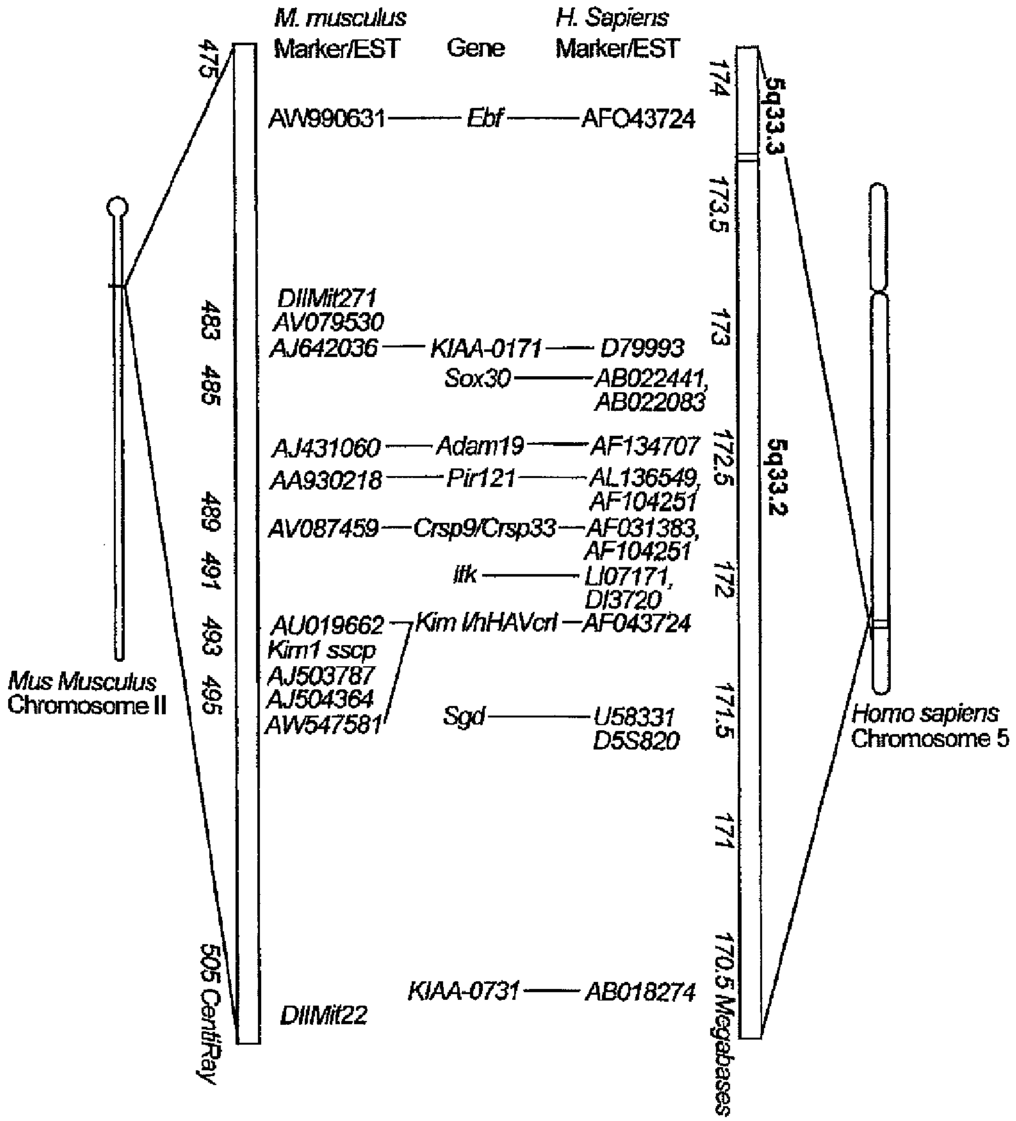
FIG. 4 Mouse chromosome 11 interval containing Tapr is highly homologous to 5q33. In order to construct a composite map around the Tapr locus, we integrated available information from the mouse linkage, backcross, and radiation hybrid maps and identified a region of highly conserved synteny in current maps of the human genome (Human Genome Browser v3, UCSC, March 2001). ESTs located on a physical map of mouse chromosome 11 (left) are denoted by their accession numbers and aligned by homology to genes (center), which correspond to ESTs on human chromosome 5 (right). All known genes between KIAA0171 and Sgd are shown.

Mouse and human homologues anchor Tapr to human 5q33. In order to construct a composite map around the Tapr locus, we integrated available information from the Mouse Genome Database (MGD) linkage, backcross, and radiation hybrid maps and identified a region of conserved synteny in maps of the human genome. Current radiation hybrid maps place the markers that are near D11Mit271 and D11Mit22, including several expressed sequence tags (ESTs) that have extensive homology to known genes or unigene clusters, onto a physical map of the mouse genome. We further examined these markers and their associated ESTs for previously unidentified similarity to known gene clusters. We assembled these markers onto a scaffold for comparison to the human genome. Using this approach, we found significant similarity between particular radiation hybrid markers and the following human genes: KIAA0171, Adam-19, Sox-30, Pir-121, Crsp9 (Crsp33), and hHAVcr-1 (hHAVcr-1). FIG. 4 demonstrates that once we anchored these genes to a physical map of the mouse genome between our flanking markers, we were able to locate those genes in the Human Genome Browser.

The high degree of conservation between the mouse and human genomes in this region indicates linkage of the Tapr locus to human 5q33.2. As shown FIG. 4, we identified all known genes and ESTs in this region of the human map. Genes of particular interest near human hHAV-cr and the mouse homologue of Kim-1, include IL-2 inducible T cell kinase (Itk) and a coregulator of the SP-1 transcription factor (Crsp9), both known to be involved in T cell differentiation. We sequenced coding regions from these candidate genes and found no polymorphisms in either ITK or CRSP-9.

Localization of a Family of Novel T cell Surface Proteins to the Tapr Region. Because the mouse homolog of rat Kim1 is located within the 0.4 cM region and is tightly linked with Tapr, we examined publicly available databases and found clusters of ESTs with some sequence similarity that provided only partial coverage and contained large segments of variation. The closest human homolog of Kim-1 is the human hepatitis A virus cellular receptor, hHAV-cr, and tBLAST searches of the human genome suggested that two additional homologs of Kim-1, perhaps members of a gene family, also are located on human chromosome 5 and mouse chromosome 11.

Using cDNA from conA-stimulated splenocytes, we identified and cloned two mouse orthologues of Kim1, which we term Tim1 and Tim2, that map to the Tapr region, as shown in FIG. 5A. TIM-3 is a third, more distantly related, orthologue of KIM-1.

All three members of this gene family are expressed by stimulated T cells, and all three forms map to the Tapr region of mouse chromosome 11/human chromosome 5 where they encode cell surface glycoproteins with common structural motifs, including an immunoglobulin (Ig) domain, mucin domain, and intracellular tail with phosphorylation sites. Because the cellular functions of these proteins is unknown, we refer to the genes as members of a T cell, Immunoglobulin domain, Mucin domain (Tim) gene family. Mouse Tim1 is the mouse homologue of rat Kim1 and the HAVcr-1 identified in African green monkeys and humans. Tim2 is a previously unknown gene that had not been identified in any organism prior to this study.

The mouse Tim1 gene encodes a 305 amino acid membrane protein, that has 78% overall identity with rat KIM-1 and 35% identity with human HAVcr-1. A gapped multiple sequence alignment with mouse TIM-1, rat KIM-1, human HAVcr-1 and African green monkey HAVcr-1, shown in FIG. 5B, demonstrates the degree of homology between the TIM-1/KIM-1/HAVcr-1 proteins in these species. The cytoplasmic region of TIM-1 contains two tyrosine residues and includes a highly conserved tyrosine kinase phosphorylation motif, (SEQ ID NO:59) RAEDNIY, which is integral to the predicted Itk and EGFR kinase site of TIM-1, (SEQ ID NO:601 SRAEDNIYIVEDRP. The mucin domain of TIM-1 has multiple sites for O-linked glycosylation, and there two sites for N-linked glycosylation found in the immunoglobulin domain.

TIM-2, a similar 305 amino acid membrane protein, has 64% identity to mouse TIM-1, 60% identity to rat KIM-1, and 32% identity to hHAVcr-1 (FIG. 5A, B). Like TIM-1, TIM-2 has two extracellular N-linked glycosylation sites and a serine, threonine-rich mucin domain with many O-linked glycosylation sites. TIM-2 also has an intracellular tyrosine kinase phosphorylation motif, RTRCEDQVY.

Tim3 encodes a 281 amino acid membrane protein that has a similar, integral membrane glycoprotein structure with multiple extracellular glycosylation sites and an intracellular tyrosine phosphorylation motif. Although the mucin domain is not as prominent in TIM-3 as it is in TIM-1 and TIM-2 (FIG. 5A), TIM-3 expressed on T cells likely interacts with a ligand on APCs and alters APC activation. TIM-3 does have four sites for N-linked and five sites for O-linked glycosylation, suggesting that TIM-3, like TIM-1 and TIM-2, is heavily glycosylated and might interact with a ligand present on other cells, such as antigen presenting cells.

Tim4 encodes a 344 amino acid protein in mice, and a 378 amino acid protein in humans. The predicted TIM-4 also shares the general membrane glycoprotein structural motifs of the other TIM proteins, a with an IgV-like domain with highly conserved cysteine residues, a threonine-rich mucin-like domain, and a short intracellular tail. However, TIM-4 lacks the phosphotyrosine motif present in the other TIM proteins, and therefore may modulate the funtion of the other TIM proteins.

Each of the TIM Ig domain shares an predicted integrin-binding motif that is similar to the SVVYGLR motif found in osteopontin, an transmembrane protein like the TIMs that is implicated in the regulation of cell adhesion, survival, and oncogenesis, as well as in the regulation of helper T cell differentiation. This integrin binding motif demonstrates alpha(9) and alpha(4) specificity.

Comparison of the sequences of the BALB/c and HBA/DBA coding regions for the three Tim genes revealed major polymorphisms in TIM-1, TIM-3, and TIM-4, but not TIM-2. In TIM-1, these polymorphisms encode three amino acid differences and a fifteen amino acid deletion in HBA/DBA. Seven predicted amino acid differences were identified in TIM-3 (FIG. 5*c*). Genomic sequences confirm that these polymorphisms, including the deletion, are true polymorphisms, not splicing variants. By further sequencing genomic segments of TIM-1 and TIM-3 in other mouse strains, we found that C57/BL6, a strain similar to DBA/2 with respect to its tendency to develop reduced $T_H2$ and AHR responses, also has the HBA/DBA allele of Tim1 and Tim3. The polymorphisms in TIM-1 and TIM-4 are located in the signal and mucin-like domains, while the polymorphisms identified in TIM-3 are clustered in the Ig domain (FIG. 5*c*). In glycoproteins with Ig and mucin domains, variants in either domain may affect receptor-ligand interactions, as shown for MAdCAM-1. Although the predicted cleavage sites of TIM-1 and TIM-4 are unaltered by the polymorphism in the signal sequence, it is possible that the polymorphism may affect the efficiency of cleavage and/or trafficking of the receptor to the cell surface. These Tim sequences and polymorphisms are important for immune responses, and for HAV viral pathogenesis in humans.

Analysis of genomic DNA samples from our N2 backcross (FIG. 3) demonstrated that the TIM-1 and TIM-3 polymorphisms cosegregate completely with Tapr. While these observations do not distinguish the extent to which changes in TIM-1, TIM-3, or both, are responsible for changes in AHR and $T_H2$-mediated inflammation, we suggest that polymorphisms in human TIM-1(hHAVcr-1) and/or TIM-3 underlie the strong association between asthma susceptibility and human chromosome 5q. This idea is supported by the fact that major variants in coding regions of human Tim1 are evident on examination of human genome and EST databases. Comparison of these human cDNA variants with the previously described variants of monkey HAVcr-1 and the mouse variants identified here demonstrates that there is extensive variation in the predicted protein sequences of TIM-1 (FIG. 5*b,c*). This high degree of variation distinguishes TIM-1 and its family members from many other candidate genes, such as the cytokines and the cytokine receptors that have been most closely studied as asthma susceptibility candidate genes. In addition, the association between Tim1 and asthma susceptibility is further supported by reports of significant linkage of mite-sensitive childhood asthma to D5S820 (mean LOD score=4.8), a marker which is approximately 0.5 megabases from Tim1 and Tim3 (FIG. 4.

In addition to the above genetic polymorphisms, there are several expression polymorphisms in the TIM genes that arise due to alternate splicing. Alternate splicing of TIM-1, TIM-2 and TIM-4 mRNA produces several TIM variants, some of which are secreted, soluble forms of the TIM receptors. These splice variants, along with TIM splice variants that have alternate 5' untranslated regions, may contribute to the cell-specific and condition-specific expression patterns of the TIM proteins.

T cells confer the Tapr effect. To better understand the function of the Tapr locus we determined whether allelic variation of Tapr affected the function of T cells or of antigen presenting cells (APC). For these experiments, we generated ovalbumin (OVA)-specific T cell receptor (TCR) transgenic mice (Tg) with the HBA background (HBA DO11.10), which we compared to TCR-Tg mice with the BALB/c background (BALB/c DO11.10). Purified CD4+ T cells from either of these strains were cocultured with OVA and dendritic cells (DCs) derived from either BALB/c or HBA bone marrow, and the cytokines produced were evaluated. Irradiated spleen cells were not used as APCs for this experiment, because it was found that irradiated spleen cells and other tissues express high levels of the TIM genes.

Figure 6:
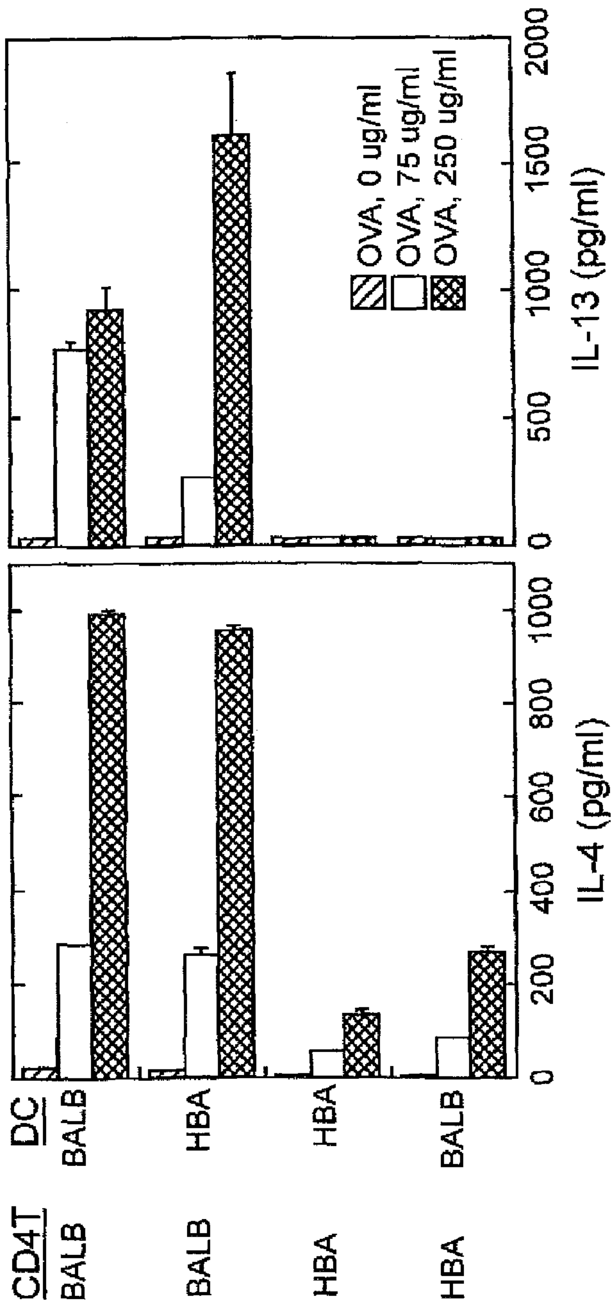
FIG. 6. Tapr Regulates CD4 T cell IL-4 and IL-13 Responses. T cells from BALB/c DO11.10 mice produce higher levels of IL-4 and IL-13 in response to antigen than do T cells from HBA DO11.10 mice. Splenic CD4+ cells were isolated by positive selection with anti-CD4 magnetic beads and then cocultured with bone marrow-derived DCs and OVA. After seven days, the cells were restimulated. Supernatants were harvested after 18-24 hours of the secondary culture. Data represent mean cytokine levels detected at increasing concentrations of OVA, ±S.D. Detection of expression of TIM-1 mRNA in purified CD 4 T cells during priming and differentiation.

BALB/c DO11.10 T cells produced higher levels of IL-4 and IL-13 than did HBA DO11.10 T cells, in a manner that was independent of the source of the antigen presenting cells (FIG. 6A). In addition, the source of the CD4 T cells determined the amount of IL-4/IL-13 produced at each antigen concentration, regardless of the source of the APC during either the primary or secondary stimulation. Equivalent levels of IL-12 were detected in culture supernatants for each combination of cell types, further demonstrating that BALB/c and HBA DC function were comparable. Furthermore, BALB DO11.10 and HBA DO11.10 T cells produced equivalent levels of IL-2 and demonstrated comparable levels of proliferation in response to OVA during the secondary cultures, indicating that HBA and BALB/c T cells are similarly activated, although the levels of Th2 cytokines they produce are quite distinct.

We show in FIG. 6B that within the first twelve hours of primary culture in our DO11.10/DC system, we find that mRNA for TIM-1 is expressed by both BALB/c and HBA CD4+ T cells. Within four days of primary stimulation, we find significant levels of IL-13 in supernatants of the BALB/c DO11.10 and detect none in the HBA DO11.10 supernatants. This differentiation is detectable in mRNA levels at 36 hours (FIG. 6B). Between twelve and thirty six hours, expression of IL-13 mRNA is reduced in HBA CD4 T cells, while IL-13 expression is maintained in the BALB/c CD4 T cells. Thus, during the primary response to antigen, BALB/c CD4 T cells develop a stronger Th2 response than do HBA CD4 T cells. Our findings demonstrate that Tapr regulates helper T cell differentiation during primary antigen specific responses, and we detect TIM-1 expression in CD4 T cells during the earliest stages of these responses.

Following differentiation into mature Th1 and Th2 subsets, helper T cells demonstrate committed TIM expression by RT-PCR, such that Th1 cells express TIM-3, while Th2 cells preferentially express TIM-1. All T cell populations demonstrate weak TIM-4 expression. While the Itk signal through TIM-1 is likely to promote Th2 differentiation, the EGFR signal through the TIM proteins is likely to enhance cell survival in effector and especially memory T cell populations. Since Itk is expressed only in T cell and mast cells, the Itk kinase activity on TIM-1 is restricted to immune cells, particularly those involved in asthma and allergy. However, other protein tyrosine kinases, such as EGFR, are involved in the function of TIM proteins expressed by other tissues, including ishemic epithelial cells, irradiated spleen cells, and tumor cells.

In these studies, we mapped Tapr, a locus that regulates the development of Th2 cytokine production and antigen-induced AHR, a cardinal feature of asthma. We localized Tapr using an interval specific congenic mouse (HBA) that carried a chromosomal segment homologous to human chromosome 5q, a region of the human genome that has been repeatedly linked to atopy and asthma. This region has also been repeatedly linked to 5q-syndrome associated with myelodysplasia and neoplastic cytogenic abnormalities, Using this congenic mouse strategy that converted a complex trait into a simpler, possibly single gene, trait, we narrowed the interval of Tapr to 0.4 cM interval, sequenced several candidate genes in this region, and positionally cloned the TIM gene family.

The TIM gene family has not been previously described. We identified and cloned the full cDNA sequence and discovered significant polymorphisms in the TIM-1 proteins of BALB/c compared to HBA mice. We found that the BALB/c sequences for TIM-1 and TIM-3 are associated with susceptibility to AHR and allergic T cell responses, whereas the HBA sequences are associated with protection against these responses. TIM-3 is preferentially expressed by differentiated $T_H1$. The association of polymorphic Tim3 variants with Tapr suggests that TIM-3 might regulate $T_H1$ and $T_H2$ cell function. However, the variations in Tim3 might also be attributed to a haplotype tightly linked to Tim4 or Tim1.

We believe that TIM-1 plays a very important role in the regulation of the immune system (particularly with respect to asthma and allergic disease) and in the regulation of epithelial and hematopoetic cell survival in response to stress (hypoxia, nutritional deficiency, irradiation, chemotherapy, etc.) for several reasons. First, Tim1, like Tim3, is expressed in CD4 T cells during primary antigen stimulation, when it is most likely that the Tapr effect occurs. T cells play a critical role in the development of AHR and in the pathogenesis of asthma, our results suggest that Tapr affects asthma by enhancing early CD4 commitment to Th2 responses by controlling the production of IL-13 and subsequent T cell differentiation. Second, HAV infection in humans during infancy or childhood is inversely associated with the development of asthma and allergy. We suggest that the HAV interaction with TIM-1/HAVcr-1 may alter the T cell cytokine production may able to reverse or prevent the biased Th1/Th2 balance in individuals otherwise prone to atopy and asthma. SLAM, a measles virus receptor, is an example of another T cell surface glycoprotein that regulates the Th1/Th2 balance in a manner that may be altered by viral interaction. Because some viral receptors, such as SLAM for the measles virus or CD4, CCR5, and CXCR4 for HIV, are receptors of the host's own immune system, even when an infection does not succeed, virus-receptor mediated signal transduction can lead to the release of cytokines and the development of disease.

Third, the polymorphisms in TIM-1 are associated with the different types of helper T cell responses that we observe. Therefore, the variants of TIM-1 may themselves contribute to the genetic Th1/Th2 predisposition that occurs in the absence of any known environmental cause of immune deviation. The HAV receptor in primates is known to be highly variable, and we propose that polymorphic alleles of human TIM-1/hHAVcr-1, like those we have identified in mice, may be associated with variations in Th2 bias and asthma susceptibility. Mutations in the genes for cell surface molecules that serve as viral receptors and that alter susceptibility to infection are not uncommon, and therefore significant genetic variation in TIM-1 and other members of the TIM gene family is far more likely to be observed than variation in other genes such as those for cytokines. It is unclear why asthma susceptibility alleles might be prevalent in the human gene pool, but the association of Tapr with HAVcr provides an interesting explanation for the persistence of asthma susceptibility alleles. During human evolution certain alleles of the Tim gene family may have conferred resistance to atopic diseases and other immune disorders, but selection of those resistance alleles may have been counterbalanced by selection of alternate alleles that confer resistance to viral pathogenesis.

In summary, our studies represent the first successful utilization of a congenic mouse strategy to locate a strong candidate asthma susceptibility gene and overcome the inherent difficulties in the examination of this complex genetic trait. We identified a previously unknown gene family that exists in a region homologous to human chromosome 5q, and which plays a major role in Th cell development and in asthma susceptibility. While prior studies in humans identified several candidate genes on human chromosome 5q, the Tim1 gene product identified in our study also provides an explanation for the inverse relationship between HAV infection and reduced asthma susceptibility.

Subpopulations of $CD4^+$ T cells (Th) produce distinct patterns of cytokines, and this has led to the concept of functional heterogeneity among Th cells. Type 1 Th cells (Th1) produce interleukin 2 (IL-2) and/or interferon γ, elicit delayed type hypersensitivity (DTH) responses and activate macrophages. Type 2 Th cells (Th2), on the other hand, produce IL-4, IL-5 and IL-10 and are especially important for IgE production and eosinophilic inflammation, and may suppress cell mediated immunity. Th2 cells are believed to play a pivotal role in the pathogenesis of atopy. Several factors determine whether a T helper cell will differentiate into Th1 versus Th2 during a particular immune response. These include, but are not necessarily restricted to, the cytokine milieu, the strength of the TCR signal and/or antigen density, and the costimulatory pathways. CD4+ T helper cell differentiation into Th1 or Th2 subsets has profound effects on the outcome of atopy, autoimmune diseases, infectious diseases, and graft rejection.

The specific features of immune responses that protect nonatopic individuals from the development of allergic diseases and which could inhibit allergic responses in atopic individuals are poorly understood. Because Th1 cells cross regulate Th2 cells in some systems, allergen-specific Th1 cells have been assumed to regulate allergic disease and asthma. Th1 cells inhibit the development and proliferation of Th2 cells, and IgE production is reciprocally regulated by IL-4 and IFN-γ. This suggests that protection from allergy is due to the development of inhibitory allergen-specific Th1 cells. Allergen-specific T cell clones derived from the peripheral blood of nonallergic individuals have been shown to produce Th1 cytokines. These observations have also supported the hygiene hypothesis of asthma, which suggests that the prevalence of infections, particularly those that induce Th1 responses, are reduced in westernized societies by improved public health measures and the use of vaccines and antibiotics. As a result, Th2 responses and atopy develop more intensely and rapidly in the absence of Th1 mediated responses.

The TIM genes identified herein are also candidate oncogenes. Transfection of cell lines with TIM genes confers resistance to cell death, and the predicted EGFR kinase motif described in TIM-1 provides a probable mechanism by which this cell survival is controlled. Furthermore, TIM-1 demonstrates a significant degree of sequence identity (approximately 20%) and structural similarity (a transmembrane glycoprotein with an IgV domain, mucin/syndecan domain, transmembrane domain, and intracellular domain with similar phosphotyrosine motifs) with TOSO, a protein that protects cells from Fas-mediated apoptosis. Like the TIM genes, TOSO is a likely oncogene, which maps to a region of the genome with frequent changes in hematologic malignancies and solid tumors.

Methods

Animals.

Congenic lines, including C.D2 Es-HBA were generated by introgressively backcrossing DBA/2N onto a BALB/cAnPt background. BALB/cBy, DBA/2J, and (BALB/c×DBA/2) F1 mice (CByD2F1/J) were obtained from the Jackson Laboratory (Bar Harbor, Me.), while BALB/cAn and DBA/2N were obtained from Taconic Labs. (BALB/c×HBA) F1 mice were produced with a cross between BALB/cByJ and HBA. N2 mice were generated by backcrossing (BALB/c×HBA) F1 to HBA. In our analysis of recombinant N2 animals, recombinant mice were tested along with non-recombinant siblings, whenever possible. In order to examine individual N2 genotypes in multiple assays, we preserved selected recombinant haplotypes by backcrossing selected N2 mice to HBA to generate N3 mice, which were genotyped to chose mice carrying the recombinant N2 haplotype. DO11.10 mice, which are transgenic for TCR recognizing OVA peptide 323-339 ($pOVA^{323-339}$) and backcrossed to BALB/c(43), were kindly provided by Dr. Dennis Loh and were bred in our facilities. HBA DO11.10 mice were produced by backcrossing DO11.10 to HBA. DO11.10 mice were selected by FACS analysis for the TCR-Tg and genotyped to select for HBA alleles between D11Mit135 and D11Mit168. The Stanford University Committee on Animal Welfare approved all animal protocols.

Genotypinq.

Additional markers around the Tapr locus were identified by testing all available "D11Mit-" markers present between D11Mit140 and D11Mit269 and all radiation hybrid markers near D11Mit271 and D11Mit22 for any polymorphisms between DBA/2 and BALB/c. MIT MapPair primers were obtained from Research Genetics (Huntsville, Ala.), and all other primers were synthesized in the Protein and Nucleic Acid Facility (Stanford, Calif.). PCR was performed as previously described, and SSLP polymorphisms were resolved with 4-5% Metaphor agarose (BioWhittaker, Walkersville, Md.). Products analyzed for SSCP were amplified with $^{33}P$-dCTP and separated on denaturing acrylamide gels at 40 W and $4^2C$, with a Sequi-Gen GT System (Bio-Rad, Hercules, Calif.).

Immunization Protocols.

Mice studied in cytokine production assays were primed with KLH (Calbiochem, La Jolla, Calif.) in complete Freund's adjuvant (CFA) (DeKruyff et al. *J Immunol* 149, 3468-76 (1992)). For measurement of airway hyperreactivity, mice were immunized with OVA intraperitoneally (i.p., 50 μg) complexed with aluminum potassium sulfate (alum) on day 0, and intranasally (i.n. 50 μg OVA in 50 μA of PBS) after light anesthesia on days 7, 8 and 9. Control mice received i.p. injections of alum alone and intranasal PBS. Airway hyperreactivity to inhaled methacholine was measured 24 hours after the last intranasal dose of OVA (day 10).

Measurement of Airway Responsiveness.

Airway responses were assessed by methacholine-induced airflow obstruction from conscious mice placed in a whole body plethysmograph (Buxco Electronics Inc., Troy, N.Y.), as described previously (Hansen et al. *J Clin Invest* 103, 175-83 (1999)).

Cell Culture.

Lymph node cells from mice primed with KLH were prepared as described previously (Yeung et al. *J Immunol* 161, 4146-52 (1998)). Transgenic DO11.10 CD4 T cells were positively selected using MACS columns following incubation with anti-CD4 magnetic beads (Miltenyi Biotech, Germany). $2\times10^4$ cells/well were cocultured in 96-well round bottom plates with 250 μg/ml OVA and $1\times10^4$ bone marrow-derived dendritic cells/well. After seven days, the DO11.10 T cells were washed and restimulated with fresh antigen presenting cells and antigen at the concentration indicated. Antigen concentration for the primary DO11.10 cultures was titrated during the restimulation. Bone marrow-derived dendritic cells were generated as previously described with some modifications; $5\times10^6$ bone marrow cells were cultured in 9-cm diameter tissue culture dishes with 10 ml culture medium containing 20-25 U/ml GM-CSF. Loosely adherent cells were transferred onto a second dish on the sixth day of culture; within four days, these transferred cells were used as a source of dendritic cells.

Cytokine ELLISA.

ELISAs were performed as previously described in Macaulay et al. J Immunol 160, 1694-700 (1998); and Macaulay et al. J Immunol 158, 4171-9 (1997).

Monoclonal Antibodies.

Monoclonal antibodies for ELISA and FACS analysis were purified from ascites fluid by ammonium sulfate precipitation and ion-exchange chromatography. Anti-clonotypic antibody KJ1-26.1, was generously provided by Dr. Philippa Marrack, National Jewish Medical Center, and the antibody was FITC-conjugated according to standard protocols prior to FACS.

Example 2

Identification of Human Tim Sequences

The positional cloning of the TIM gene family within a locus that confers protection against the development of Th2 responses and allergen-induced airway hyperreactivity provides an opportunity to greatly improve our understanding of the regulation of Th2 driven responses and atopic diseases. In addition, TIM-3 is specifically expressed on murine Th1 cells and anti-TIM-3 mAb leads to increased severity of experimental autoimmune encephalomyelitis (EAE). This emphasizes the importance of the gene family in T helper subset regulation.

Figure 7:
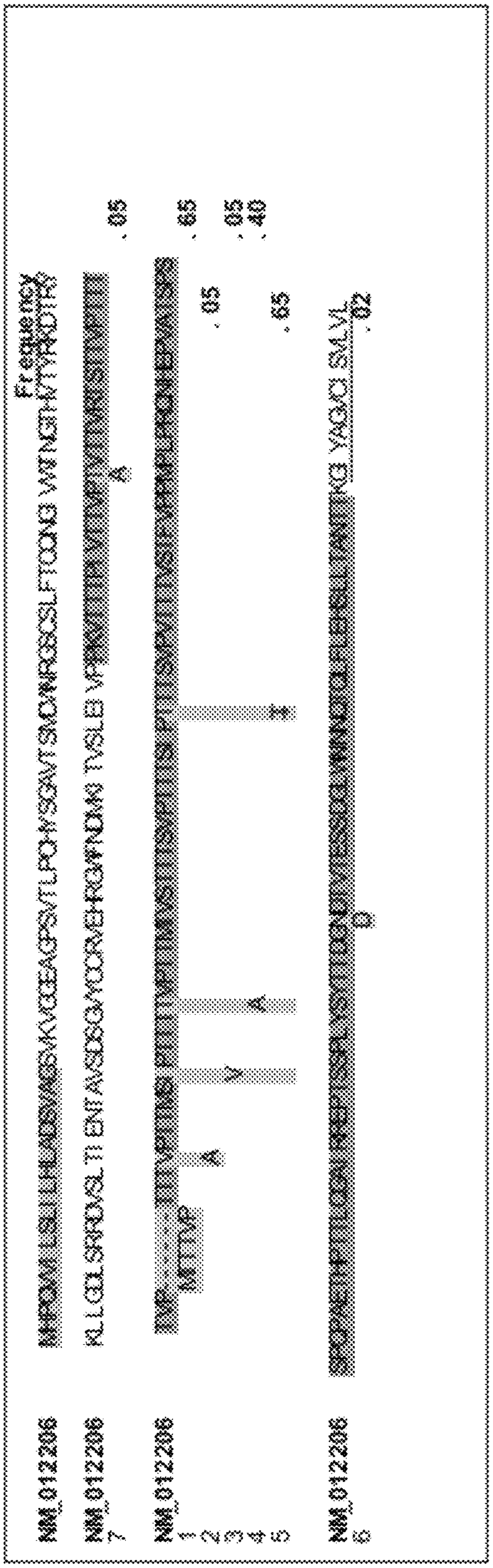
FIG. 7. Polymorphisms in human TIM-1, NM 012206 (SEQ ID NO:17).

The human Tim cDNAs, which are the orthologues of murine Tim-3 and Tim-4 were cloned by PCR. The human orthologue of TIM-1 was cloned as HAVcr-1, the cellular receptor for hepatitis A virus. The TIM family genes are immediately adjacent to each other on human chromosome 5, in the order TIM-4, TIM-1, TIM-3, with no intervening genes. There are TIM pseudogenes on chromosomes 12 and 19. The gene family members are only moderately related. The protein sequences and relationship among the Tim gene family are shown in FIG. 7.

The cytoplasmic domains of TIM gene family members are the most conserved domain between mouse and human orthologues, e.g., 77% identity between the human and mouse TIM-3 cytoplasmic domains. In contrast, the whole TIM-3 is only 63% identical between human and mouse. Each TIM gene contains a distinct predicted tyrosine signaling motif. The cytoplasmic region of TIM-1 contains two tyrosine residues and includes a highly conserved tyrosine kinase phosphorylation motif, (SEQ ID NO:59) RAEDNIY. The expanded region, (SEQ ID NO:60) SRAEDNIYIVEDRP, contains a predicted site for Itk and EGF receptor phosphorylation. Itk is known to phosphorylate phospholipase C-γ (PLC-γ), and thereby trigger a cascade of signaling events that are involved in T cell activation and helper T cell differentiation. Furthermore, Itk signaling affects Th1/Th2 differentiation, and $Itk^{-/-}$ mice do not develop strong Th2 responses. EGF receptor kinase activity is associated with cell survival and resistance to cell death. Similarly, TIM-3 contains distinct, conserved tyrosine phosphorylation and SH2 binding motifs in the cytoplasmic domain. This suggests that the interaction of a TIM with its ligand will engage an intracellular signaling pathway and that each TIM will be distinct in this signaling.

The extracellular IgV domain of the TIM proteins also contains a predicted integrin-binding motif that is similar to the SVVYGLR motif of osteopontin that is involved in adhesion via alpha(9)beta(1), alpha(4)beta(1), and alpha(4)beta (7) integrins. TIM-1 transfected pre-B cells of the 300.19 line demonstrate a high degree of adhesion an increased survival in cell culture, as compared to non-transfected 300.19 cells. TIM-1 and TIM-2 transfected CHO cells also demonstrate enhanced survival compared to untransfected CHO cells. These results demonstrate that the TIM proteins regulate cell adhesion and death Genetic Polymorphisms in the Human Tim1 and Tim3 Genes.

SNPs or nucleotide polymorphisms and deletions/insertions present in the human Tim1 gene are identified. Because SNPs are extremely common in the genome, occurring every 300-600 base pairs, only the coding region of Tim1 was analyzed. Moreover, genetic variations that are common are also likely to be important. Initially cDNA is sequenced from T cells taken from 30-40 individuals (60-80 chromosomes). Power calculations show that surveying target sequences in coding regions of 60 chromosomes will easily detect SNPs with a population frequency of greater than 1%, and having a more than 90% chance of detecting alleles with a population frequency of 5% or greater. Therefore, screening 30-40 individuals for sequence variations captures most of the common, functionally relevant, non-conservative, DNA variation present in a population.

Since DNA variants/SNPs in close physical proximity often show strong dependency relationships (i.e., linkage disequilibrium), it is determined if a group of DNA variants (SNP haplotypes) are inherited together, and determined if screening for only a portion of these SNPs will be sufficient for identifying the haplotype. Analysis of large regions of various chromosomes indicate that discrete haplotype blocks (of tens to hundreds of kilobases) are generally present, each with limited diversity punctuated by apparent sites of recombination. To find haplotypes, cDNA is sequenced and searched for combinations of sequence variations that are seen repeatedly in multiple individuals. Peripheral blood mononuclear cells (PBMC) were from 38 donors, and were stimulated in vitro with PHA (7.5 μg/ml) for 24 and 72 hours, or with Concavalin A (2 μg/ml) for 24 hours. PMA (20 ng/ml) and lonomycin (1 μM) were added during the last six hours of stimulation. The cells were then harvested and the total RNA was extracted using Trizol reagent (Invitrogen). To obtain cDNA templates for sequencing, RNA was reverse transcribed using Superscript II reverse transcriptase (Invitrogen), according to the manufacturer's protocol. The cDNA were used to PCR amplify the full length of Tim cDNA using Herculase Hot Start™ high fidelity polymerase (Stratagene). The PCR primers were: (SEQ ID NO:41) GTGTCTGACAGTGGCGTA (forward), (SEQ ID NO:42) TTTGCCCAGGCAGAACCA (forward), (SEQ ID NO:43) CCACCCAAGGTCACGACT (reverse), (SEQ ID NO:44) ATGCCACGGACTAAGACC (reverse). The PCR products were purified with. Qiagen QIAquick gel extraction reagents, and sequenced using four internal sequencing primers for Tim1 and two internal sequencing primers for Tim3.

The full length Tim1 RT-PCR product was cloned in these individuals by taking total RNA from activated T cells and transcribing it with Superscript II and oligo dT. Tim1 cDNA was amplified with Expand high fidelity polymerase (Roche) to generate a 1 kb product spanning the Tim1 coding region, which was purified with a PCR Purification kit (Invitrogen). This purified product was then cloned into the TOPO pEF6 vector (Invitrogen), followed by transformation of TOP10 competent bacteria. Bacterial colonies were grown on LB plates with ampicillin selection. Single colonies were picked and plasmid preps generated using Qiagen mini prep kits. Restriction mapping using Hind III digestion was used to select plasmids containing inserts in the correct orientation. These plasmids were then sequenced with three different primers, forward (T7), internal and reverse (BGH), and the sequences aligned in SeqMan program with NCBI human TIM reference sequence.

After sequencing Tim1 from the chromosomes from 35 individuals (70 chromosomes) several polymorphisms in Tim1 were identified, which are shown in FIG. 8. These polymorphisms are numbered 1-7 (left column). The full sequence of human TIM-1, which is listed in the NCBI database (NM_012206), is provided in FIG. 8 as a reference point. This sequence is present in less than 20% of the chromosomes that were sequenced, due to the existence of multiple, prevalent sequence polymorphisms in the coding region. 6 additional sequence variations were identified, shown in FIG. 8, and all of the polymorphisms were observed in the mucin, extracellular domain, as was true for mice, although the specific variations were distinct from those seen in mice. Importantly, there is a limited degree of association between these variants, in various combinations. The most pronounced variations are the insertion labeled polymorphism 1, 157insMTTTVP (SEQ ID NO:57), which was observed in 65% of the chromosomes, and the deletion in polymorphism 5, 187ΔThr, was observed in 65% of the chromosomes. Polymorphism 4 was observed in 40% of the chromosomes, and the other polymorphisms were each observed in ≤5% of the chromosomes. Notably, most of these variations (2-6) are located within exon 3, the first mucin-encoding exon, and all of the variants occur at the genomic level and are not splice variants.

Based on this sequence analysis of mRNA, a more rapid method for analyzing the genomic DNA from the larger number of patients/controls has been developed. To screen individuals for the variations seen in sequences shown in FIG. 8, the DNA is initially tested for simple sequence length polymorphisms (SSLP) in a 150 PCR product, which can detect the major insertion, polymorphism 1, and the deletion, polymorphism 5.

Figure 9:
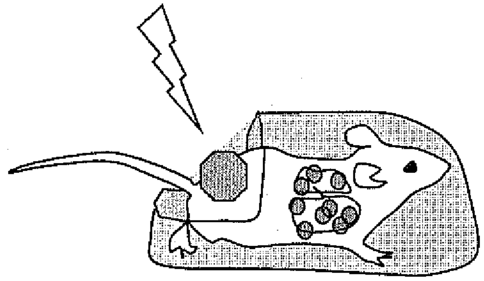
FIG. 9. A schematic for assessing the effect of combining radiation and immune therapies.

In addition, to genotype the other polymorphisms (2-4, 6, and 7) and identify novel polymorphisms, a relatively simple assay using single strand conformational polymorphism (SSCP) analysis of PCR products has been developed. Under well-optimized conditions, SSCP analysis detects more than 90% of single nucleotide substitutions and all length polymorphisms. For this analysis, PCR primers have been identified that amplify each exon of the Tim genes, and variants can be distinguished using standard non-denaturing SSCP gel electrophoresis methods (FIG. 9). Non-denaturing polyacrylamide gel electrophoresis is used with an ABI 377 DNA sequence for high resolution SSCP analysis of each exon. Fluorescent end-labeled primers are synthesized and purified. Novel SSCP patterns that are detected during the high-throughput genotyping process will identify novel variants. Using this method, the genotype of patients and controls is rapidly analyzed.

The Tim3 gene was analyzed using essentially the same methodologies. mRNA from activated T cells is sequenced to identify Tim3 polymorphisms, as well as long range haplotypes between the Tim1 and Tim3. After sequencing Tim3 cDNA representing 60 chromosomes, it has been found that Tim3 is polymorphic, as it is in the mouse genome. However, only one polymorphism, Leu140Arg, is prevalent, found in approximately 12% of the chromosomes represented.

Example 3

Expression of Tim Sequences

Murine TIM-3 protein is expressed on Th1 clones but not on naive T cells or Th2 cells. Using TCR transgenic T cells, TIM-3 protein was not expressed on Th1 cells after one or two rounds of Th1-directed differentiation but was expressed after the third and further rounds of Th1 stimulation. TIM-3 mRNA expression was detected somewhat earlier. In order to determine if TIM-3 gene expression was the same in human, TIM-3 and TIM-1 mRNA expression in human Th1 cells was examined using tetanus toxoid specific T cells generated by stimulation with antigen in the presence of IL-12 and anti IL-4 mAb. Given the association of TIM-1 with asthma, TIM-1 and TIM-3 mRNA expression in human Th2 cells was examined. Th2 cell lines were generated from allergic donors by in vitro stimulation with allergen, IL-4, and anti IL-12 mAb. RNA was analyzed by PCR for TIM gene expression.

TIM-3 was generally expressed after Th1 differentiation whereas TIM-1 was lost. Conversely, TIM-3 was not expressed in any of the Th2 but TIM-1 was expressed in all Th2 cells. Both TIM-1 and TIM-3 are expressed in monocyte-depleted, unstimulated peripheral blood mononuclear cells from the donors used to derive the Th1 and Th2 cell lines, presumably because this mixed population contains both Th1 and Th2 memory cells. These results suggest a reciprocal relationship with TIM-1 being expressed in Th2 and TIM-3 in Th1. This reciprocal relationship between TIM-1 and TIM-3 has also been observed in the mouse.

In human tissues, a 4.4 kb TIM-1 mRNA was very strongly expressed in kidney and testis. The 4.4-kb mRNA was present in almost all tissues, though it was faint in most. A 5.5-kb band was observed in colon and liver. A 7.5-kb band was observed in spleen, thymus, and peripheral blood leukocytes, and smaller than 4.4-kb bands were observed in some organs.

These results suggest that hTIM-1 is expressed at some level in most human tissues and that a message of 7.5-kb may code for hTIM-1 in tissues of immunological interest. However, expression of Kim-1 (Kidney Injury Molecule-1), the rat homologue of TIM-1, increases in kidney upon ischemic injury. Since the MTN blots used in the expression analysis were prepared from mRNA extracted from cadavers, the increased expression of TIM-1 in kidney was re-analyzed. TIM-1 was not found to be overexpressed in kidney RNA obtained from normal kidney biopsies. Therefore, it is likely that the high levels of expression of TIM-1 observed in kidney and testis were due to an up-regulation in the expression of TIM-1 resulting from tissue injury. The injured kidney may express proteins that direct incoming inflammatory cells towards a more protective Th2 response rather than a destructive Th1 response.

Example 4

TIM Ligands and Antibodies

Generation of Antibodies. Generation of monoclonal antibodies against mouse TIM-1 allows examination of the cell surface expression of TIM-1 in different tissues, cell lines and mouse strains. Both alleles of mouse TIM-1 have been cloned into a vector for high protein expression (Invitrogen, pEF6-TOPO). Rats have been immunized and boosted with both Tim1 cDNA constructs to rapidly generate antibodies against cell surface molecules. This method with cDNA vaccination favors the production of mAb against cell surface epitopes since the Tim1 cDNA will be taken up by APC, which will express the TIM-1 as a cell surface molecule. In order to generate mAb that would bind equally well to both the BALB/c and the HBA TIM-1 (by binding to conserved domains of TIM-1 such as the Immunoglobulin domain of TIM-1), both the BALB/c and HBA Tim1 cDNA (pEF6-mTIMbalb and pEF6-mTIMhba) were injected into each rat.

Further boosting of the Tim1 cDNA-immunized rats was done with CHO cells stably transfected with the pEF6-mTIM-1-GFP expression constructs. CHO transfectants expressing high levels of mouse TIM-1 were sorted by FACS, and injected into the rats. Another mTIM-1 expressing cell was generated by stably transfecting the pre-B cell line 300.19 with the pEF6-mTIM-1 expression constructs. This line is used to screen the rat serum and the hybridomas following fusion for anti-TIM-1 antibody by flow cytometry. Rats have been generated which have high polyclonal titers against anti-TIM-1, as detected by the binding of rat serum (and a secondary FITC-goat anti-rat Ig) to stable pEF6-mTIM1-transfected 300.19 cells, as compared with control serum from unimmunized rats. This staining is specific for TIM-1 since there is no reactivity with nontransfected cells or cells transfected with TIM-2.

The rat spleen is removed and the splenocytes fused with a myeloma cell line (SP/2) to produce hybridomas. Hybridoma supernatants are screened using the TIM-1 transfected 300.19 cell lines to identify hybridoma clones that produce monoclonal anti-TIM-1. Specificity of the mAb for TIM-1 (and not other TIM proteins) is confirmed using TIM-2 transfected cells and mTIM-3 transfected cells or TIM-31 g fusion protein.

Antibody Staining. Th1 and Th2 cell lines were generated from both BALB/c and HBA DO11.10 spleen cells. RT-PCR for TIM-1 mRNA expression demonstrated that TIM-1 is expressed in Th2 lines, but not in Th1 lines, following two rounds of restimulation with antigen under standard polarizing conditions. DO11.10 T cells following two rounds of stimulation with antigen/APC under Th2 polarizing conditions were stained with the polyclonal rat anti-TIM-1 antiserum. These Th2 cells expressed high levels of TIM-1.

These experiments showing preferential expression of TIM-1 in Th2 lines are quantified and confirmed using anti-Tim-1 mAbs and Northern blots. DO11.10 cells from BALB and HBA are cultured with antigen and APC, and restimulated for 1, 2, and 3 weeks under standard polarizing conditions (anti-IL-12 plus IL-4 or anti-IL-4 plus IL-12). After each week of stimulation, cells are stained with anti-TIM-1 mAb. By harvesting stimulated cells at various time points the kinetics of TIM-1 expression on T cells undergoing differentiation to Th1 or Th2 subset is determined. To determine if Tim-1 surface expression changes following T cell activation, we will also compare TIM-1 expression on resting and activated T cells one week after each round of antigen stimulation, by stimulating some cells with PMA and ionomycin. Activated cells are stained for intracellular cytokine expression to verify the Th subset differentiation of the T cells. Alternatively, quantitative RT-PCR or northern blots using mRNA harvested from T cells activated with PMA plus ionomycin, following each round of stimulation, are used to determine relative levels of mRNA production.

TIM-1-Ig fusion proteins BALB/c TIM-1-mIgG2a has been prepared, which is a fusion protein between the TIM-1 polypeptide and the Fc region of mouse immunoglobulin. The vector has been engineered to contain a mutation in murine IgG2a Fc that minimizes binding to Fc receptors. The TIM-1 fusion protein is utilized in characterization of TIM-1 function. The TIM-1 Ig fusion protein is expected to block TIM-1 function by binding to the TIM-1 ligand and interrupt TIM-1/TIM-1-ligand interactions.

Purified D1muc-Fc fusion protein containing the cys-rich immunoglobulin domain and ⅔ of the mucin-like region of TIM-1 fused to the hinge and Fc fragment of human IgG1 (IgVmuc-hIg) was run on a gel. This protein was expressed in CHO cells, and the IgVmuc-hIg protein was purified from CHO supernatants with protein-A agarose columns. Purified IgVmuc-hIg fusion protein neutralizes about 2 logs of HAV infectivity. In addition, treatment of HAV with IgVmuc-hIg produced a major shift in the sedimentation of the HAV particles, indicating that IgVmuc-hIg induced uncoating of the viral genome, whereas a fusion protein containing only the Ig-like region without the mucin domain (IgV-hIg) did not. This HAV neutralization system and the IgVmuc-hIg fusion protein will be used to analyze the function of TIM-1/HAV receptor alleles.

Based upon the in vivo effect of anti-TIM-3 mAb on macrophage expansion and activation, it was hypothesized that the TIM-3 ligand would be expressed on cells of the myeloid lineage. Dendritic cells (DC) were prepared from blood monocytes according to established protocols with 1000 U/ml IL-4 and 800 U/ml GM-CSF. DC were matured by replating the cells for 2 days in IL-4 (1000 U/ml) and GM-CSF (800 U/ml) supplemented with IL-1$\beta$ (10 ng/ml), TNF-$\alpha$ (10 ng/ml), IL-6 (1000 U/ml), and $PGE_2$ (1 $\mu$g/ml). Mature DCs stained positively with hTIM-3-Ig, though there was variability among donors, suggesting that mature DC express a ligand for the IgV domain of TIM-3. Bone marrow derived endothelial cells stained very weakly and B cell lines did not stain with TIM-3-Ig.

Although the intracytoplasmic tail of Tim1/huhavcr-1 is relatively short, it contains a sequence that is highly conserved between mouse, rat, human and monkey (SEQ ID NO:59, RAEDNIYI), and which may be phosphorylated, and signal through interaction with other signal transduction molecules. The most likely candidate molecule that can bind the RAEDNIYI motif in T cells is the tyrosine kinase Itk. The interleukin-2 inducible tyrosine kinase, Itk is a nonreceptor protein tyrosine kinase of the Tec family that participates in the intracellular signaling events leading to T cell activation. Tec family members contain the conserved SH3, SH2, and catalytic domains common to many kinase families, but they are distinguished by unique sequences outside of this region. It is known that Itk phosphorylate phospholipase C-γ (PLC-γ), and triggers a cascade of signaling events that are involved in T cell activation and helper T cell differentiation. In the absence of Itk signaling, Th2 cells do not develop. These results suggest that TIM-1/huhavcr-1 may signal through Itk, thereby altering the cytokine development in CD4 T cells.

Example 5

Combination of TIM Activation with Cytotherapy

The induction of liver cell death in a mouse model of hepatitis or airway cell death in a model of airway reactivity promotes TIM-1 mediated costimulation by PS (Lee et al. (2010) J. Immunol. 185(9):5225-35). As co-ligands for phosphatidylserine (PS), TIM-3 and TIM-4 (which is a counter ligand for TIM-1) further modulate immune responses in these settings via PS-binding. TIM-directed therapies can modify responses to cytotoxic treatments, including chemotherapy or radiation (such as radiation-induced pneumonitis, hepatitis, and other radiation-specific effects) and modify anti-tumor immune responses, especially after radiation. The identity of PS as a ligand for the TIM family members creates opportunities for imaging TIM-binding capacity in vivo and adapting therapies accordingly.

As described in Example 4, antibodies have been produced against mouse TIM-1. Additionally antibodies have been produced that specifically bind to human TIM-1 (Umetsu et al (2005) Nature Immunology 6, 447-454), providing a library of well characterized monoclonal antibodies against human and mouse TIM-1. The agonistic monoclonal 3B3 antibody blocks TIM-1:PS binding and costimulates T and NKT cells as an immune therapy. When used as tumor immunotherapy (IT) and when combined with radiation (RT) to the primary tumor site, this antibody enhances local breast cancer tumor control and reduces the size and number of distant breast cancer metastases in a mouse model of breast cancer. The combination therapy may improve outcomes for patients who receive radiation for metastatic or locally advanced breast cancer by inducing immune responses against their tumors.

Because TIM-1 is activated by binding to phosphatidylserine, a phospholipid that is exposed in irradiated tumor tissues, IT with TIM-1 may demonstrate greater specificity (and fewer ‘off target’ autoimmune side effects) than other IT agents currently under development, and the functional interaction between TIM-1 and PS in the tumor immune microenvironment provides a unique method for focusing immune activation to the irradiated tumor.

The use of imaging tracers coupled to PS-binding molecules, such as annexin V or TIM-containing peptides or mimics, can be used to monitor and optimize the delivery of immunotherapies that target the PS-binding TIM family members.

Example 5

Tumor Model Studies

Our studies identified specific, well defined changes in the subpopulations of cells present after radiation therapy (RT) and the costimulatory receptors expressed those cells. We find that RT selectively induces the expression of certain receptors, such as the TIMs, CD40, 4-1 BB, PD-1, and PD-L1. This enhancement persisted for at least one week, which includes the 24-72 hour timeframe that is critical for initiation of anti-tumor immune responses after RT. Our results indicated that these targets (PD1/PD-L1 and TIM-1) could be more effective in combination with RT than targets such as CTLA-4 that are not as significantly upregulated after RT. The relative radioresistance of regulatory T cell (Treg), myeloid suppressor cell (MSC), and antigen presenting cell (APC) subsets, also made them attractive targets for immunotherapy after RT. Thus, studies were performed with the experimental design shown in FIG. 9.

Figure 10:
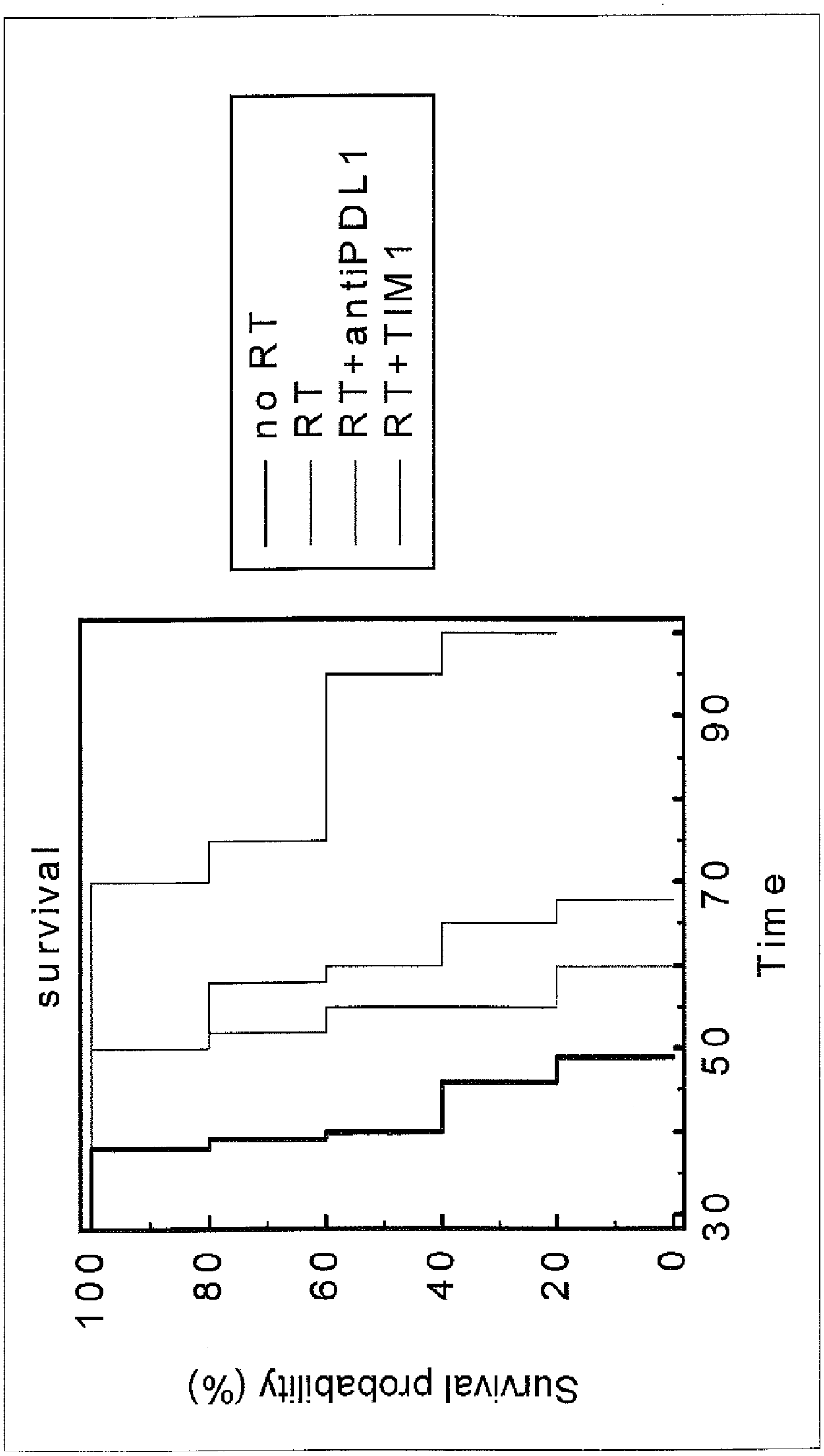
FIG. 10. Graph of survival probability.
Figure 11:
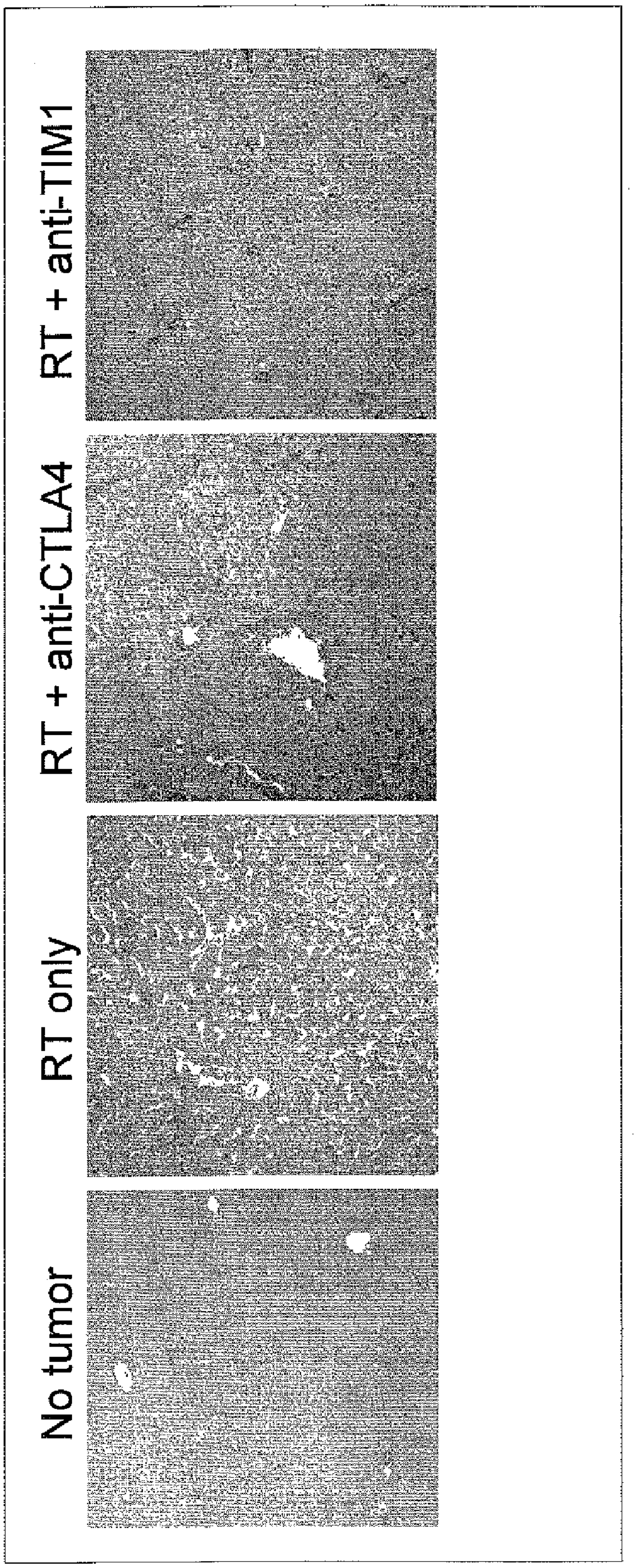
FIG. 11. Day 55 liver histology demonstrates that the agonistic anti-TIM1 antibody 3B3 depletes distant metastatic 4T1 breast cancer cells and associated immunosuppressive MSC inflammation better than anti-CTLA4.
Figure 12:
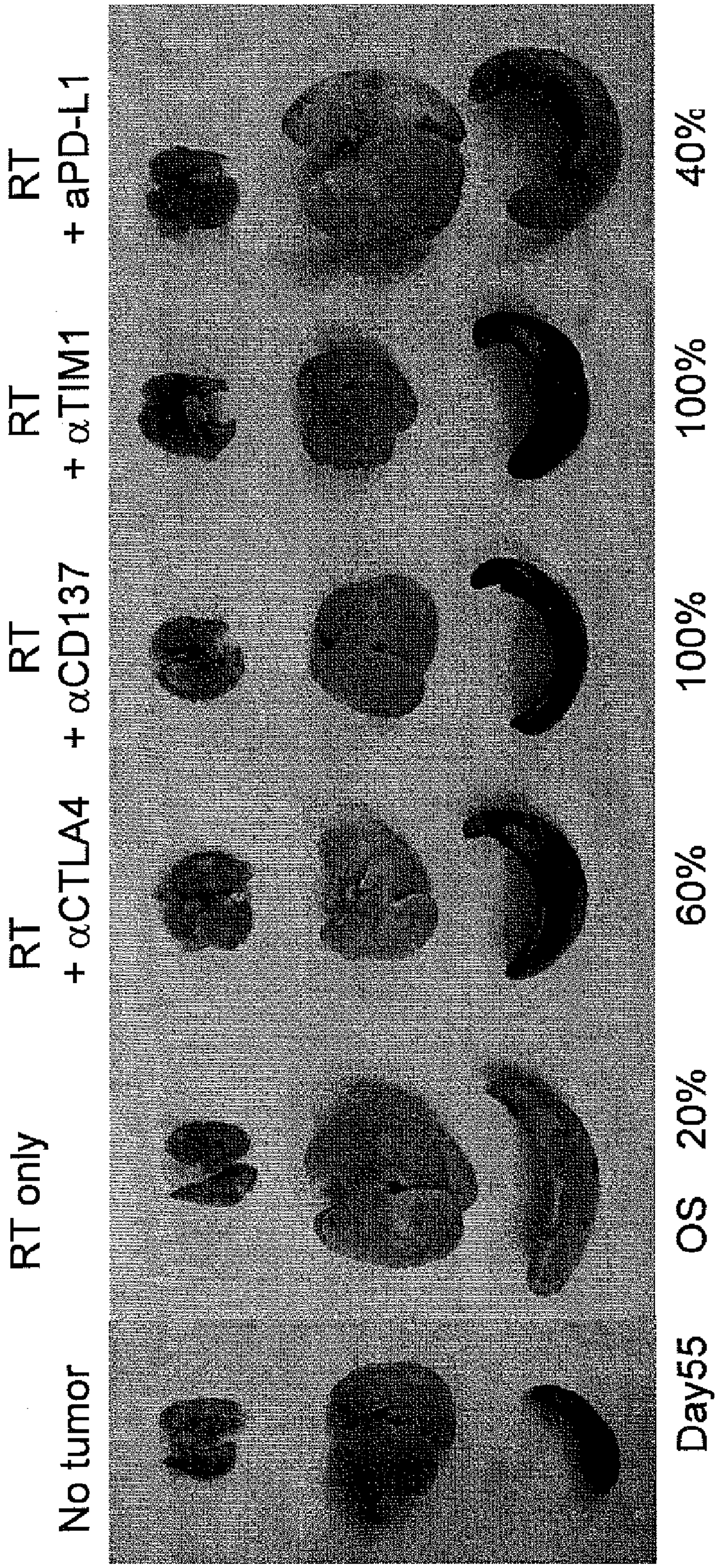
FIG. 12. Side effect of radiation therapy in the absence and presence of immunotherapy.

The most efficacious regimens identified in these studies targeted TIM-1. In mice with established, metastatic breast cancer, administration of an activating anti-TIM1 antibody at the time of primary tumor irradiation resulted in decreased metastatic disease burden and increased overall survival, compared to mice treated with RT alone, while the antibody alone had no effect, shown in FIG. 10. Specifically, administration of an activating anti-TIM1 (α-TIM1, 3B3) antibody at the time of primary tumor RT leads to: 1) decreased metastatic disease burden (shown in FIG. 11 with day 55 liver histology; and in FIGS. 12) and 2) increased overall. This RT+IT combination produces a robust anti-breast cancer vaccination effect, leading to eradication of metastases outside of the radiation field. Importantly, this benefit was observed without systemic or local (in the irradiated field) tissue toxicities. Inhibition of PD-L1 and depletion of MSCs did not demonstrate a therapeutic effect in this model.

These data show that RT has substantial effects on immune cells that are critical for IT, and identify TIM1 as an especially effective IT to combine with RT. These changes provide a window for the systematic manipulation of anti-breast cancer immune responses. TIM-1 is an especially attractive IT target for use with RT for the treatment of metastatic or locally advanced, unresectable breast cancers.

Example 6

Effects of Irradiation and Hematopoetic Stem Cell Transplantation on Airway Hyperreactivity Airway hyperreactivity (AHR) is a complex trait, influenced by multiple genetic and environmental factors, which are the subject of active basic and clinical research. Diffuse pulmonary toxicity is a serious complication of myeloablative hematopoetic stem cell transplantation (HCT) regimens, but our understanding of the etiology of this is very limited. Few case reports document transfer of atopic disorders after allogeneic HCT, and evidence for this in animal models is limited. In pediatric patients undergoing myeloablative autologous HCT for Hodgkins disease, 44% of patients develop diffuse pulmonary toxicity. This complication was not related to the method of transplantation conditioning (irradiation versus cytotoxic chemotherapy), but was associated with a pretransplantation history of atopy (allergic rhinitis or asthma), with an 80% incidence among those with an atopic history compared with 20% among those without an atopic history. While investigating the genetic causes of AHR in mice, we discovered two previously unidentified determinants of AHR following myeloablative and nonmyeloablative transplantation conditioning protocols using irradiation.

Materials/Methods:

BALB/c (atopic) and BALB/c congenic C.D2Es-Hba (HBA) mice (non-atopic) were irradiated with nonmyeloablative (450-550 Rad) or myeloablative (900 Rad) doses prior to adoptive transfer of splenocytes (SPC) or bone marrow cells (BMC), respectively. Three days following the cell transfer, a standard airway sensitization protocol was initiated, using ovalbumin and alum i.p., followed one week later by three daily doses of intranasal ovalbumin (50 ug/ml). Airway hyperreactivity (Penh) was assessed by whole body plethysmography with increasing challenges of nebulized methacholine. After airway testing, the mice were euthanized and lung tissues were obtained for histology.

Results: Airway hyperreactivity was induced in BALB/c mice reconstituted with BALB/c SPC or BMC. However, non-atopic HBA mice resisted the development of AHR, whether reconstituted with BALB/c or HBA SPC or BMC. BALB/c reconstituted with HBA cells resisted AHR with Penh levels comparable to HBA mice reconstituted with HBA cells. We were surprised to find that the timing of cell transfer and immunization influenced the development of airway hyperreactivity. Cell transfers performed within 1-2 hours of irradiation were associated with the development of AHR in all mice, while transfer between 8-12 hours after irradiation did not modify the airway sensitization.

CONCLUSIONS

Pulmonary toxicity following HCT is a complex phenomenon, influenced by genetic factors and by transplantation protocol. Our results in mice confirm retrospective observations in humans that atopic predisposition is a major risk factor for the development of airway hyperreactivity after transplantation. These studies are the first to demonstrate that one of the multiple factors involved in susceptibility to pulmonary toxicity after transplantation is a radioresistant cell population that can be adoptively transferred with spleen or bone marrow cells. We also demonstrate that the timing of HCT cell transfusion contributes to the development of airway hyperreactivity.

What is claimed is:

1. A method for the treatment of malignancy in an individual, the method comprising:

administering to said individual an agonistic antibody or fragment thereof that specifically binds to a human T cell/transmembrane, immunoglobulin, and mucin (TIM) encoded polypeptide selected from TIM-1 polypeptide and human TIM-4 polypeptide, in combination with radiation therapy.

2. The method according to claim 1, wherein said TIM polypeptide is TIM-1.

3. The method according to claim 1, wherein said TIM polypeptide is TIM-4.

4. The method of claim 1, wherein distribution of phosphatidylserine (PS) in the individual is determined prior to or in conjunction with administering said antibody or fragment thereof, wherein an individual in which the PS is bound to a tumor cell of the malignancy is selected for administration of the antibody or fragment thereof.

5. The method of claim 4, wherein the distribution of phosphatidylserine is determined by in vivo imaging with a labeled phosphatidylserine binding agent.

6. A method for the treatment of malignancy in an individual, the method comprising:

administering to said individual an antagonistic antibody or fragment thereof that specifically binds to human T cell/transmembrane, immunoglobulin, and mucin (TIM) encoded polypeptide TIM-3 in combination with radiation therapy to a local irradiation field, wherein the antagonistic antibody is provided at a dose that boosts immune responsiveness after radiation therapy to generate a response to sites of metastatic disease outside of the irradiation field.

* * * * *